(12) United States Patent
Cheng

(10) Patent No.: US 8,865,162 B2
(45) Date of Patent: *Oct. 21, 2014

(54) MONOCLONAL ANTIBODIES AGAINST HPV PROTEINS

(75) Inventor: Shuling Cheng, Fremont, CA (US)

(73) Assignee: OncoHealth Corp., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/456,053

(22) Filed: Jun. 10, 2009

(65) Prior Publication Data

US 2009/0312527 A1    Dec. 17, 2009

Related U.S. Application Data

(60) Provisional application No. 61/131,991, filed on Jun. 13, 2008, provisional application No. 61/192,912, filed on Sep. 22, 2008.

(51) Int. Cl.
| | | |
|---|---|---|
| *A61K 39/395* | (2006.01) | |
| *G01N 33/569* | (2006.01) | |
| *G01N 33/571* | (2006.01) | |
| *C12Q 1/70* | (2006.01) | |
| *C07K 16/08* | (2006.01) | |

(52) U.S. Cl.
CPC .......... *C12Q 1/708* (2013.01); *G01N 2333/025* (2013.01); *G01N 33/56983* (2013.01); *G01N 33/571* (2013.01); *C07K 16/084* (2013.01); *G01N 2469/10* (2013.01)
USPC ................ 424/130.1; 424/230.1; 435/70.21

(58) Field of Classification Search
CPC .. C07K 2317/34; C07K 16/248; A61K 45/06; A61K 39/12
See application file for complete search history.

(56) References Cited

U.S. PATENT DOCUMENTS

| | | |
|---|---|---|
| 3,633,999 A | 1/1972 | Buckles |
| 4,511,220 A | 4/1985 | Scully |
| 4,619,508 A | 10/1986 | Shibuya et al. |
| 4,744,615 A | 5/1988 | Fan et al. |
| 4,851,978 A | 7/1989 | Ichihara |
| 5,045,447 A | 9/1991 | Minson |
| 5,057,411 A | 10/1991 | Lancasater et al. |
| 5,061,025 A | 10/1991 | Debesis |
| 5,109,465 A | 4/1992 | Klopotek |
| 5,183,755 A | 2/1993 | Ohmoto et al. |
| 5,224,200 A | 6/1993 | Rasmussen et al. |
| 5,233,460 A | 8/1993 | Partlo et al. |
| 5,307,207 A | 4/1994 | Ichihara |
| 5,315,427 A | 5/1994 | Rauch et al. |
| 5,328,785 A | 7/1994 | Smith et al. |
| 5,357,365 A | 10/1994 | Ipposhi et al. |
| 5,401,627 A | 3/1995 | Dillner et al. |
| 5,415,995 A | 5/1995 | Schoolnik et al. |
| 5,453,814 A | 9/1995 | Aiyer |
| 5,561,081 A | 10/1996 | Takenouchi et al. |
| 5,591,574 A | 1/1997 | Orth et al. |
| 5,610,733 A | 3/1997 | Feldman et al. |
| 5,621,529 A | 4/1997 | Gordon et al. |
| 5,629,161 A | 5/1997 | Muller et al. |
| 5,662,410 A | 9/1997 | Suganuma |
| 5,665,535 A | 9/1997 | Orth et al. |
| 5,679,509 A | 10/1997 | Wheeler et al. |
| 5,695,770 A | 12/1997 | Raychaudhuri et al. |
| 5,699,191 A | 12/1997 | Fork |
| 5,754,278 A | 5/1998 | Kurtz |
| 5,876,723 A | 3/1999 | Cole et al. |
| 5,888,888 A | 3/1999 | Talwar et al. |
| 5,914,389 A | 6/1999 | Huibregtse et al. |
| 6,013,262 A | 1/2000 | Frazer et al. |
| 6,228,578 B1 | 5/2001 | Impraim et al. |
| 6,329,167 B1 | 12/2001 | Patterson et al. |
| 6,355,424 B1 | 3/2002 | Lorinez et al. |
| 6,420,106 B1 | 7/2002 | Gyllensten et al. |
| 6,489,105 B1 | 12/2002 | Matlashewski et al. |
| 6,524,825 B1 | 2/2003 | Mizzen et al. |
| 6,528,278 B2 | 3/2003 | Patterson et al. |
| 6,709,832 B1 | 3/2004 | Doeberitz et al. |
| 6,743,593 B2 | 6/2004 | Hu |
| 6,827,933 B2 | 12/2004 | Orth et al. |
| 6,884,786 B1 | 4/2005 | Kieny et al. |

(Continued)

FOREIGN PATENT DOCUMENTS

| | | |
|---|---|---|
| CN | 03825051.9 | 11/2005 |
| EP | 00256321 | 2/1988 |

(Continued)

OTHER PUBLICATIONS

Oltersdorf et al. (Journal of General Virology, 1987, vol. 68, p. 2933-2938).*
Christensen et al. (Virology, 1996, vol. 174, p. 174-184).*
DiBonito et al. (Infectious Agents and Cancer, 2006, p. 1-9).*
Bosch F X, Manos M M, Munoz N, et al 1995. Prevalence of human papillomavirus in cervical cancer: a worldwide perspective. J Natl Cancer Inst 87:796-802.
Kiviat N B, and Koutsky L A. 1993. Specific human papillomavirus types as the causal agents of most cervical intraepithelial neoplasia: implications for current views and tr.
Koutsky L A, Holmes K K, Critchlow C W, et al. 1992. A cohort study of the risk of cervical intraepithelial neoplasia grade 2 or 3 in relation to papillomavirus infection.

(Continued)

*Primary Examiner* — Agnieszka Boesen
(74) *Attorney, Agent, or Firm* — Yi-Shan Yang; Fenwick & West LLP

(57) ABSTRACT

Embodiments of the invention provide methods, monoclonal antibodies, polyclonal antibodies, assays, and kits for detecting HPV infection and HPV related cancer diagnosis, including infection by various HPV genotypes, early and/or late stage HPV-associated or HPV-specific cancers. Various monoclonal antibodies recognizing specific epitope for specific HPV protein or HPV type, common epitope for various HPV proteins or HPV types are obtained. These obtained monoclonal antibodies are useful tools in early clinical detection of HPV infection and general detection of HPV related diseases, specific detection of invasive cervical cancer, detection of other HPV related cancers, early stage precancerous lesions as well as late stage cancer progression.

10 Claims, 12 Drawing Sheets

(56) References Cited

U.S. PATENT DOCUMENTS

| | | | |
|---|---|---|---|
| 6,890,514 B2 | 5/2005 | Mathur et al. | |
| 6,900,035 B2 | 5/2005 | Mizzen et al. | |
| 6,933,123 B2 | 8/2005 | Hu et al. | |
| 6,939,687 B2 | 9/2005 | Patterson et al. | |
| 7,001,995 B1 | 2/2006 | Neeper et al. | |
| 7,078,061 B2 | 7/2006 | Debad et al. | |
| 7,157,233 B2 | 1/2007 | Fischer et al. | |
| 7,361,460 B2 | 4/2008 | Williams et al. | |
| 7,399,467 B2 * | 7/2008 | Lu et al. | 424/130.1 |
| 7,455,973 B2 | 11/2008 | Fischer et al. | |
| 7,501,261 B2 | 3/2009 | Meijer et al. | |
| 7,510,838 B2 | 3/2009 | Fischer et al. | |
| 7,838,215 B2 | 11/2010 | Gombrich et al. | |
| 7,888,032 B2 | 2/2011 | Patterson et al. | |
| 2001/0034021 A1 | 10/2001 | Muller et al. | |
| 2003/0044870 A1 | 3/2003 | Sehr et al. | |
| 2003/0143571 A1 | 7/2003 | Sharp et al. | |
| 2003/0190602 A1 | 10/2003 | Pressman et al. | |
| 2004/0018487 A1 | 1/2004 | Lu et al. | |
| 2004/0048833 A1 | 3/2004 | Kohn | |
| 2004/0170644 A1 | 9/2004 | Mailere et al. | |
| 2004/0175695 A1 | 9/2004 | Debad et al. | |
| 2004/0260157 A1 | 12/2004 | Montes et al. | |
| 2005/0037017 A1 | 2/2005 | Mizzen et al. | |
| 2005/0037342 A1 | 2/2005 | Mathur et al. | |
| 2005/0042600 A1 | 2/2005 | Hu et al. | |
| 2005/0142541 A1 | 6/2005 | Lu et al. | |
| 2005/0147621 A1 | 7/2005 | Higgins et al. | |
| 2005/0159386 A1 | 7/2005 | Kieny et al. | |
| 2005/0255460 A1 | 11/2005 | Lu et al. | |
| 2005/0255468 A1 | 11/2005 | Ridder et al. | |
| 2005/0260566 A1 | 11/2005 | Fischer et al. | |
| 2006/0029943 A1 | 2/2006 | Hermonat et al. | |
| 2006/0039919 A1 | 2/2006 | Chang et al. | |
| 2006/0121516 A1 | 6/2006 | Norman et al. | |
| 2006/0147906 A1 | 7/2006 | Zwerschke et al. | |
| 2006/0153864 A1 | 7/2006 | Gissmann et al. | |
| 2006/0154238 A1 | 7/2006 | Hu et al. | |
| 2006/0160069 A1 | 7/2006 | Chau et al. | |
| 2006/0172285 A1 | 8/2006 | Patterson | |
| 2006/0269967 A1 | 11/2006 | Chen et al. | |
| 2006/0286595 A1 | 12/2006 | Fischer et al. | |
| 2005/0147061 A1 | 3/2007 | Carlson et al. | |
| 2007/0048833 A1 | 3/2007 | Sprecher et al. | |
| 2007/0065810 A1 | 3/2007 | Schlegel et al. | |
| 2006/0002929 A1 | 5/2007 | Sprencher et al. | |
| 2007/0099199 A1 | 5/2007 | Lu et al. | |
| 2007/0117167 A1 | 5/2007 | Malinowski et al. | |
| 2007/0166699 A1 | 7/2007 | Zwerschke et al. | |
| 2007/0190062 A1 | 8/2007 | Malinowski et al. | |
| 2007/0190529 A1 | 8/2007 | Ridder et al. | |
| 2008/0038738 A1 | 2/2008 | Weigum et al. | |
| 2008/0267982 A1 | 10/2008 | Kiselev et al. | |
| 2009/0047660 A1 | 2/2009 | Lu et al. | |
| 2009/0075377 A1 | 3/2009 | Lu et al. | |
| 2009/0104597 A1 | 4/2009 | Gombrich et al. | |
| 2009/0148864 A1 | 6/2009 | Fischer et al. | |

FOREIGN PATENT DOCUMENTS

| | | |
|---|---|---|
| GB | 2379220 | 5/2003 |
| JP | 2002296274 | 10/2002 |
| JP | 2007503208 | 2/2007 |
| JP | 2007537705 | 12/2007 |
| TW | 95142312 | 11/2006 |
| TW | 100100781 | 1/2010 |
| TW | 201012932 | 4/2010 |
| TW | 201043958 | 12/2010 |
| WO | WO9700888 | 1/1997 |
| WO | WO9910375 | 3/1999 |
| WO | WO0204007 A2 | 1/2002 |
| WO | WO2004085683 | 10/2004 |
| WO | WO2005008248 | 1/2005 |
| WO | 2005063286 | 7/2005 |
| WO | WO2005/063286 | 7/2005 |
| WO | WO2005088311 | 9/2005 |
| WO | WO2006083984 | 8/2006 |
| WO | WO2007059492 | 5/2007 |
| WO | WO2007095320 | 8/2007 |
| WO | WO2009042488 | 4/2009 |
| WO | 2009079192 | 6/2009 |
| WO | WO2009151632 | 12/2009 |
| WO | WO2009151633 | 12/2009 |
| WO | WO2010129821 | 11/2010 |
| WO | WO2011084598 | 7/2011 |

OTHER PUBLICATIONS

Kuroda M, Kiyono T, Oikawa K, Yoshida K, Mukai K. 2005. The human papillomavirus E6 and E7 inducible oncogene, hWAPL, exhibits potential as a therapeutic target. Br J Cance.

Lehtinen M, Luukkaala T Wallin K L, et al. 2001. Human papillomavirus infection, risk for subsequent development of cervical neoplasia and associated population attributable.

Li T, Zhao L, Liu Z, Han Y, and Fan D. 2005. Regulation of apoptosis by papillomavirus E6 oncogene. World J Gastroenterol 11:931-37.

Longworth M S, Laimins L A, 2004. Pathogenesis of human papillomavirus in differentiating epithelia. Microbiol Mol Biol Rev 68: 362-72.

Madrigal M, Janicek M F, Sevin B U, et al. 1997. In vitro antigene therapy targeting HPV-16 E6 and E7 in cervical carcinoma. Gynecol Oncol 64: 18-25.

Mougin C, Dalstein V, Pretet J L, et al. 2001. Epidemiology of cervical papillomavirus infections. Recent knowledge. Press Med 30: 1017-23.

Munoz N, Bosch X, Sanjose S, Herrero R, et al. 2003. Epidemiologic classification of human papillomavirus types associated with cervical cancer. N Engl J Med 348:518-27.

Fisher, et al. "The Association of Human Papillomavirus Type 16 E6 and E7 Antibodies with stage of Cervical Cancer", Gynecologic Oncology 61, 73-78 (1996) Article No. 0099.

Veress, et al. "Human Papillomavirus DNA and Anti-HPV Secretory IgA Antibodies in Cytologically Normal Cervical Specimens" Journal of Medical Virology 43:201-207 (1994).

Meschede, et al. "Antibodies agains Early Proteins of Human Papillomaviruses as Diagnostic Markers for Invasive Cervical Cancer" Journal of Clinical Microbiology Feb. 1998, pp.

Park, et al. "HPV-16-Related Proteins as the Serolgic Markers in Cervical Neoplasia", Gynecologic Oncology 69, 47-55 (1998).

Viscidi, R. P., S. Yeping, B. Tsuzaki, F. X. Bosch, N. Munoz, and K. Shah. 1993. Serologic response in human papillomavirus—associated invasive cervical cancer. Int. J. Cancer.

Walboomers, et al. "Human Papillomavirus is a Necessary Cause of Invasive Cervical Cancer Worldwide", Jouranl of Pathology 189: 12-19 (1999).

Zumbach, et al "Antibodies Against Oncoproteins E6 and E7 of Human Papillomavirus Types 16 and 18 in Cervical-Carcinoma Patents from Russia", Int. J. Cancer 85, 313-318 (2000).

Sehr, et al. "A generic capture ELISA for recombinant proteins fused to glutathione S-transferase: validation for HPV serology" Journal of Immunological Methods 253 (2001) 153.

Berumen et al. 2001 Asian-American Variants of Human Papillomavirus 16 and Risk for Cervical Cancer: a Case-Control Study Journal of the National Cancer Institute, vol. 93, No.

Bosch et al. 2002 The causal relation between human papillomavirus and cervical cancer. J. Clin. Pathol.;55;244-265.

Kreimer A R, Clifford G M, Snijders P J, et al. 2005. HPV 16 semiquantitative viral load and serological biomarkers in oral and oropharyngeal squamous cell carcinomas. Int.

Nindl, I., L. Benitez-Bribiesca, J. Berumen, N. Farmanara, S. Fisher, G. Gross, L. Lopez-Carillo, M. Müller, M. Tommasino, A. Vazquez-Curiel, and L. Gissmann 1994. Antibodies.

Snijders et al. 2006 HPV-mediated cervical carcinogenesis: concepts and clinical implications J Pathol 2006; 208: 152-164.

Stoppler, et al. 1996 Natural Variants of the Human Papillomavirus Type 16 E6 Protein Differ in Their Abilities to Alter Keratinocyte Differentiation and to Induce p53 Degra.

(56) References Cited

OTHER PUBLICATIONS

Tornesello et al. 2004 Analysis of human papillomavirus type-16 variants in Italian women with cervical intraepithelial neoplasia and cervical cancer. J Med Virol. ;74(1):117-.

Banks et al. 1987 Identification of human papillomavirus type 18 E6 polypeptide in cells derived from human cervical carcinomas J gen Virol (1987) 68:1351-1359.

Oltersdorf et al 1987 Identification of human papillomavirus type 16 E7 protein by monoclonal antibodies J Gen Virol (1987) 68:2933-2938.

Patel et al 1989 Reactivities of polyclonal and monoclonal antibodies raised to the major capsid protein of human papillomavirus type 16 J Gen Vriol 70: 69-77.

Seedorf et al 1987 identification of early proteins of the human papillomavirus type 16 (HPV 16) and type (HPV 18) in cervical carcinoma cells EMBO 6(1)139-144.

Fiedler et al 2005 Expression of the high-risk human papillomavirus type 18 and 45 E7 oncoproteins in cervical carcinoma biopsies J Gen Birol 86:3235-3241.

Androphy et at 1987 Identification of the HPV-16 E6 protein from transformed mouse cells and human cervical carcinoma cell lines EMBO 6(4) 989-992.

Andersson et al 2006 Expression of E6/E7 mRNA from high rish human papillomavirus in relation to CIN grade, viral load and p16INK4a Int J oncology 29:70-711.

Keegan et al 2009 Comparison of HPV detection technologies: Hybrid capture 2, preTect HPV proofer and analysis of HPV DNA viral load in HPV 16, HPV 18 and HPV 33 E6/E7 mRNA p.

Seedorf, K. et al., (1987) The EMBO Journal vol. 6 pp. 139-144. Identification of early proteins of the human papilloma viruses type 16 (HPV 16) and type 18 (HPV 18) in cervical carcinoma cells.

Kearney, JF et al. (1979) The Journal of Immunology, V123, No. 4, 1548-1550. "A New Mouse Myeloma Cell Line that has Lost Immunoglobulin Expression but Permits the Construction of Antibody-Secreting Hybrid Cell Lines".

Christensen, ND et al., (1994) Journal of General Virology, V75, 2271-2276. Assembled baculovirus-expressed human papillomavirus type 11 LI capsid protein virus-like particles are recognized by neutralizing monoclonal antibodies and induce high titres of neutralizing antibodies.

Graham, AK et al. (1991) Journal of Clinical Pathology, V44, 96-101. "Simultaneous in situ genotyping and phenotyping of human papillomavirus cervical lesions: Comparative sensitivity and specificity".

Kee, SH et al. (1997) J. Korean Soc. Microbiology, vol. 32, No. 3, 335-342. "Generation of Monoclonal Antibodies Against Human Papillomavirus Type16 E7 Protein: Usefulness for Various E7 Detection Systems".

Christensen, ND et al. (1994) Journal of General Virology, 75, 2271-2276. "Assembled baculovirus-expressed human papillomavirus type 11 LI capsid protein virus-like particles are recognized by neutralizing monoclonal antibodies and induce high titres of neutralizing antibodies".

Arbyn et al., 2009. J Cell Mol Med. vol. 13 No. 4 648-659. "Triage of women with equivocal or low-grade cervical cytology results: a meta-analysis of the HPV test positivity rate".

Andersson et al., 2006. International Journal of Oncology 29: 705-711. "Expression of E6/E7 mRNA from 'high risk' human papillomavirus in relation to CIN grade, viral load and p16INK4a".

Balasubramanian et al., Cancer Epidemiol Biomarkers Prev 2009;18:3008-3017. "Evaluation of an ELISA for p16INK4a as a Screening Test for Cervical Cancer".

Cardenas-Turanzas et al., Gyn Oncology 107 (2007) S138-S146. "The clinical effectiveness of optical spectroscopy for the in vivo diagnosis of cervical intraepithelial neoplasia: Where are we?"

Castle et al., 2010. AACCP. Benefits and risks of HPV testing in cervical cancer screening See Online/Articles D0I:10.1016/S1470-2045(09)70360-2.

Castle et al., American Journal of Obstetrics & Gynecology Oct. 2007 "Risk assessment to guide the prevention of cervical cancer".

Choi et al., Biosensors and Bioelectronics 20 (2005) 2236-2243. "Adenoviral p53 effects and cell-specific E7 protein-protein interactions of human cervical cancer cells".

Cole et al., Journal of Virology, Jun. 1986, vol. 58. No. 3. p. 991-995. "Genome Organization and Nucleotide Sequence of Human Papillomavirus Type 33, Which is Associated with Cervical Cancer".

Cole et al., J. Mol. Biol. (1987) 193, 599-608. "Nucleotide Sequence and Comparative Analysis of the Human Papillomavirus Type 18 Genome Phylogeny of Papillomaviruses and Repeated Structure of the E6 and E7 Gene Products".

Sawaya 2008 Annals of Internal Medicine vol. 148 • No. 7 p. 557 "Adding Human Papillomavirus Testing to Cytology for Primary Cervical Cancer Screening: Shooting First and Asking Questions Later".

Fuchs et al., Journal of Virology, May 1986, p. 626-634. vol. 58, No. 2 "Epidermodysplasia Verruciformis-Associated Human Papillomavirus 8: Genomic Sequence and Comparative Analysis".

Garcia-Alai et al., Biochemistry 2007, 46, "High-Risk HPV E6 Oncoproteins Assemble into Large Oligomers that Allow Localization of Endogenous Species in Prototypic HPV-Transformed Cell Lines".

Gravitt et al., Vaccine 265 (1008) K42-K52. "New Technologies in Cervical Cancer Screening".

Kulasingam et al., Obstetrics & Gynecology vol. 107, No. 2, Part 1, Feb. 2006 Cost-effectiveness of Extending Cervical Cancer Screening Intervals Among Women With Prior Normal Pap Tests.

Mao et al., Int. J. Cancer: 120, 2435-2438 (2007) "Evaluation of a new p16INK4a ELISA test and a high-risk HPV DNA test for cervical cancer screening: Results from proof-of-concept study".

Molden et al., Int. J. Cancer: 114, 973-976 (2005) "Predicting CIN2 when detecting HPV mRNA and DNA by PreTect HPV-Proofer and consensus PCR: a 2-year follow-up of women with ASCUS or LSIL Pap smear".

Marimatsu et al., Am J Clin Pathol 2005;123:716-723 "High-Throughput Cervical Cancer Screening Using Intracellular Human Papillomavirus E6 and E7 mRNA Quantification by Flow Cytometry".

NCCN Clinical Practice Guidelines in Oncology™ v.2. 2007 Cervical Cancer Screening.

Negri et al., Am J Surg Pathol 2008;32:1715-1720 "p16ink4a and HPV L1 Immunohistochemistry is Helpful for Estimating the Behavior of Low-grade Dysplastic Lesions of the Cervix Uteri".

Norchip et a;., 22nd. International Papillomavirus Conference, Vancouver, BC, Canada, Apr. 30-May 6, 2005 "Persistent transforming HPV infection may correlate with persistent histologically defined CIN II+ Summary of studies by Frank Karlsen and Hanne Skomedal".

Trope et al., Journal of Clinical Microbiology, Aug. 2009, p. 2458-2464. "Pe rformance of Human Papillomavirus DNA and mRNA Testing Strategies for Women with and without Cervical Neoplasia".

Schiffman et al., Arch Pathol Lab Med—vol. 127, Aug. 2003. "Findings to Date From the ASCUS-LSIL Triage Study (ALTS)." pp. 946-949.

Woodman et al., "The natural history of cervical HPV infection: unresolved issues." Nature Review Cancer, vol. 7 | Jan. 2007 | 11.

Ronco et al., BMC Women's Health 2008, 8:23. "New paradigms in cervical cancer prevention: opportunities and risks">.

Talora et al., Genes Dev. 2002 16: 2252-2263. Specific down-modulation of Notch1 signaling in cervical cancer cells is required for sustained HPV-E6/E7 expression and late steps of malignant transformation.

Tungteakkhun wr al., Arch Virol (2008) 153:397-408. "Cellular binding partners of the human papillomavirus E6 protein".

Sellor et al., Journal of Lower Genital Tract Disease, vol. 15, No. 2, 2011, 169-176. Association of Elevated E6 Oncoprotein With Grade of Cervical Neoplasia Using PDZ InteractionYMediated Precipitation of E6.

Ronco et al., "Effi cacy of human papillomavirus testing for the detection of invasive cervical cancers and cervical intraepithelial neoplasia: a randomised controlled trial:." Published Online Jan. 19, 2010.

(56) References Cited

OTHER PUBLICATIONS

Schneider-Gadicke et al., The EMBO Journal vol. 5 No. 9 pp. 2285-2292, 1986. "Different human cervical carcinoma cell lines show similar transcription patterns of human papillomavirus type 18 early genes."
Wentzensen et al., Disease Markers 23 (2007) 315-330. "Biomarkers in cervical cancer screening."
Molder et a;., Cancer Epidemiology Biomarkers and Prevention. 2005, 14, p. 367. Comparison of Human Papillomavirus Messeger DNA and DNA detection: A crodd sectional study of 4136 wk e > 30 years of age with a 2, year fikkiw-up of high=grade squamous intraepitehlial Lesion.
Sawaya et al., 2005. www.nejm.org May 10, 2007. "HPV Vaccination—More Answers, More Questions."
Perez et al., 2009. 25th International Papillomavirus Conference, Sweden. "Detection of HPV E6/E7 Oncoporteins in Cervical Cancer."
Parkin et al., Int. J. Cancer: 80, 827-841 (1999). "Estimates of the Worldwide Incidence of 25 Major Cancers in 1990."
Schneider et al., 1991 Int. j. Gynecol Pathol. 10:1-14 "Prevalence of Human Papillomavirus Genomes in Tissue from the Lower Genital Tract as Detected by Molecular in situ hybridization."
Segnan et al., 1994 European Journal of Cancer vol. 30, 873-875. "Cervical cancer screening. Human benefits and human costs in the evaluation of screening programmes."
Partridge et al., 2008 J. National Compr. Cancer Network 6: 58-82. Abstract only.
Heck et al., 1992 Proc. Natl. Acad. Sci. USA vol. 89, pp. 4442-4446, May 1992. "Efficiency of binding the retinoblastoma protein correlates with the transforming capacity of the E7 oncoproteins of the human papillomaviruses."
Chellappan et al., 1992 Proc. Natl. Acad. Sci. USA vol. 89, pp. 4549-4553, May 1992. "Adenovirus EIA, simian virus 40 tumor antigen, and human papillomavirus E7 protein share the capacity to disrupt the interaction between transcription factor E2F and the retinoblastoma gene product."
Dyson et al., Science 1989. 243: 934-937. "The Human Papilloma Virus-16 E7 Oncoprotein is Able to Bind to the Retinoblastoma Gene Product."
Zerfass et al., J. Virol. 1995, 69(10):6389. "Sequential activation of cyclin E and cyclin A gene expression by human papillomavirus type 16 E7 through sequences necessary for transformation."
Zerfass-Thome et al., 1996 Oncogene 13:2323-2330. "Inactivation of the cdk inhibitor p27KIP1 by the human papillomavirus type 16 E7 oncoprotein."
Saint, M., G. Gildengorin, and G. F. Sawaya. 2005. Current Cervical Neoplasia Screening Practices of Obstetriciaqn/Gynecologists in the US. Am. J. Obstet. Gynecol. 192:414-421.
SJ Lee et al., J Immunol (2001); 167; 497-504. "Both E6 and E7 Oncoproteins of Human Papillomavirus 16 Inhibit IL-IS-Induced IFN-'Y Production in Human Peripheral Blood Mononuclear and NK Cells."
S Vazquez-Vega et al., BMC Cancer (2007). 7(Suppl 1), A21. "Expression of viral and cellular cycle proteins and proteinases in cervical carcinoma cell lines as possible immunocytochemical markers of malignant phenotype."
J Doorbar, (2006) Clinical Science 1, 10, 525-541. "Molecular biology of human papillomavirus infection and cervical cancer."
M Fiedler et al., (2004) The FASEB Journal vol. 18 pp. 1120-1122. "High level HPV-16 E7 oncoprotein expression correlates with reduced pRb-levels in cervical biopsies."
KH Kim et al., (1994) Yonsei Medical Journal vol. 35, No. 1, pp. 1-9. "Expression and Localization of Human Papillomavirus Type 16 E6 and E7 Open Reading Frame Proteins in Human Epidermal Keratinocyte."
M Fiedler et al., (2005) Journal of General Virology, 86, 3235-3241. "Expression of the high-risk human papillomavirus type 18 and 45 E7 oncoproteins in cervical carcinoma biopsies."
E Guccione et al., (2002) Virology 283, 20-25. "Comparative Analysis of the Intracellular Location of the High- and Low-Risk Human Papillomavirus Oncoproteins."
H Valdovinos-Torres et al., (2008) The Open Virology Journal vol. 2. 15-23. "Different Isoforms of HPV-16 E7 Protein are Present in Cytoplasm and Nucleus."
T Li et al., (2001) Carcinogenesis vol. 22. No. 6 pp. 929-934. "Human papillomavirus type 16 is an important infections factor in the high incidence of esophageal cancer in Anyang area of China."
Blevins et al., Applied and Environmental Microbiology 2007, pp. 1501-1513. "Adaptation of a Luciferase Gene Reporter Aand lac ExpressionSystem to *Borrelia burgdorferi*."
EA Mirecka et al., (2006) Protein Expression and Purification 48, 281-291. "Expression and purification of His-tagged HPV16 E7 protein active in pRb binding/".
MS Lechner et al., (1994) Journal of Virology, Jul. 1994, p. 4262-4273. "Inhibition of p53 DNA Binding by Human Papillomavirus E6 Proteins."
B Bjorndal et al., (2003) Protein Expression and Purification 31 (2003) 47-55. "Expression and purification of receptor for activated C-kinase 1 (RACKI)."
ND Christensen et al., (1996) Virology 223, 174-184. "Surface Conformational and Linear Epitopes on HPV-16 and HPV-18 L1 Virus-like Particles as Defined by Monoclonal Antibodies".
Y Nomine et al., (2001) Protein Engineering vol.I4 No. 4 pp. 297-305, "A strategy for optimizing the monodispersity of fusion proteins: application to purification of recombinant HPV E6 oncoprotein."
ND Christensen et al., (1994) Journal o/General Virology (1994), 75, 2271-2276. "Assembled baculovirus-expressed human papillomavirus type 11 LI capsid protein virus-like particles are recognized by neutralizing monoclonal antibodies and induce high titres of neutralizing antibodies."
T Oltersdorf et al., (1987) J. gen. Viral. (1987), 68, 2933-2938. "Identification of Human Papillomavirus Type 16 E7 Protein by Monoclonal Antibodies."
P Di Bonito et al., (2006) Infectious Agents and Cancer 2006, 1:6. "Serum antibody response to Human papillomavirus (HPV) infections detected by a novel ELISA technique based on denatured recombinant HPVI6 LI, L2, E4, E6 and E7 proteins."
JF Kearney et al., (1979) The Journal of Immunology, V 123 No. 4 p. 1548-1550. "A New Mouse Myeloma Cell Line That Has Lost Immunoglobulin Expression But Permits the Construction of Antibody-Secreting Hybrid Cell Lines."
K Seedorf et al., The EMBO Journal 1987, vol. 6, pp. 139-144. Identification of Early Proteins of the Human Papilloma Viruses Type 16 (HPV 16) and Type 18 (HPV 18) in Cervical Carcinoma Cells.
D Patel et al., (1989) J. gen. Virol. (1989),70,69-77. "Reactivities of Polyclonal and Monoclonal Antibodies Raised to the Major Capsid Protein of Human Papillomavirus Type 16."
S-H Kee et al., (1997) J. Korean Soc. Microbiol., vol. 32, No. 3, "Generation of Monoclonal Antibodies Against Human Papillomavirus Type16 E7 Protein: Usefulness for Various E7 Detection Systems."
AK Graham et al., (1991) Clin Pathol 1991;44:96-101. "Simultaneous in situ genotyping and phenotyping of human papillomavirus cervical lesions: Comparative sensitivity and specificity."
HG Kochel et al., (1991) Inl. J. Cancer: 48, 682-688. "Occurrence of Antibodies to Lt, L2, E4 and E7 Gene Products of Human Papillomavirus Types 6b, 16 and 18 Among Cervical Cancer Patients and Controls."
AK Ghosh et al., (1993) Int. J. Cancer: 53. 591-596. "Serological Responses to HPV 16 in Cervical Dysplasia and Neoplasia: Correlation of Antibodies to E6 With Cervical Cancer."
SA Jenison et al., (1990) The Journal of Infectious Disease162:60-69. "Evidence of Prevalent Genital-Type Human Papillomavirus Infections in Adults and Children."
T Fule et al., (2006) Virology 348, 289-396. "The presence of human papillomavirus 16 in neural structures and vascular endothelial cells."
Tommasino et al., Oncogene 1993, vol. 8, pp. 195-202. HPV16 E7 Protein Associates with the Protein Kinase p22 CDK2 and Cyclin A.
de Villiers et at., Virology 2004, vol. 324, pp. 17-27. "Classification of Papillomaviruses".

(56) References Cited

OTHER PUBLICATIONS

Banks et al., J. gen. Virol. 1987, vol. 68, pp. 1351-1359, "Identification of human papillomavirus type 18 E6 polypeptide in cells derived from human cervical carcinomas".
Thermo Scientific, Product Data Sheet for Human Papilloma Virus type 16-E7 (HPV 16-e7) Ab-1 (TVG701Y) Mouse Monoclonal Antibody. Dec. 8, 2011.
BioDesign Internation, Product Data Sheet for MAb to HPV16 E7 protein 716-218. Feb. 1, 2006.
BioDesign Internation, Product Data Sheet for MAb to HPV16 E7 protein 716-325. Aug. 3, 2005.
Chemicon International, Product Data Sheet for Mouse anti-human Papilloma Virus 16,18 E6 (C1P5) Monoclonal Antibody. Nov. 10, 2000.
Dako, Product Data Sheet for Monoclonal Mouse anti-Human Papillomavirus Clone K1H8. 2010.
G Volgareva et al., BMC Cancer 2004, 4:58. "Protein p16 as a marker of dysplastic and neoplastic alterations in cervical epithelial cells."
Digene Corporation, "hc2 HPV DNA Test," Ref. 5198-1220, 2007, 56 pages.
Matlashewski G., et al. The expression of human papillomavirus type 18E6 proteins in bacteria and the production of anti-E6 antibodies J Gen Virol (1986) 67: 1909-1916.
Radhakrishna pillai et al 1998 High-risk human papillomavirus infection and E6 protein expression in lesions of the uterine cervix Pathobiology 66(5) 240-246.
Ressler et al 2007 High-risk human popillomavirus E7 oncoprotein detection in cervical squamous cell carcinoma Clin Cancer Res 13(23) 7067-7072.
Androphy et al 1987 Identification of the HPV-16 E6 protein from transformed mouse cells and human cervical carcinoma cell lines EMBO 6(4) 989-992.
Andersson et al 2006 Expression of E6/E7 mRNA from high rish human papillomavirus in relation to CIN grade, viral load and p161NK4a Int J oncology 29:70-711.
Keegan et al 2009 Comparison of HPV detection technologies: Hybrid capture 2, preTect HPV prooer and analysis of HPV DNA viral load in HPV 16, HPV 18 and HPV 33 E6/E7 mRNA.
Inoue et al 1990 A novel monoclonal antibody against squamous cell carcinoma Jpn J Cancer res 81:176-182.
Advisory action for U.S. Appl. No. 12/456,055 dated Mar. 12, 2012.
LA Selvey et al., 1992 Journal of Virological Methods, 37, 119-128. "An ELISA capture assay for the E7 transforming proteins of HPV16 and HPV18."
H Griesser et al., 2004 Analyt Quant Cytol Histol 26, 241-245. "Correlation of Immunochemical Detection of HPV L1 capsid protein in Pap Smears with Regression of High-Risl HPV Positive Milk/Moderate Dysplasia."
Bosch, et al 1995. Prevalence of human papillomavirus in cervical cancer: a worldwide perspective. J Natl Cancer Inst 87:796-802.
Doeberitz, Magnus Von Knebel "New Molecular tools for efficient screening of cervical cancer", Disease Markers 17 (2001) 123-128.
Fisher, et al. "The Association of Human Papillomavirus Type 16 E6 and E7 Antibodies with stage of Cervical Cancer", Gynecologic Oncology 61,73-78 (1996) Article No. 0099.
Guimaraes, et al. 2005. "Immunohistochemical expression of p161NK4a and bcl-2 according to HPV type and to the progression of cervical squamous intraepitheliallesions". J Histochem Cytochem. 53: 509-16).
Hagensee, et al. "Detection of Cervical Antibodies to Human Papillomavirus Type 16 (HPV-16) Capsal Antigens in Relation to Detection of HPV-16 DNA and Cervcal Lesions", The Jourrnal of Infectious Diseases 2000; 181: 1234-9.
Kiviat, et al. 1993. Specific human papillomavirus types as the causal agents of most cervical intraepithelial neoplasia: implications for current views and treatment. J Natl Cancer Inst 85: 934-35.
Koutsky, et al. 1992. A cohort study of the risk of cervical intraepithelial neoplasia grade 2 or 3 in relation to papillomavirus infection. N Engl J med 327:1272-1278. Abstract Only.
Kuroda, et al. 2005. The human papillomavirus E6 and E7 inducible oncogene, hWAPL, exhibits potential as a therapeutic target. Br J Cancer 92:290-3.
Li, et al. 2005. Regulation of apoptosis by papillomavirus E6 oncogene. World J Gastroenterol 11:931-37.
Longworth, et al., 2004. Pathogenesis of human papillomavirus in differentiating epithelia. Microbiol Mol Bioi Rev 68: 362-72.
Madrigal, et al. 1997. In vitro antigene therapy targeting HPV-16 E6 and E7 in cervical carcinoma. Gynecol Oncol 64: 18-25.
Meschede, et al. "Antibodies agains Early Proteins of Human Papillomaviruses as Diagnostic Markers for Invasive Cervical Cancer" Journal of Clinical Microbiology Feb. 1998, pp. 475-480.
Munoz, et al. 2003. Epidemiologic classification of human papillomavirus types associated with cervical cancer. N Engl J Med 348:518-27.
Park, et al. 1995. Molecular biology of cervical cancer and its precursors. Cancer 76: 1902-13.
Park, et al. "HPV-16-Related Proteins as the Serolgic Markers in Cervical Neoplasia", Gynecologic Oncology 69,47-55 (1998).
Parkin, et al. 1993. Estimates of the worldwide incidence of eighteen major cancers in 1985. Int J Cancer 54:594-606.
Sehr, et al. "A generic capture ELISA for recombinant proteins fused to glutathione S-transferase: validation for HPV serology" Journal of ImmunoloQical Methods 253 (2001) 153-162.
Solomon, et al. 2002. The 2001 Bethesda Systems. Terminology for reportinQ results of cervical cytoloQY. JAMA 287:2114-19.
Studentsov, et al. "Polymer-Based Enzyme-Linked Immunosorbent Assay Using Human Papillomavirus Type 16 (HPV16) Virus-Like Particles Detects HPV16 Clade-Specific Serologic Responses", Journal of Clinical Microbiology Jul. 2003 pp. 2827-2834.
Sun, et al., "Comparison of Peptide Enzyme-Linked Immunosorbent Assay and Radioimmunoprecipitation Assay with in Vitro-Translated Proteins for Detection of Serum Antibodies to Human Papillomavirus Type 16 E6 and #7 Proteins" Journal of Clinical MicrobioloQY Sep. 1994 pp. 2216-2230.
Tjiong, et al. "Antibodies agains Human Papillomavirus Type 16 and 18 E6 and E7 Proteins in Cervicovaginal Washings and Serum of Patients with Cervical Neoplasia" Virallmjmunolgy vol. 14, No. 4, 2001 pp. 415-424.
Veress, et al. "Human Papillomavirus DNA and Anti-HPV Secretory IgA Antibodies in Cytologically Normal Cervical Specimens" Journal of Medical Virology 43:201-207—(1994).
Walboomers, et al. "Human Papillomavirus is a Necessary Cause of Invasive Cervical Cancer Worldwide", Jouranl of PatholoQv 189: 12-19 (1999).
Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.
Zumbach, et al "Antibodies Against Oncoproteins E6 and E7 of Human Papillomavirus Types 16 and 18 in Cervical-Carcinoma Patents from Russia", Int. J. Cancer 85, 313-318 (2000) [Publication of the International Union Against Cancer].
Fitzgerald Industries International Inc., Product Data Sheet for Monoclonal Antibody to human Papillomavirus (Early Protein), Human, Clone BF7. 2006.
Wang et al., Am J. Surg Patholo. 2004, vol. 28. No. 7, pp. 901-908 Detection of Human Papillomavirus DNA and Expression of p16, Rb, p53 proteins in small cell carcinomas of the uterine cervix.
Gabriella et al., BMC Cancer. 2007, vol. 7, pp. 25. Characterization of antibodies in single-chain format against the E7 oncoprotein of the human papillomavirus type 16 and their improvement by mutagenesis.
Arbyn, M., P. Sasieni, C. J. L. M. Meijer, C. Clavel, G. Koliopoulos, and J. Dillner. 2006. Chapter 9: Clinical applications of HPV testing: A summary of meta-analyses. Vaccine 24:78-89.
Castle, P. E., J. Dockter, C. Giachetti, F. A. Garcia, M. K. McCormick, A. L. Mitchell, E. B. Holladay, and D. P. Kolk. 2007. A cross-sectional study of a prototype carcinogenic human papillomavirus E6/E7 messenger RNA assay for detection of cervical precancer and cancer. Clinical cancer research : an official journal of the American Association for Cancer Research 13:2599-2605.

(56) References Cited

OTHER PUBLICATIONS

Cuschieri, K., and N. Wentzensen. 2008. Human Papillomavirus mRNA and p16 Detection as Biomarkers for the Improved Diagnosis of Cervical Neoplasia. Cancer Edidemiol. Biomarkers Prev. 17:2536-2545.
Dehn, D., K. C. Torkko, and K. R. Shroyer. 2007. Human Papillomavirus Testing and Molecular Markers of Cervical Dysplasia and Carcinoma. Cancer Cytopathology 111:1-14.
O'Sullivan, J. P., R. P. A'Hern, P. A. Chapman, L. Jenkins, R. Smith, and A. a. Nafussi. 1998. A case-control study of truepositive versus false-negative cervical smears in women with cervical intraepithelial neoplasia (CIN) III. Cytopathology 9:155-161.
Yim, E.-K., and J.-S. Park. 2006. Biomarkers in Cervical Cancer. Biomarker Insights 1:215-225.
Schiffman, M., A. G. Glass, N. Wentzensen, B. B. Rush, P. E. Castle, D. R. Scott, J. Buckland, M. E. Sherman, G. Rydzak, P. Kirk, A. T. Lorincz, S. Wacholder, and R. D. Burk. 2011. A long-term prospective study of type-specific human papillomavirus infection and risk of cervical neoplasia among 20,000 women in the Portland Kaiser Cohort Study. Cancer epidemiology, biomarkers & prevention : a publication of the American Association for Cancer Research, cosponsored by the American Society of Preventive Oncology 20:1398-1409.
Schweizer, J., P. S. Lu, C. W. Mahoney, M. Berard-Bergery, M. Ho, V. Ramasamy, J. E. Silver, A. Bisht, Y. Labiad, R. B. Peck, J. Lim, J. Jeronimo, R. Howard, P. E. Gravitt, and P. E. Castle. 2010. Feasibility study of a human papillomavirus E6 oncoprotein test for diagnosis of cervical precancer and cancer. Journal of clinical microbiology. 48:4646-4648.
Stoler, M. H., P. E. Castle, D. Solomon, and M. Schiffman. 2007. The Expanded Use of HPV Testing in Gynecologic Practice per ASCCP=Guided Manmagement Requires the Use of Well-Validated Assays. American Journal of Clinical Pathology 127:335-337.
Woodman, C. B. J., S. I. Collins, and L. S. Young. 2007. The natural history of cervical HPV infection: unresolved issues. Nature Reviews Cancer 7:11-22.
Advisory Action for U.S. Appl. No. 12/456,054 dated Jun. 13, 2012.
TIPO Search Report and Communication for Taiwan Invention Patent Application No. 095142312, Mar. 24, 2012. English search report on p. 1.
TIPO Search Report and Communication for Taiwan Invention Patent Application No. 098119611, Mar. 22, 2012. English search report on p. 1.
TIPO Search Report and Communication for Taiwan Invention Patent Application No. 098119612, Mar. 13, 2012. English search report on p. 1.
Volgareva et al., Protein p16 as a marker of dysplastic and neoplastic alterations in cervical epithelial cells. BMC Cancer 2004, 4:58. pp.
Liu et al., Preparation of monoclonal antibodies against human papillomavirus 16 E6 protein. Journal of Monoclonal Antibody, vol. 11 No. 3-4, Dec. 1995. English abstract on p. 3.
Su et al., Expression of human papillomavirus type 16 E6 oncogene production of monoclonal antibodies against HPV 16 E6 protein. Journal of Chinese Microbiology and Immunology, vol. 13 No. 3, 1993. English abstract on p. 4.
Wang et al., Expression of human papillomavirus type 16 L1 and construction of hybridoma cell strain of human papillomavirus type 16 L1 monoclonal antibody. Chin J. Endemiol, Jan. 20, 2007, vol. 26, No. 1. English abstract on p. 1.
Tindle RW et al., 1990 Journal of General Virology. 71, 1347-1354. "Identification of B epitopes in human papillomavirus type 16 E7 open reading frame protein."
Santa Cruz Biotechnology, Inc. Product Data Sheet for sc-18114 E6-AP (C-19). 2006.
Final Office action for U.S. Appl. No. 12/456,076 dated May 24, 2012.
Dorland's Pocket Medical Dictionary, P420, 25th Edition, 1995, W,B, Saunders Company. Philadelphia, Pennsylvania, 19106.
Notice of Allowance for U.S. Appl. No. 12/456,076 dated Aug. 1, 2012.
Examiner-Initiated Interview Summary and Amendment after Final initiated by the Examiner for U.S. Appl. No. 12/456,076 dated Aug. 1, 2012.
EPO Communication for App. No. 06846299.3, dated May 9, 2012.
Rocha-Zavaleta et al., 1997. British Journal of Cancer 75(8), 1144-1150. Differences in serological IgA responses to recombinant baculovirus-derived human papillomavirus E2 protein in the natural history of cervical neoplasia.
Non-final Office Action for U.S. Appl. No. 12/590,747 dated Aug. 15, 2012.
Kashmiri et al., Methods. 2005; 36:25-34.
Tamura et al., Journal of Immunology. 2000; 164:1432-1441.
Greenspan et al., Nature Biotechnology. 1999; 7:936-937.
Gillison et al., Journal of National Cancer Institute. 2008; 100:407-420.
Wu et al., Journal of General Virology. 2006; 87, 1181-1188.
http://www.biology-online.org/dictionary/Native_protein; Mar. 16, 2010.
European Patent Office Communication dated Dec. 3, 2012 for Application No. 09762929.9, PCT/US2009003538.
Oltersdorf et el., 1987. "Identification of Human Papillomavirus Type 16 E7 Protein by Monoclonal Antibodies." J. Gen. Virol. 68, 2933-2938.
Jochmus et al., 1999. "Chimeric Virus-like Partiles of the Human Papillomavirus Type 16 (HPV 16) as a Prophylactic and Therapeutic Vaccine." Archives of Medical Research. 30, 269-274.
HyTest NEWS. Mar. 2008, pp. 1-8. Advanced ImmunoChemical, Finland.
Mattil-Fritz et al., 2008. "Immunotherapy of equine sarcoid: dose-escalation trial for the use of chimeric papullomavirus-like particles." Journal of General Virology 89, 138-147.
Rizk et al., 2008. "Reactivity pattern of 92 monoclonal antibodies with 15 human papillomavirus types." Journal of General Virology, 89, 117-129.
Non-final Office Action for U.S. Appl. No. 12/456,054 dated Sep. 25, 2012.
Final Office Action for U.S. Appl. No. 12/456,053 dated Sep. 24, 2012.
JH Joen et al., "Immunocytochemical detection of HPV16E7 in cervical smear." 2007. Experimental and Molecular Medicine, vol. 39, No. 5, 621-628.
C Liang et al., "Biomarkers of HPV in Head and Neck Squamous Cell Carcinoma." 2012, Cancer Research. Published online Sep. 18, 2012.
D Holzinger et al., "Viral RNA Patterns and High Viral Load Reliably Define Oropharynx Carcinomas wit hActive HPV16 Involvement." 2012, Cancer Research. Published online Sep. 18, 2012.
AG Ostor et al., "Natural History of Cervical Intraepithelial Neoplasia: A Critical Review." 1993 International Journal of Gyncological Pathology . 12:186-192.
J Melnikow et al., 1998. "Natural history of Cervical Squamous Intraepithelial Lesions: A meta-Analysis." 1998 vol. 92, No. 4, pp. 727-735.
European Patent Office Communication dated Jan. 30, 2013 for Application No. 12164498.3-2402/2522756.
Non-final Office Action for U.S. Appl. No. 13/585,509 dated Jan. 15, 2013.
Qiao et al., 2008. "A New HPV-DNA Test for Cervical-Cancer Screening in Developing Regions: a Cross-Sectional Study of Clinical Accuracy in Rural China." Lancet Oncology 9: 929-936.
Zhao et al., 2010. "Performance of High-Risk Human Papillomavirus DNA Testing as a Primary Screening for Cervical Cancer: a Pooled Analysis of Individual Patient Data from 17 Population-Based Studies from China." Lancet Oncology 11: 1160-1171.
Zhao et al., 2011. "Pooled Analysis of a Self-Sampling HPV DNA Test as a Cervical Cancer Primary Screening Method." JNCI 104: 1-11.
Arbyn et al., 2010. "HPV-Based Cervical-Cancer Screening in China." World Health Organization GLOBOCAN 2008. Published online Nov. 12, 2010. http://globocan.iarcfr/.
Wong et al., 2011. "Efficacy of Abbott Real Time High Risk HPV Test in Evaluation of Atypical Squamous Cells of Undetermined Significance from an Asian Screening Population." Journal of Clinical Virology 51, 136-138.

(56) References Cited

OTHER PUBLICATIONS

Petignat et al., 2012. "Is It Time to Introduce HPV Seld-Sampling for Primary Cervical Cancer Screening?" Editorial, JNCI. 104 (3): pp. 1-2.
Japan Patent Office Communication dated Apr. 2, 2013 for Application No. 2011-513504.
Final Office Action for U.S. Appl. No. 12/456,054 dated May 14, 2013.
Taiwan Patent Office Communication dated Apr. 8, 2013 for Application No. 100100781.
Taiwan Patent Office Communication dated Apr. 3, 2013 for Application No. 095142312.
China Patent Office Communication dated Apr. 1, 2013 for Application No. 200980131078.4.
China Patent Office Communication dated Mar. 13, 2013 for Application No. 200980131077.X.
European Patent Office Communication dated Oct. 23, 2012 for Application No. 09762928.1, PCT/US2009003537.
Non-final Office Action for U.S. Appl. No. 13/029,131 dated Nov. 9, 2012.
EPO Communcation for Application No. 12164498.3 dated on Sep. 28, 2012.
MA Romanos et al., 1995. Production of a phosphorylated GST::HPV-6 E7 Fusion Protein Using a Yeast Expression Vector and Glutathione S-transferase Fusions. Gene. 152, 137-138.
Partial European Search Report for Application No. 12164498, dated Sep. 19, 2012.
T. Ristriani et al., 2001. "Specific Recognition of Four-way DNA Junctions by the C-terminal Zinc-binding Domain of HPV Oncoprotein E6." J. Mol. Biol. 305, 729-739.
KLMC Franken et al., 2000. "Purificaiton of His-Tagged PRoteins by Immobilized Chelate Affinity Chromatography: The Benefits from the Use of Organic Solvent." Protein Expression and Purification 18, 95-99.
Y. Nomine et al., 2001. "A strategy for optimizing the monodispersity of fusion proteins: application to purification of recombinant HPV E6 oncoprotein." Protein Engineering. 14, No. 4 pp. 297-305.
JA DeVoti et al., 2004. "Failure of Gamma Interferon but Not Interleukin-10 Expression in Response to Human Papillomavirus Type 11 E6 PRotein in Respiratory Papillomatosis." Clinical and Vaccine Immunology 11(3) 538-547.
TIPO Search Report and Communication for Taiwan Invention Patent Application No. 098119612, Oct. 5, 2012. Search Report Brief is on p. 1.
Japan Patent Office communication for JP Patent App. No. 2012-509989, Jan. 21, 2014.
China Patent Office communication for CN Patent App. No. 200980131077.x, Jan. 24, 2014.
Japan Patent Office Communication for JP Patent App. No. 2011-513505, Jan. 14, 2014.
Taiwan Patent Office Communication, Notice of Allowance, for TW Patent App. No. 95142312, Feb. 11, 2014.
Dec. 20, 2013 USPTO Non-Final Office Action dated Dec. 20, 2013 for U.S. Appl. No. 13/520,021.
Apgar et al., "The Bethesda System Terminology." Am Fam Physician 2003; 68: 1992-1998.
Kovanda et al., "Characterization of a Novel Cutanous Human Papillomavirus Genotype HPV-125." PLosOne 2011; vol. 6 e22414Vol.
Narechania et al., "Phylogenetic incongruence among Oncogenic Genital Alpha Human Papillomaviruses." J. Virol. 2005, 79(24): 15503.
Rudikoff et al., "Single amino acid substitution altering antigen-binding specificity." Proc. Natl. Acad. Sci 1982 vol. 79 1979-1982.
Liu et al., "Fixed-cell immunoperoxidase Technology." China Academic Journal, Production Technology. 1993 vol. 23 No. 2 pp. 37-38.
Taiwan Patent Office Communication dated Oct. 7, 2013 for Application No. 098119612.
European Patent Office Communication dated Oct. 28, 2013 for Application No. 12164498.3-1404.
Sep. 18, 2013 USPTO Non-Final Office Action for U.S. Appl. No. 12/456,053.
Sep. 30, 2013 USPTO Non-Final Office Action for U.S. Appl. No. 12/456,054.
Sep. 30, 2013 USPTO Final Office Action for U.S. Appl. No. 12/590,747.
Sep. 16, 2013 Response to USPTO Final Office Action dated May 14, 2013 for U.S. Appl. No. 12/456,054.
Sep. 16, 2013 Declaration to USPTO Final Office Action dated May 14, 2013 for U.S. Appl. No. 12/456,054.
Non-final Office action for U.S. Appl. No. 11/559,366 dated Dec. 5, 2008.
Final Office action for U.S. Appl. No. 11/559,366 dated May 5, 2009.
Notice of Allowance for U.S. Appl. No. 11/559,366 dated Jan. 4, 2010.
Non-final Office action for U.S. Appl. No. 12/082,740 dated Jun. 12, 2009.
Final Office action for U.S. Appl. No. 12/082,740 dated Aug. 20, 2010.
Notice of Allowance for U.S. Appl. No. 12/082,740 dated Mar. 8, 2011.
Non-final Office action for U.S. Appl. No. 12/456,053 dated May 31, 2011.
Non-final Office action for U.S. Appl. No. 12/456,054 dated Aug. 17, 2011.
Non-final Office action for U.S. Appl. No. 12/456,055 dated Jul. 22, 2011.
EPO Communication for App. No. 09762928.1-1223/2300824, dated Aug. 15, 2011.
Extended European Search Report for App. No. 09762928.1-1223/2300824, dated Jul. 22, 2011.
EPO Communication for App. No. 06846299.3-2402/1951915, dated Apr. 7, 2010.
Extended European Search Report for App. No. 06846299.3-2402/1951915, dated Jan. 8, 2010.
International Search Report for Int'l App. No. PCT/US2009/003537, dated Oct. 8, 2009.
International Search Report for Int'l App. No. PCT/US2009/003538, dated Oct. 15, 2009.
International Search Report for Int'l App. No. PCT/US2010/033944, dated Jul. 2, 2010.
International Preliminary Report on Patentability for Int'l App. No. PCT/US2009/003538, dated Dec. 14, 2010.
International Preliminary Report on Patentability for Int'l App. No. PCT/US2009/003537, dated Dec. 14, 2010.
Written Opinion of the International Searching Authorigy for Int'l App. No. PCT/US2009/003538, dated Oct. 15, 2009.
Written Opinion of the International Searching Authorigy for Int'l App. No. PCT/US2009/003537, dated Oct. 8, 2009.
Written Opinion of the International Searching Authorigy for Int'l App. No. PCT/US2010/033944, dated Jul. 2, 2010.
International Search Report for Int'l App. No. PCT/US2010/060765, dated Mar. 25, 2011.
Written Opinion of the International Searching Authorigy for Int'l App. No. PCT/US2010/0060765, dated Mar. 25, 2011.
International Search Report for Int'l App. No. PCT/US2006/60883, dated Jul. 18, 2007.
International Preliminary Report on Patentability for Int'l App. No. PCT/US2006/60883, dated Jul. 18, 2007.
Written Opinion of the International Searching Authority for Int'l App. No. PCT/US2006/60883, dated Jul. 18, 2007.
EPO Communication for App. No. 06846299.3-2401, dated Oct. 21, 2011.
Final Office action for U.S. Appl. No. 12/456,055 dated Jan. 6, 2012.
Final Office action for U.S. Appl. No. 12/456,053 dated Nov. 17, 2011.
Non-final Office action for U.S. Appl. No. 12/589,692 dated Feb. 7, 2012.
Non-final Office action for U.S. Appl. No. 12/589,641 dated Feb. 6, 2012.
Non-final Office action for U.S. Appl. No. 12/456,076 dated Feb. 9, 2012.
Advisory action for U.S. Appl. No. 12/456,053 dated Jan. 26, 2012.

(56) References Cited

OTHER PUBLICATIONS

Advisory action for U.S. Appl. No. 12/082,740 dated Nov. 3, 2010.
Berumen et al., 2001 Asian-American Variants of Human Papillomavirus 16 and Risk for Cervical Cancer: a Case Control Study. Journal of the National Cancer Institute, vol. 93, No. 17.
Bleul et al., 1991 Human Papillomavirus Type 18 E6 and E7 Antibodies in Human Sera: Increased Anti-E7 Prevalence in Cervical Cancer Patients. Journal of Clinical Microbiology, Aug. 1991, pp. 1579-1588.
Bosch et al, 2002 Te Causal Relation between Human Papillomavirus and Cervical Cancer. J. Clinical Pathology, vol. 55, pp. 244-265.
de Villiers 1997. Papillomavirus and HPV typing. Clin. Dermatol 15:199-206.
Zur Hausen 2002. Papillomavirus and cancer: from basic studies to clinical pplication. Nat. rev. Cancer 2: 342-350.
Kreimer, et al. 2005. HPV 16 semiquantitative viral load and serological biomarkers in oral and oropharyngeal squamous cell carcinomas. Int J Cancer 115: 329-32.
Nair, Pillai 2005 Human papillomavirus and disease mechanisms: relevance to oral and cervical cancers Oral Diseases 11, 350-359.
Nindl, et al. 1994. Antibodies against linear and conformational epitopes of the human papillomavirus (HPV) type 16 E6 and E7 oncoproteins in sera of cervical cancer patients. Arch. Virol. 137:341-353.
Sasagawa, et al. 2003. Mucosal immunoglobulin-A and -G responses to oncogenic human papilloma virus capsids. Int J Cancer. Apr. 10, 2003; 104(3): 328-35.
Snijders, et al. 2006 HPV-mediated cervical carcinogenesis: concepts and clinical implications J Pathol 2006; 208: 152-164.
Stacey, et al. "Expression of human papillomavirus type 16 E6 protein by recombinant baculovirus and use for detection of anti-E6 antibodies in human sera", Journal of General Virology vol. 73, pp. 2337-2345, date Sep. 1992.
Stoppler, et al. 1996 Natural Variants of the Human Papillomavirus Type 16 E6 Protein Differ in Their Abilities to Alter Keratinocyte Differentiation and to Induce p53 Degradation. Journal of Virology, p. 6987-6993 vol. 70, No. 10.
Tornesello, et al. 2004 Analysis of human papillomavirus type-16 variants in Italian women with cervical intraepithelial neoplasia and cervical cancer J Med Virol.; 74(1): 117-26.
Viscidi, et al. 1993. Serologic response in human papillomavirus-associated invasive cervical cancer. Int. J. Cancer 55:780-784.
Lehtinen, et al.2001. Human papillomavirus infection, risk for subsequent development of cervical neoplasia and associated population attributable fraction. J Clin Virolo 22:117-124.
Mougin, et al. 2001. Epidemiology of cervical papillomavirus infections. Recent knowledge. Press Med 30: 1017-23.
Santer et el., 2007 Carcinogenesis, vol. 28 No. 12 pp. 2511-2520. "Human papillomavirus type 16 E7 oncoprotein inhibits apoptosis mediated by nuclear insulin-like growth factor-binding protein-3 by enhancing its ubiquitin/proteasome-dependent degradation."
Zhao et al., 2013 Cancer Prevention Research. Published OnlineFirst Jul. 22, 2013. "An Evaluation of Novel, Lower-Cost Molecular Screening Test for Human Papillomavirus in Rural China."
Shi et al., 2009 American Journal of Epidemiology vol. 170 No. 6. 708-716. "Human papillomavirus testing for cervical cancer screening: results from a 6-year prospective study in rural China."
Belinson et al., Am J. Clin Pathol 2011; 135:790-795. "A population-based clinical trial comparing endocervical high-risk HPV testing using hybrid capture 2 and Cervista from the SHENCCAST II study."
Dockter et al., 2009 Journal of Clinical Viroogy 45, 51: 539-547. "Analytical characterization of the APTIMA HPV assay."
Wong et al., 2011 Journal of Clinical Virology 51 (2011) 136-138. "Efficacy of Abbott real time high risk HPV test in evaluation of atypical squamous cells of undetermined significance from and Asian screening population."
Branca et al., 2005 Am J Clin Pathol 124: 113-121. "Survivin as a marker of cervical intraepithelial neoplasia and high-risk human papillomavirus and a predictor of virus clearance and prognosis in cervical cancer."
Branca et al., 2006 J Clin Pathol 59: 40-47. "Aberrant expression of VEFG-C is related to grade of cervical intraepithelial neoplasia (CIN) and high risk HPV but does not predict virus clearance after treatment of CIN or prognosis of cervical cancer."
Lambert et al., 2006 Experimental and Molecular Pathology 80: 192-196. "p16INK4A expression in cervical premalignant and malignant lesion."
Giannoudis et al., 2000 British J. Cancer 81:424-7. "Differential expression of p53 and p21 in low grade cervical squamous intraepithelial lesions infected with low, intermediate, and high risk human papillomaviruses."
Saqi et al., 2002 "Overexpression of p16INK4A in liquid-based specimens (SurePath) as marker of cervical dysplasia and neoplasia." 27: 365-370.
Park et al., 1998 "HPV-16-releated proteins as the serologic markers in cervical neoplasis." Gynecologic oncology 69, 47-55.
Lie et al., 1999 Int J Gynecol Pathol 18(1): 5-11."Expression of p53, MDM2, and p21 proteins in high-grade cervical intraepithelial neoplasia and relationship to human papillomavirus infection."
Aug. 30, 2013 EPO Office communication for EPA No. 09762928.1.
Sep. 9, 2013 USPTO Communication for U.S. Appl. No. 13/520,021.
Fiedler et. al., 2004 FASEB Journal express article. High Level HPV-16 E7 oncoprotein expression correlates with reduced pRb-levels in cervical biopsies.
US Patent Office non-final Office action for U.S. Appl. No. 13/319,312, Feb. 28, 2014.
China Patent Office communication for CN Patent App. No. 200980131078.4, Feb. 12, 2014.
Pillai et al., Cancer Epidemiology Biomarkers & Prevention 1996; 5: 329-335. "The presence of human papillomavirus-16/-18 E6, p53, and Bcl-2 protein in cervicovaginal smears from patients with invasive cervical caner".
Pavai et al., Romanian Journal of Morphology and Embryology 2006, 47(3): 229-234. "Comparative detection of high-risk HPV (16, 18, 33) in ervical bioptic material of County Hospital of Tg. Mures."
Non-final Office action for U.S. Appl. No. 12/456,053 dated Apr. 6, 2012.
Final Office action for U.S. Appl. No. 12/456,054 dated Apr. 16, 2012.
Park T W, fujiwara H, Wright T C. 1995. Molecular biology of cervical cancer and its precursors. Cancer 76: 1902-13.
Wang H L, Lu D W. 2004. Detection of human papillomavirus DNA and expression of p16, Rb, p53 proteins in small cell carcinomas of the uterine cervix. Am J Surg Pathol. 28:, p. 901-908.
Walboomers J M, Meichers W J, Manos M M, et al. 1999. Human papilomavirus is a necessary cause of invasive cervical cancer worldwide. J Pathol. 189:12-19.
de Villiers E. M. 1997. Papillomavirus and HPV typing. Clin. Dermatol 15:199-206.
Zur Hausen, H. 2002. Papillomavirus and cancer: from basic studies to clinical application. Nat. rev. Cancer 2: 342-350.
Parkin D M, Pisant P and ferlay J. 1993. Estimates of the worldwide incidence of eighteen major cancers in 1985. Int J Cancer 54:594-606.
Solomon D, Davey R, Kurman R A, et al. 2002. The 2001 Bethesda Systems. Terminology for reporting results of cervical cytology. JAMA 287:2114-19.
Guimaraes M C, Goncalves M A, Soares C P, et al. 2005. Immunohistochemical expression of p16INK4a and bcl-2 according to HPV type and to the progression of cervical squamous.
Sasagawa T, Rose RC, Azar KK, Sakai A, Inoue M. 2003. Mucosal immunoglobulin-A and -G responses to oncogenic human papilloma virus capsids.Int J Cancer. Apr. 10, 2003;104(3):32, Intraepithelial Lessions. J. Histochem Cyto, 53, p. 509.
Sun, et al., Comparison of Peptide Enzyme-Linked Immunosorbent Assay and Radioimmunoprecipitation Assay with in Vitro-Translated Proteins for Detection of Serum Antibodies to Human Papillomavirus Type 16 E6 and E7 Proteins, J. Clin. Microbiol, 1994, p. 2216-2220).

\* cited by examiner

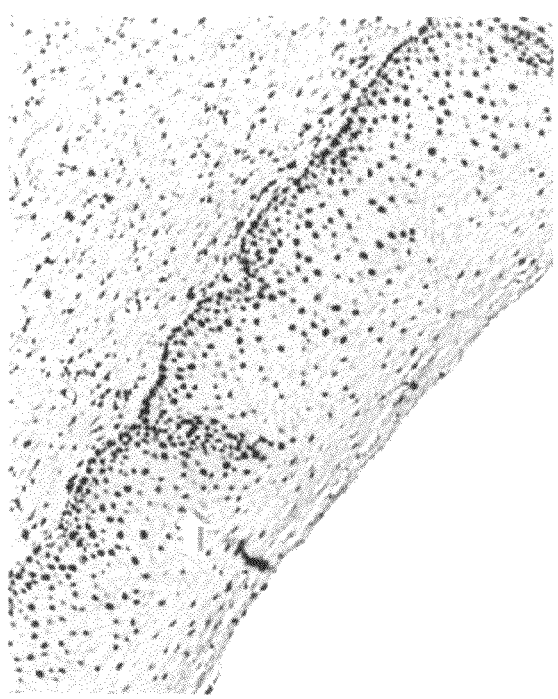
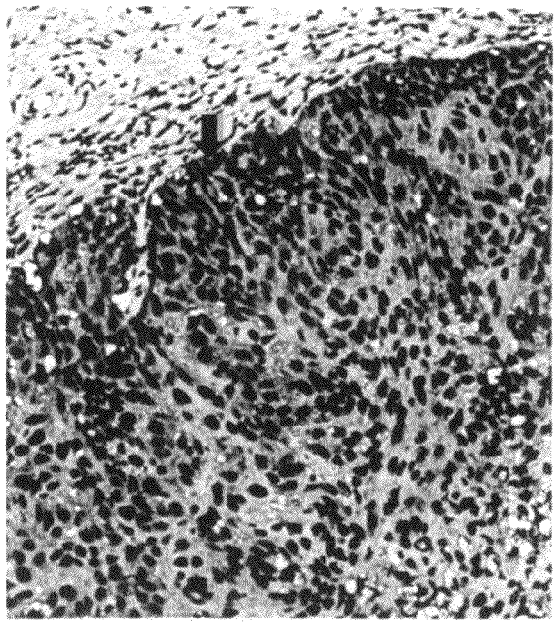
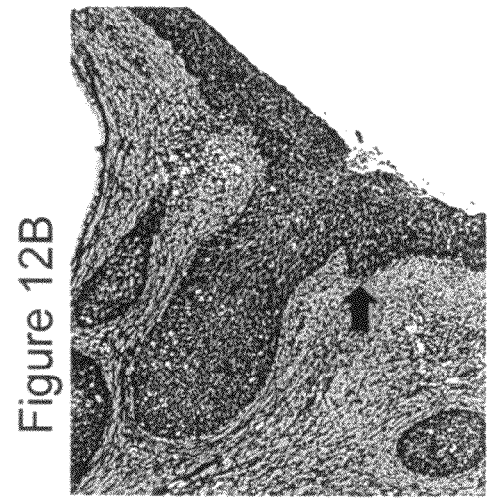
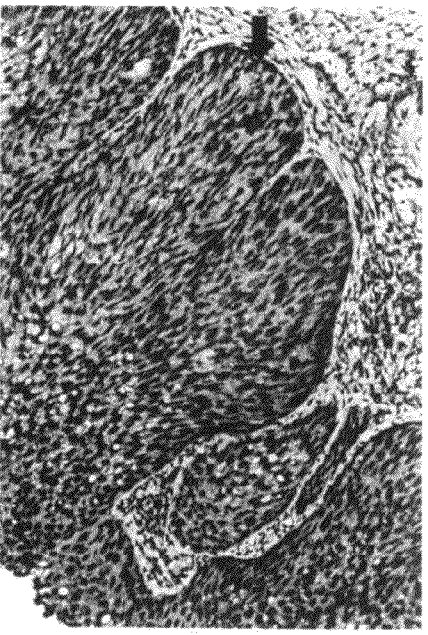
Figure 12A
Figure 12B
Figure 12C
Figure 12D

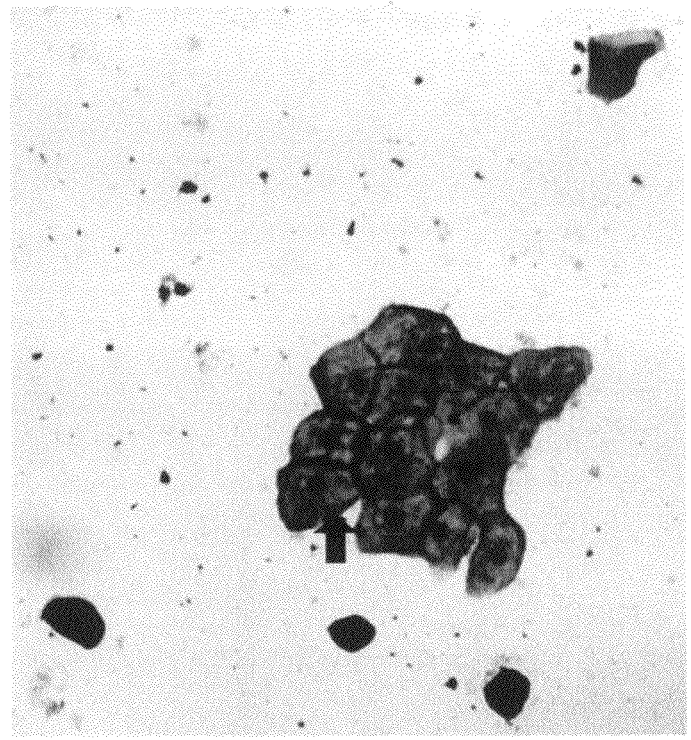
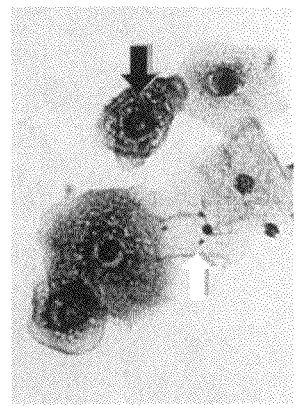
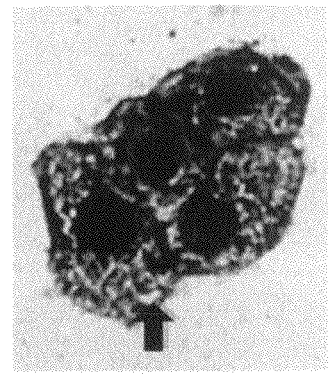
Figure 14C
Figure 14B
Figure 14A

MONOCLONAL ANTIBODIES AGAINST HPV PROTEINS

CROSS-REFERENCE TO RELATED APPLICATIONS

This application claims benefit of U.S. provisional patent application Ser. No. 61/131,991, filed Jun. 13, 2008, and U.S. provisional patent application Ser. No. 61/192,912, filed Sep. 22, 2008. Each of the aforementioned related patent applications is herein incorporated by reference.

BACKGROUND OF THE INVENTION

Infection by human papillomaviruses (HPV) at specific epithelium cells to induce epithelial proliferations plays an important role for cervical carcinogenesis. About 99 percent of confirmed cervical cancer cases are found to be associated with HPV infection with biopsy-confirmed squamous intraepithelial lesions (SIL) or cervical intraepithelial neoplasia (CIN). The incidence of HPV infection, primarily transmitted through sexual contact, is highest among young women and about 20 million sexually active men and women worldwide are currently infected. Approximately 1% of the population has genital warts and 4% of women have cervical precancerous lesions, such low grade of squamous intraepithelial lesion (LSIL), high grade of squamous intraepithelial lesion (HSIL) or atypical squamous cells of undetermined significance (ASCUS).

The presence of these lesions, preferentially observed in women aged 35-40 yrs, are at high risk of progression toward invasive cervical cancer. It is generally thought that persistent infection of human papillomavirus (HPV) is essential for developing precancerous epithelial lesions. Infections of high-risk types of HPV in women with LSIL may or may not progress to HSIL. In fact, remission occurs in the majority of LSIL human subjects while some progress to HSIL. Although 99.7% of cervical cancers are HPV positive, integration of viral genome into the host genome is required to facilitate the necessary genes to express for developing into HSIL or cancer. In fact, only one in every 10 women with persistent HPV infection may develop into higher grades of CIN lesions, such as cervical intraepithelial neoplasia (CIN) grade 2 and grade 3 (CIN2, and CIN3, respectively), and a portion of these epithelial lesion cases may ultimately progress into cervical cancer.

In the past, screening for cervical cancer is based on conventional cytology by papanicolaou (Pap) smear and suspicious smears are followed up with colposcopy, and/or histological biopsy. The use of cytological screening leads to a remarkable reduction in the mortality of cervical cancer. However, due to subjective test criteria, drawbacks of pap smear tests include difficulty in obtaining samples, poor inter- and intra-observer agreement, a high rate of false negatives (up to 20%) and false positives, the requirements for specialized labs staffed with highly trained personnel, and inability to identify a large proportion of HPV-infected persons. More reproducible assays are needed to improve the current screening method to avoid unnecessary medical intervention and psychological distress for the affected women. The current cervical cytology screening has sensitivity ranged from 30% to 87% and specificity ranged from 86% to 100%.

Detecting HPV infection by nucleic acid methods, such as "DNA Hybrid Capture", has been developed, but is not ideal, due to not only its high cost, assay operation procedures, the requirements for facility, equipment, and highly trained personnel, but also its very low positive predictive value to CIN. In addition, DNA testing could not differentiate the diagnosis of LSIL from HSIL, nor CIN lesions from non-transforming latent or remissive viral infection. What is needed is a low cost, simple, sensitive and specific assay that can be performed on routine practice of a clinical lab or doctor office and is capable of detecting early stage of epithelial lesions, distinguishing LSIL from HSIL, and predicting the risk of progression into cervical cancer. Assays like PreTect HPV-Proofer® for the detection of E6/E7 mRNA suggested equivalent sensitivity to HPV DNA testing with higher positive predictive value. However, there are limited reports showing direct detection of E6/E7 oncoproteins in situ.

Known protocols for producing monoclonal antibodies are generally unsuitable for the production of anti-HPV monoclonal antibodies and cannot be used in immunocytochemical diagnostic tests for screening general human population. This is because antibodies produced by these protocols will not necessarily react with the naturally occurring HPV viral proteins in infected human cells. In addition, the epitopes recognized by prior antibodies will not necessarily be those epitopes which are resistant to the harsh procedures involved in standard sampling, fixing and storing of clinical specimens.

Three problems exist such that there is no antibody available to do clinical HPV detection. One is that HPV proteins in clinical samples are present in very small quantities. Secondly, there are too many HPV types and most HPV types present in clinical samples are not known or systemically identified due to the lack of available antibodies. Third, HPV virus can not be cultured in labs by standard tissue culture techniques. Therefore, there are no avaialbe HPV proteins purified in large quantities as immunogens for generating anti-HPV antibodies, and there are no available HPV proteins or antibodies as binding agents for clinical HPV detection.

Only 15 out of more than 100 types of HPV infections are considered to have a high risk of developing into CIN or cervical cancer. Also, around 70% of cervical cancer cases and 50% of CIN 2 and CIN 3 cases are attributed to high risk HPV type-16 and HPV type-18 infections. However, some progressive cervical cancer cases are related to infection by low risk HPV types, while infection of some HPV types will never progress into cervical cancer. For those reasons, it is important to identify those HPV infections with particular oncogenic proteins expression rather than just identify high risk types of HPV infection. Thus, there is a need for identifying HPV oncoproteins as cervical cancer biomarkers to better predict the risk of developing HSIL or cervical cancer-related diseases.

The development of appropriate assays, such as HPV immunoassays, is needed for the detection of such HPV oncoproteins or biomarkers for cervical cancer. The presence of E6/E7 oncoproteins in CIN 2 and CIN3 lesions could be evidence to indicate a high risk of progression. However, there are limited antibodies available for the detection of E6/E7 oncoproteins in situ. Therefore, there is a need to develop antibodies and assays for detecting HPV oncoproteins as cervical cancer biomarkers and screening for invasive cervical cancer and/or the risk for malignant transformation into cervical cancer.

SUMMARY OF THE INVENTION

Embodiments of the invention generally relate to various methods, detection assays, kits, polyclonal and monoclonal antibodies, polypeptides, recombinant proteins, and nucleic acids useful for detecting HPV infection, including general HPV infection as well as infection by various HPV genotypes, high risk HPVs and low risk HPVs. Various novel monoclonal antibodies against HPV proteins, useful as biomarkers and useful tools for detecting HPV viral proteins, HPV oncoproteins, early screening of cervical cancer, and diagnosing CIN, dysplasia stages, and/or invasive cervical and other cancers, are provided. The tools of the inventions can also be used in early clinical detection of HPV infection and general diagnosis for cervical cancer and other cancers, specific detection of invasive cervical cancer, detection of other HPV related cancers, early stage precancerous lesions as well as late stage cancer progression.

Methods of producing the monoclonal antibody are provided herein to obtain monoclonal antibodies recognizing one or more common epitopes of HPV proteins among various HPV proteins or HPV types. In addition, some of the monoclonal antibodies obtained herein are HPV type-specific, while some of the monoclonal antibodies obtained herein are non-HPV type-specific. The non-HPV type-specific antibodies recognize most of the prevalent HPV types present in clinical samples. As a result, these monoclonal antibodies are suitable to be used in an assay to detect HPV infection in one or more clinical samples.

The various HPV associated antibodies may include polyclonal and monoclonal antibodies which show specificity for one or more HPV proteins encoded by early genes and/or late genes from one HPV genotype or two or more genotypes. The one, or two, or more antibodies described herein can be used to perform immunoassays for different human subjects for comparison with positive and negative controls.

One embodiment of the invention provides a monoclonal antibody obtained by screening antibody-producing hybridoma cells with two or more purified recombinant human papillomavirus viral proteins. The screening step includes selecting the antibody-producing hybridoma cells with positive reactivity to the two or more purified recombinant papillommavirus proteins and with negative reactivity to non-HPV proteins, such that the antibody-producing hybridoma cells generate the monoclonal antibody with binding specificity to two or more human papillomavirus viral proteins. In one embodiment, a monoclonal antibody is obtained by screening antibody-producing hybridoma cells with a first purified recombinant human papillomavirus protein from a first HPV type and a second purified recombinant human papillomavirus protein from a second HPV type such that the monoclonal antibody is capable of recognizing a common epitope on human papillomavirus viral proteins from the same or different HPV types. In another embodiment, a monoclonal antibody, obtained by screening antibody-producing hybridoma cells with a first purified recombinant human papillomavirus protein from a first HPV type and a second purified recombinant human papillomavirus protein from a second HPV type such that the monoclonal antibody is capable of recognizing a specific epitope on only one of the first and the second purified recombinant human papillomavirus proteins and not the other purified recombinant human papillomavirus protein, is provided.

In another embodiment, a monoclonal antibody capable of binding to two or more HPV viral proteins from the same HPV type is provided and obtained by screening antibody-producing hybridoma cells with two or more purified recombinant papillomavirus proteins. The two or more purified recombinant papillomavirus proteins can be from the same HPV type and/or from different HPV types, such that the antibody-producing hybridoma cells generate the monoclonal antibody with binding specificity to two or more human papillomavirus viral proteins from the same types. The two or more purified recombinant papillomavirus proteins can be two or more purified recombinant papillomavirus early proteins such that the monoclonal antibody is capable of binding to two or more HPV early proteins corresponding to the two or more purified recombinant papillomavirus early proteins. The two or more purified recombinant papillomavirus proteins comprises a purified recombinant papillomavirus early protein and a purified recombinant papillomavirus late protein such that the monoclonal antibody is capable of binding to an early viral protein and a late viral proteins corresponding to the purified recombinant papillomavirus early protein and the purified recombinant papillomavirus late protein.

In another embodiment, a monoclonal antibody capable of binding to two or more HPV viral proteins from different HPV types is provided. Such a monoclonal antibody is obtained by screening antibody-producing hybridoma cells with two or more purified recombinant papillomavirus proteins, wherein the screening step includes selecting the antibody-producing hybridoma cells with positive reactivity to the two or more purified recombinant papillommavirus proteins from different HPV types and with negative reactivity to non-HPV proteins, such that the antibody-producing hybridoma cells generate the monoclonal antibody with binding specificity to the two or more HPV viral proteins.

In still another embodiment, a monoclonal antibody capable of binding to an early HPV viral protein and a late HPV viral protein from different HPV types is provided. In yet another embodiment, a monoclonal antibody capable of binding to only a first HPV viral protein, but not a second HPV viral protein different from the first HPV viral protein, and obtained by screening antibody-producing hybridoma cells with positive reactivity to a first purified recombinant papillomavirus protein from a first HPV type and with negative reactivity to a second purified recombinant papillomavirus protein from a second HPV type, wherein the first and second viral proteins correspond to the first and the second purified recombinant papillomavirus proteins of the first and second HPV types.

SUMMARY OF DRAWING

FIG. 12A shows the representative staining image of the dysplasia cells of CIN2 tissues using an anti-E6 monolonal antibody in an immunohistocytostaining (IHC) assay.

FIG. 12B shows the representative staining image of the normal epithelium adjacent to the dysplasia tissue of the CIN2 sample in FIG. 12A.

FIG. 12C shows the representative staining image of the dysplasia epithelium of a CIN3 sample stained by the same anti-E6 monolonal antibody as used in FIG. 12A in an IHC assay, demonstrating specific IHC staining in the nuclear and cytoplasm of dysplasia cells by the anti-E6 monoclonal antibody.

FIG. 12D shows the representative staining image of the dysplasia epithelium of another CIN3 sample stained by the same anti-E6 monolonal antibody as used in FIG. 12A in an IHC assay.

FIG. 14A shows the representative staining image of cervical cells from a CIN2 cervical scrape sample prepared by thin prep and stained by a mouse monoclonal anti-HPV E7 antibody in an immunocytochemistry (ICC) assay.

FIG. 14B shows the representative staining image of cervical cells from a CIN3 cervical scrape sample prepared by thin prep and stained by a mouse monoclonal anti-E6 antibody in an ICC assay.

FIG. 14C shows the representative image of cervical cells from an adenocarcinoma (ADC) cervical scrape sample prepared by thin prep and stained by the same anti-E6 antibody shown in FIG. 14B in an ICC assay.

DETAILED DESCRIPTION

Figure 1A:
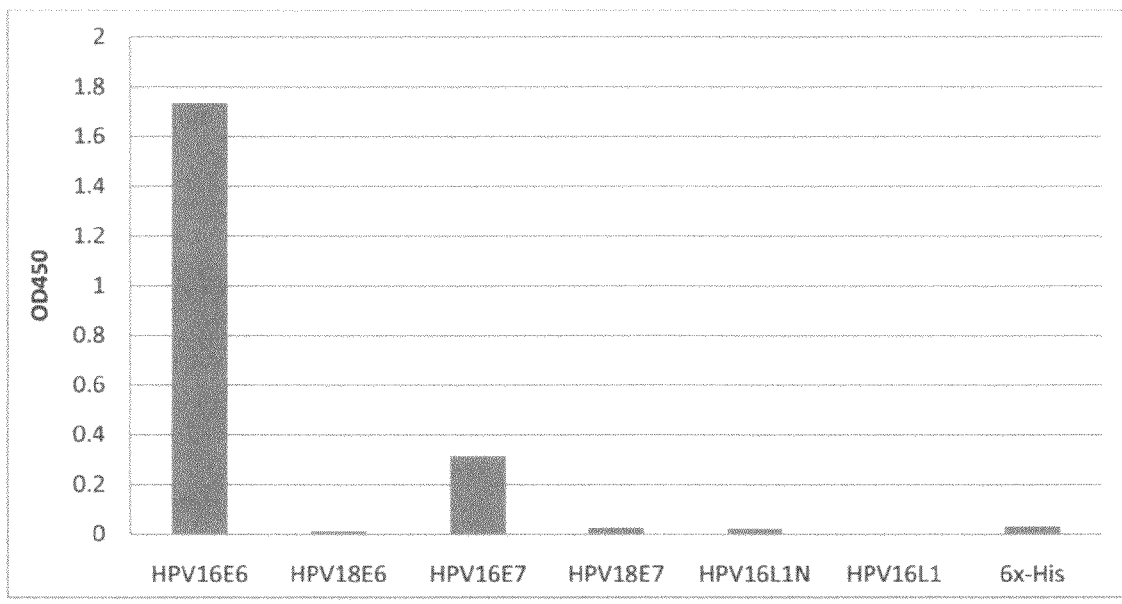
FIG. 1A shows the specificity of a monoclonal antibody capable of reacting with both HPV16 E6 and HPV16 E7 recombinant proteins (different HPV proteins from the same HPV type) and recognizing a common epitope on the different HPV16 E6 and HPV16 E7 proteins from the same HPV 16 type as assayed on EIA (enzyme immuno assays) according to one embodiment of the invention.

Embodiments of the invention provide various monoclonal antibodies against HPV proteins such that infection by high risk and low risk HPV types can be detected by a single monoclonal antibody. The invention also provides HPV type-specific monoclonal antibodies for detecting only the high risk HPV types. In addition, monoclonal antibodies highly specific for a single HPV protein are also provided.

One aspect of the invention provides a method of producing monoclonal antibodies. The method includes obtaining various purified recombinant papillomavirus proteins and screening antibody-producing hybridoma cells with two or more purified recombinant papillomavirus proteins to obtain a monoclonal antibody capable of recognizing a common epitope on the two or more purified recombinant human papillomavirus proteins and binding to the two or more purified recombinant papillomavirus proteins and corresponding papillomavirus viral proteins in biological and clinical samples.

In addition, the monoclonal antibody with binding specificity to two or more human papillomavirus viral proteins is produced by using a method which includes positive selection of the antibody-producing by bridoma cells with two or more purified recombinant papillommavirus proteins and negative selection of the antibody-producing hybridoma cells with non-HPV proteins. For example, the method may include screening antibody-producing hybridoma cells with two or more purified recombinant papillomavirus proteins by selecting the antibody-producing hybridoma cells with positive reactivity to the two or more purified recombinant papillommavirus proteins and with negative reactivity to non-HPV proteins, such that the antibody-producing hybridoma cells generate the monoclonal antibody with binding specificity to the two or more human papillomavirus viral proteins. The two or more purified recombinant papillomavirus proteins may include, for example, HPV 16 E6 protein, HPV 16 E7 protein, HPV 16 L1 protein, HPV 18 E6 protein, HPV18 E7 protein, HPV 18 L1 protein, and combinations thereof.

Another method of the invention includes screening antibody-producing hybridoma cells with a first purified recombinant human papillomavirus protein from a first HPV type and a second purified recombinant human papillomavirus protein from a second HPV type to obtain a monoclonal antibody capable of recognizing a common epitope on human papillomavirus proteins from two or more different HPV types. Still, another method of the invention provides screening antibody-producing hybridoma cells with a first purified recombinant human papillomavirus protein from a first HPV type and a second purified recombinant human papillomavirus protein from a second HPV type to obtain a monoclonal antibody capable of recognizing a specific epitope on only one of the first and the second purified recombinant human papillomavirus proteins and not the other purified recombinant human papillomavirus proteins.

For example, a monoclonal antibody capable of binding to two or more HPV viral proteins from the same HPV type is produced by the method of the invention by screening antibody-producing hybridoma cells with two or more purified recombinant papillomavirus proteins from the same HPV type and/or from different HPV types. In one example, the two or more purified recombinant papillomavirus viral proteins are two or more purified recombinant papillomavirus early proteins such that a monoclonal antibody is produced and is capable of binding to two or more HPV early proteins corresponding to the two or more purified recombinant papillomavirus early proteins. In another example, the two or more purified recombinant papillomavirus proteins may include a purified recombinant papillomavirus early protein and a purified recombinant papillomavirus late protein such that another monoclonal antibody is produced and is capable of binding to an early viral protein and a late viral proteins corresponding to the purified recombinant papillomavirus early protein and the purified recombinant papillomavirus late protein.

Exemplary monoclonal antibodies obtained include a type of monoclonal antibody capable of binding to both HPV16 E6 and HPV16 E7 viral proteins; another type of monoclonal antibody capable of binding to all HPV16 E6, HPV16 E7, and HPV16 L1 viral proteins; and anther type of monoclonal antibody capable of binding to both HPV18 E6 and HPV18 E7 viral proteins. Accordingly, the monoclonal antibody produced using methods of the invention is capable of binding to the two or more HPV viral proteins from the same HPV type selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof.

These monoclonal antibodies can be used for one or more immunological assays to detect HPV infection and HPV-related cervical cancer and other diseases. The suitable immunological assay may include ELISA (enzyme linked immunoabsorbant assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochemistry for tissues and/or cervical cells, and immunocytochemistry assays followed by flow cytometry.

Another aspect of the invention provides a method and a monoclonal antibody capable of binding to two or more HPV viral proteins from different HPV types. The monoclonal antibody is obtained by screening antibody-producing hybridoma cells with two or more purified recombinant papillomavirus proteins by selecting the antibody-producing hybridoma cells with positive reactivity to the two or more purified recombinant papillommavirus proteins from different HPV types and with negative reactivity to non-HPV proteins, such that the antibody-producing hybridoma cells generate the monoclonal antibody with binding specificity to the two or more HPV viral proteins. Exemplary monoclonal antibodies include a type of monoclonal antibody capable of binding to HPV16 E7 and HPV18 E7 proteins; another type of monoclonal antibody capable of binding to HPV16 E6 and HPV18 E6 proteins; and another type of monoclonal antibody capable of binding to HPV16 L1 and HPV18 L1 proteins, among others, to be used for various immunological assays.

Still another aspect of the invention provides a monoclonal antibody capable of binding to an early HPV viral protein and a late HPV viral protein from different HPV types. The monoclonal antibody may be obtained by screening antibody-producing hybridoma cells with a purified recombinant papillomavirus early protein from one HPV type and a purified recombinant papillomavirus late protein from another HPV type, wherein the screening step includes selecting the antibody-producing hybridoma cells with positive reactivity to the purified recombinant papillomavirus early protein and the purified recombinant papillomavirus late protein, and with negative reactivity to non-HPV proteins, such that the monoclonal antibody generated from the antibody-producing hybridoma cells is capable of binding to the early HPV viral protein and the late HPV viral protein from different HPV types. The purified recombinant papillomavirus early protein may include HPV16 E6 protein, HPV16 E7 protein, HPV18 E6 protein, HPV18 E7 protein, and combinations thereof, and the purified recombinant papillomavirus late protein may include HPV16 L1 protein, HPV18 L1 protein, and combinations thereof. Exemplary monoclonal antibodies include a type of monoclonal antibody capable of binding to all HPV16 E6, HPV16 E7, HPV16 L1, HPV18 E6, and HPV18 E7 proteins; another type of monoclonal antibody capable of binding to all HPV16 E6, HPV16 E7, HPV16 L1, HPV18 E6, HPV18 E7, and HPV18 L1 proteins, among others. Such type of monoclonal antibody produced by the method of the invention can be used to detect the presence of any of these viral proteins in one or more immunological assays.

Still another aspect of the invention provides HPV type-specific monoclonal antibody capable of binding to only a first HPV viral protein, but not a second HPV viral protein different from the first HPV viral protein. Such a monoclonal-antibody may be obtained by screening antibody-producing hybridoma cells with positive reactivity to a first purified recombinant papillomavirus protein from a first HPV type and with negative reactivity to a second purified recombinant papillomavirus protein from a second HPV type, wherein the first and second viral proteins correspond to the first and the second purified recombinant papillomavirus proteins of the first and second HPV types. The HPV type-specific monoclonal antibody may be capable of binding to only one viral protein, the first viral protein. The first viral protein may include a viral protein from an HPV type selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof. Exemplary monoclonal antibodies include monoclonal antibodies recognizing only one viral protein selected from the group of HPV 16 E6 protein, HPV 16 E7 protein, HPV 16 L1 protein, HPV 18 E6 protein, HPV18 E7 protein, and HPV 18 L1 protein. Such type of monoclonal antibody produced by the method of the invention can be used to detect the presence of a specific viral protein in one or more immunological assays.

In one embodiment, the various recombinant papillomavirus proteins are purified from soluble fractions obtained after lysis of cells expressing the papillomavirus recombinant proteins such that they are soluble purified recombinant proteins. For example, the recombinant proteins may be purified into native folding in solution. As another example, the recombinant proteins are purified with buffers at pH values close to its pI or neutral pH or PBS buffers. As an example, the various recombinant papillomavirus proteins can be purified into its native folding by, e.g., dialysis in mild buffer solutions at neutral pH or in PBS buffer; concentrating by spin column or concentrators, etc., to maintain its solubility and obtain higher concentration. One method of purifying HPV recombinant proteins are described in co-pending U.S. patent application Ser. No. 11/559,366, filed on Nov. 13, 2006, titled "Detection method for human pappilomavirus (HPV) and its application in cervical cancer", which is incorporated by reference herein.

The sources of HPV proteins for making monoclonal antibodies are not limited; they can be various proteins from various HPV genes and from various HPV types/species. HPV viral protein and/or oncoproteins of the invention include, but are not limited to, HPV E6 proteins, HPV E7 proteins, HPV L1 proteins, HPV E2 proteins, HPV E3 proteins, HPV E4 proteins, HPV E5 proteins, HPV L2 proteins, among others. The HPV types are not limited. In general, HPV are divided into at least three groups: (1) the high risk HPV types, including α-papillomaviruses HPV-16, HPV-18, HPV-31, HPV-33, HPV-45, HPV-35, HPV-52, HPV-58, etc., which are oncogenic for cervical cancer and other cancers; (2) the low risk HPV types (including α-papillomaviruses HPV-6, HPV-11, HPV-13, HPV-34, HPV-44, HPV-55, HPV-73, HPV-27, PCPV1, HPV-2a, HPV-57, etc., which are at low risk for developing into cervical and other cancers; (3) other non-oncogenic α-papillomaviruses (such as HPV-66, HPV-68, HPV-53, HPV-51, HPV-59, HPV-30, HPV-26, HPV-10, HPV-28, HPV-32, HPV-39, HPV-3, HPV-29, HPV-70, etc.). Multiple HPV infection in a single human subject can be caused by two of more HPVs among the three HPV groups (high risk, low risk, and/or non-oncogenic).

Two problems exist such that there is no antibody available to do clinical HPV diagnostics. One is that HPV proteins in clinical sample are present in very small quantities. Secondly, the HPV types in the clinical sample are generally unknown. Therefore, people skilled in the art failed and were not able to produce large scale production of HPV antibodies that recognizes various clinical HPV types, despite this long felt need, and the need is not solved. For successful use of an antibody in a diagnostic test the antibody must recognize an epitope which is present on the immunogen and the epitope can be exposed in the test sample being prepared for analysis (i.e., exposed after any pre-treatment of tissues such as cryopreservation, sectioning and fixing). Therefore, the method chosen for screening large numbers of hybridoma culture supernatants must be such that it aids selection of diagnostically useful antibodies. There has been known failure in purifying and obtaining recombinant HPV proteins and in producing antibodies from purified recombinant proteins for detecting HPV infection and people have not been able to solve the need.

Methods of producing monoclonal antibodies against HPV proteins are provided herein to obtain one or more monoclonal antibodies. Each monoclonal antibody is capable of recognizing a common epitope or a specific epitope of HPV proteins among various HPV proteins and/or HPV types. In addition, some of the monoclonal antibodies obtained herein are HPV type-specific, while some of the monoclonal antibodies obtained herein are non-HPV type-specific. The non-HPV type-specific antibodies are useful to detect prevalent HPV types present in clinical samples. As a result, these monoclonal antibodies are suitable to be used in an assay detecting for HPV infection in one or more clinical samples. Epitope mapping of these non-HPV type specific antibodies identifies and allocates the common epitope of the HPV specific proteins for the binding of these monoclonal antibodies.

In one embodiment, a monoclonal antibody capable of recognizing a common epitope on two or more HPV viral proteins is obtained by screening antibody-producing hybridoma cells with two or more purified HPV recombinant proteins. The two or more purified HPV recombinant proteins may include any of the suitable HPV proteins, such as HPV 16 E6 protein, HPV 16 E7 protein, HPV 16 L1 protein, HPV 18 E6 protein, HPV18 E7 protein, HPV 18 L1 protein, and combinations thereof.

In another embodiment, the two or more HPV proteins correspond to the two or more purified recombinant papillommavirus proteins. For example, when the two or more HPV protein are E6 and E7 early proteins, a monoclonal antibody recognizing a common epitope on both E6 and E7 early proteins can be obtained by screening two or more purified E6 and E7 recombinant proteins from HPV16 and/or HPV 18, or another HPV type. In another embodiment, the two or more purified recombinant papillomavirus proteins are two or more recombinant HPV early proteins such that the monoclonal antibody is capable of recognizing a common epitope on HPV early proteins corresponding to the two or more purified recombinant HPV early proteins.

One embodiment of the invention provides a monoclonal antibody capable of recognizing a common epitope on both HPV16 E6 and HPV16 E7 early proteins by screening antibody-producing hybridoma cells with a purified HPV16 E6 recombinant protein and a purified HPV16 E7 recombinant protein. Another embodiment of the invention provides a monoclonal antibody capable of recognizing a common epitope on both HPV18 E6 and HPV18 E7 early proteins by screening antibody-producing hybridoma cells with a purified HPV18 E6 recombinant protein and a purified HPV18 E7 recombinant protein.

In another embodiment, the two or more purified recombinant papillomavirus proteins include a purified recombinant papillomavirus early protein and a purified recombinant papillomavirus late protein such that the monoclonal antibody is capable of recognizing a common epitope on early and late viral proteins corresponding to the purified recombinant papillomavirus early protein and the purified recombinant papillomavirus late protein. The purified recombinant papillomavirus early protein may be any of the early papillomavirus proteins from any of the papillomavirus types, such as HPV 16 E6 protein, HPV 16 E7 protein, HPV 18 E6 protein, HPV18 E7 protein, and combinations thereof. The purified recombinant papillomavirus late protein may be any of the late papillomavirus proteins, such as HPV16 L1 protein, HPV18 L1 protein, and combinations thereof. For example, a monoclonal antibody is obtained by screening with HPV16 E6, HPV16 E7, HPV16 L1, HPV18 E6, and HPV18 E7 proteins such that the monoclonal antibody recognizes a common epitope on HPV16 E6, HPV16 E7, and HPV16 L1 proteins.

In still another embodiment, the two or more purified recombinant papillomavirus proteins are two or more recombinant papillomavirus proteins from at least two different papillomavirus types. For example, a monoclonal antibody is obtained by screening antibody-producing hybridoma cells with a first purified recombinant papillomavirus protein from a first HPV type and a second purified recombinant papillomavirus protein from a second HPV type. The papillomavirus types can be any of the papillomavirus types, such as high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56. The first and the second purified recombinant human papillomavirus viral proteins may be, for example, HPV 16 E6 recombinant protein, HPV 16 E7 recombinant protein, HPV 16 L1 recombinant protein, HPV 18 E6 recombinant protein, HPV18 E7 recombinant protein, HPV 18 L1 recombinant protein, and combinations thereof.

Accordingly, one embodiment of the invention provides a monoclonal antibody capable of recognizing a common epitope on E6 protein from two different HPV types, both HPV16 and HPV18 by screening antibody-producing hybridoma cells with a purified HPV16 E6 recombinant protein and a purified HPV18 E6 recombinant protein. Another embodiment of the invention provides a monoclonal antibody that recognizes a common epitope on HPV16 E7 and HPV18 E7 proteins. Still another embodiment of the invention provides a monoclonal antibody that recognizes a common epitope on HPV16 E6, HPV16 E7, HPV16 L1, HPV18 E6, and HPV18 E7 proteins.

In still another embodiment, a monoclonal antibody capable of recognizing a specific epitope on only one HPV protein, but not another HPV protein is obtained by screening antibody-producing hybridoma cells with a first purified recombinant papillomavirus protein from a first HPV type and a second purified recombinant papillomavirus protein from a second HPV type, wherein the one and another viral proteins correspond to the first and the second purified recombinant papillomavirus proteins of the first and second HPV types.

One embodiment of the invention provides a monoclonal antibody obtained by screening antibody-producing hybridoma cells with a purified recombinant HPV16 E6 protein and a purified recombinant HPV18 E6 protein, such that the monoclonal antibody recognizes a specific epitope on HPV16 E6 protein and does not recognize or interact with HPV18 E6 protein. Another embodiment of the invention provides a monoclonal antibody obtained by screening antibody-producing hybridoma cells with a purified recombinant HPV16 E6 protein and a purified recombinant HPV18 E6 protein, such that the monoclonal antibody recognizes a specific epitope on HPV18 E6 protein and does not recognize or interact with HPV16 E6 protein.

Another embodiment of the invention provides a monoclonal antibody obtained by screening antibody-producing hybridoma cells with a purified recombinant HPV16 E7 protein and a purified recombinant HPV18 E7 protein, such that the monoclonal antibody recognizes a specific epitope on HPV16 E7 protein and does not recognize or interact with HPV18 E7 protein. Another embodiment of the invention provides a monoclonal antibody obtained by screening antibody-producing hybridoma cells with a purified recombinant HPV16 E7 protein and a purified recombinant HPV18 E7 protein, such that the monoclonal antibody recognizes a specific epitope on HPV18 E7 protein and does not recognize or interact with HPV16 E7 protein.

In another embodiment, various monoclonal antibodies against HPV proteins, E6, E7 or L1 (anti-HPV E6, anti HPV E7, anti-HPV-L1) are provided including those monoclonal antibodies specific for detecting HPV types correlated with the immunogens that the antibodies were raised, and other non-HPV type-specific monoclonal antibodies. The antibodies of the invention include, but are not limited to anti-E6, anti-E7, and anti-L1 antibodies, etc., and are used in one or more immunological assays. For examples, the monoclonal antibodies can be used to test on various biological samples, cell lines, and/or clinical samples of various grades of epithelial lesions (CIN2, CIN3, LSIL, HSIL, ASCUS) as well as different cervical cancers, squamous cell carcinoma (SCC, a type of common cancer) and adenocarcinoma (ADC, a type of gland cancer).

In one embodiment, a method of screening a human subject of papillomavirus infection includes obtaining a clinical sample from the human subject, and conducting one or more immunological assays on the clinical sample from the human subject using various HPV recombinant proteins and lab-generated antibodies specific for HPV proteins in order to detect and screen for the presence of HPV infection from the presence of HPV antibodies and HPV proteins in the human subject. In another embodiment, the HPV proteins in the human subject are detected using antibodies raised against HPV recombinant proteins, including but not limiting to various polyclonal and monoclonal antibodies against various HPV early and late proteins.

The antibodies as developed herein lend themselves to the high quality and properly purified recombinant proteins encoded by HPV early and late genes, useful in immunological assays to generate very high sensitivity and specificity for screening HPV infection and cervical cancer detection. The monoclonal antibody can be used for one or more immunological assays selected from the group consisting of ELISA (enzyme linked immunoabsorbant assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochemistry for tissues and/or cervical cells, and immunocytological assays followed by flow cytolmetry, among others. In one embodiment, the one or more immunological assays may be non-invasive with minimal or no additional instrument required.

The basic techniques for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art. The related immunological assays, immunohistochemistry for tissues and/or cervical cells, and/or immunocytological assays followed by flow cytolmetry can also be found in co-pending United State patent applications: U.S. application Ser. No. 11/559,366, filed on Nov. 13, 2006, titled "Detection method for human pappilomavirus (HPV) and its application in cervical cancer"; U.S. application Ser. No. 12/082,740, filed Apr. 14, 2008, titled "Protein chips for HPV detection"; U.S. App. Ser. No. 61/131,991, filed Jun. 13, 2008 titled "Antibodies and assays for HPV detection"; U.S. App. Ser. No. 61/192,912 Filed on Sep. 22, 2008, titled "Novel monoclonal antibodies against HPV proteins useful for early stage and late stage detection, screening, and diagnosis of HPV related cervical cancer"; U.S. application Ser. No. 12/456,054, filed concurrently as this application, titled "in situ detection of early stages and late stages HPV infection"; U.S. application Ser. No. 12/456,055, filed concurrently as this application, titled "in situ detection of early stages and late stages HPV infection"; U.S. application Ser. No. 12/456,076, filed concurrently as this application, titled "Detection of early statges and late stages HPV infection". All of the above referenced applications are herein incorporated by reference.

In one embodiment, the invention also provides various methods, detection assays, and kits, polyclonal and monoclonal antibodies, polypeptides, recombinant proteins, and nucleic acids useful for detecting general HPV infection as well as infection by various HPV genotypes, high risk HPVs and low risk HPVs. In addition, the assays or sample formats in detecting the presence of HPV proteins are not limited and can be used for cervical tissues, cervical cells, cervical scrapes, serum, body fluids, etc. The useful screening or diagnosing assay can be IHC, ICC, flow cytometry, antibodies coupled to beads, rapid tests, protein chips, dot blots, slots, as well a conventional ELISA assay. HPV proteins can be detected by the antibodies of the invention to be present in epithelium tissue as evidenced by IHC staining after scoring by a pathologist.

The antibodies described in this invention provide a tool to detect HPV proteins present in various sources of biological samples. As an example, the antibodies described herein can be used as capture antibody to coat on microtiterplate and/or used as detection antibody as a sandwich format of ELISA (Enzyme Linked Immuno Sandwich Assay). Depending on detection of HPV proteins and/or HPV types, antibodies can be selected for use based on the specificity described herein of monoclonal antibody to particular HPV proteins or HPV types, or in combinations thereof. The detection antibody from selected specificity of monoclonal antibodies described herein can be directly conjugated with label like biotin, alkaline phosphatase, HRP, fluorescent, etc., followed by color metric, chemiluminescent or fluorescent substrate for readout. The detection antibody can also select from polyclonal antibody described herein followed by a secondary antibody conjugated with a label like biotin, alkaline phosphatase, HRP, fluorescence, etc. Using a combination of polyclonal and monoclonal antibodies for the sandwich ELISA as capture and detection antibodies or vice versa, increases assay sensitivity by incorporating a secondary antibody to amplify the signal for detecting the binding. For direct EIA (Enzyme Immuno Assay), cells, samples or cultured cells to be tested were collected and lysed to generate cell lysate as analyte. The protein in the cell lysate was quantitated and coated to microtiterplate using the same amount of protein for coating of each sample in each well followed by the detection antibody with specificity described herein.

Detection of HPV DNAs, genomes, early viral proteins, late viral proteins, oncoproteins, and/or capsid proteins from various HPV genotypes can be performed by various in vitro and in vivo method and detection assays according to "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals and can be very useful in general clinical screening for HPV infection.

In addition, detection of HPV antibodies and/or oncoproteins by immunological assays can be used in general clinical screening for HPV infection and early diagnosis for cervical cancer and can be performed in a single rapid test or in multiplexed test. Comparative detection of altered levels of HPV proteins and host proteins can be performed in the same or different assays. It can also be used in diagnosing HPV-associated carcinomas of the uterine cervix, as well as those cases associated with epithelial cell abnormalities induced by HPV infection, pre-malignant and malignant HPV-associated epithelial cell lesions, and those at risk of developing HPV-associated cervical carcinoma and adenocarcinoma. The methods as described herein can be used independently or as an adjunct screening tool to convention cytological papanicolaou smear tests or histological tests and the results thereof can be compared for follow-up patient management.

The antibodies of the invention can be used in an immunological assay to detect a stage of disease caused by HPV infection. The disease stage may be, for example, an early stage HPV infection, a late stage HPV infection, an early stage cervical cell lesion, a late stage cervical cell lesion, low grade of squamous intraepithelial lesion (LSIL), high grade of squamous intraepithelial lesion (HSIL), atypical squamous cells of undetermined significance (ASCUS), cervical intraneoplasm stage 1, 2, 3 (CIN1, CIN2, CIN3, respectively), developed cervical cancer, adenocarcinoma (ADC), or squamous cell carcinoma (SCC).

EXAMPLES

1. Expression, Purification, and Preparation of HPV Recombinant Protein Used as Immunogens for Generating Antiserum, and Screening for Monoclonal Antibody from Hybridoma Cell Lines The method described in this Example can be applied to HPV recombinant proteins from any kinds of HPV proteins, HPV proteins of early genes or late genes, including, but not limited to, E2, E6, E7, L1, L2 and can be from various HPV types. One aspect of the invention provides recombinant proteins, such as recombinant hybrid proteins containing a partial sequence or a full length sequence of HPV oncogenic proteins. Examples include full-length E6, E7, and L1 polypeptide sequences, which have been found very difficult to obtain and purify due to undesirable aggregation during protein purification, protein instability, low levels of expression, and low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus are unsuitable as tools for clinical in vitro diagnostics.

1). Cloning and production of various recombinant proteins encoded by HPV16 E6 and HPV18 E6 gene. Cloning of an exemplary oncogenic E6 early gene from an exemplary HPV type, HPV-16 described herein a 474 base pair (b.p.) DNA fragment containing the 157 amino acid coding region of the HPV-16 E6 gene was obtained by polymerase chain reaction (PCR) amplification. The DNA sequence of the isolated DNA fragment was confirmed by comparing with the sequence from Gene Bank database. All cloning procedures were carried out according to the protocols described in "Molecular Cloning", A Laboratory Manual, eds. Sambrook, Fritsch and Maniatis, Cold Spring Harbor Laboratory Press, 1989. In addition, HPV18E6, fragments were also cloned and sequence confirmed.

2). Cloning and production of various recombinant proteins encoded by HPV16 E7 and HPV18 E7 gene. Cloning of an exemplary oncogenic E7 early gene from an exemplary HPV type, HPV-16, is described herein. A 294 base pair (b.p.) DNA fragment containing the 99 amino acid coding region of the HPV-16 E7 gene was obtained by polymerase chain reaction (PCR) amplification. The DNA sequence of the isolated DNA fragment was confirmed by comparing with the sequence from Gene Bank database. In addition, E7 DNA fragments from different strains of HPV-16 were also cloned from different clinical samples or sources.

3). Cloning and production of various recombinant proteins encoded by HPV16 L1 and HPV18 L1 gene. Cloning of an exemplary late gene from an exemplary HPV type, HPV-16, is described herein. A 1596 base pair (b.p.) DNA fragment containing the 531 amino acid coding region of the HPV-16 L1 gene was obtained by polymerase chain reaction (PCR) amplification. The DNA sequence of the isolated DNA fragment was confirmed by comparing with the sequence from Gene Bank database. In addition, L1 DNA fragments from different strains of HPV-16 were also cloned from different clinical samples or sources.

A recombinant N-terminal fragment of HPV 16 L1 protein was also obtained by expression in His-tagged expression system. The molecular weight of the HPV-16 L1 N-terminal recombinant protein is about 34 kD. C-terminal fragments can also be obtained. The same techniques were applied to produce recombinant HPV-18 L1 protein, and used as immunogens for generating antiserum, polyclonal and monoclonal antibodies.

The one or more recombinant proteins as described herein were expressed in various suitable systems, such as bacterial expression systems, viral expression systems, yeast expression systems, mammalian expression systems, e.g., in E. coli, yeast, baculovirus, and/or mammalian cell cultures, generally known in the field. Although the polypeptides have been obtained by other means, embodiments of the instant invention provide one or more recombinant proteins mostly in (or close to) their native forms with a desirable conformation for binding with antibodies from tissues of human subjects with HPV infection in an immunological assay.

For example, GST, MBP, or His tagged-HPV16-E6, HPV18 E6, HPV16 E7, HPV18 E7, HPV16 L1, and HPV18 L1 recombinant proteins were expressed in E. coli BL21 (DE3) using IPTG driven induction. After induction of protein expression, tagged-HPV recombinant proteins were obtained from soluble fraction after lysis of the cultured cells and purified to a final concentration of about 0.1 to 1 mg/ml or higher. The purity of the recombinant HPV proteins was estimated to be>90% based on PAGE analysis. Recombinant HPV proteins were used to detect the presence of HPV antibody on clinical samples and were also used as immunogens for production of polyclonal antiserum and monoclonal antibodies.

The cell culture containing various recombinant papillomavirus proteins in various expression vectors as described herein were then scaled up to 1 liter or 10 liter, or 100 liters or higher to obtain high quantity of soluable recombinant protein for purification. The soluble fraction was passed through various chromatography columns with appropriate system to bind to the tag expressed along with the HPV recombinant proteins. The tag-HPV recombinant proteins were then eluted from the column and concentrated down to 100 ml or 10 ml to 1 ml. The purified soluble recombinant HPV proteins were further concentrated and dialyzed with buffers at neutral pH or PBS buffers to be used as immunogen to generate antiserum against the HPV proteins. The soluble recombinant HPV proteins were thus purified from soluble fractions and folded close to their native folding states as in vivo natural conditions.

Obtaining high quality purified recombinant HPV proteins is critical in generating various types of monoclonal antibodies that recognizing common epitopes or specific epitopes for detecting HPV infection. The purified recombinant HPV proteins were tested to confirm its binding to the HPV antibody from the HPV infected clinical samples. Thus, such purified recombinant HPV proteins are suitable for use as immunogen to raise antiserum producing antibody recognizing the natural HPV proteins in vivo.

2. HPV Polyclonal Antibody Production

Recombinant HPV E6, E7 or L1 proteins expressed in E. coli were purified, concentrated, and dialyzed with PBS to be used as immunogen. Immunization was performed by following the standard protocol. Titer of serum was tested by ELISA followed by periodical boosting and bleeding. Production bleed from optimal titer was collected and processed serum was used to do immunoglobulin (Ig) purification by protein A, protein G, or affinity column. Purified IgG was used for HPV immunoassays.

Monoclonal antibodies, polyclonal antibodies, and antiserum were obtained, purified, and tested herein to be able to detect HPV infection regardless of the pathogenesis of HPV infection, cell lesions, inflammatory, or cancer disease development. Other researchers have tried to develop anti-HPV monoclonal antibodies but have failed because they failed to generate sufficient HPV proteins for monoclonal antibodies production; they failed to generate high specificity monoclonal antibodies because the immunogens were not immunogenic; or the generated antibodies were not able to recognize native forms of HPV proteins present in clinical samples for early stage infection. Some antibodies raised against mutant peptides were only able to recognize late stage cervical cancer, but are not sure whether their antibodies would recognize wild type HPV native proteins or any early stage HPV infection. In addition, late stage HPV detection is too late for disease intervention and treatment.

The clinical utility of the antibodies described herein was validated by Immunoassays like ELISA, Immunohistochemistry, or Immunocytochemistry assay using appropriate clinical samples. The novel monoclonal antibodies and antiserum, obtained from methods of this invention are able to interact and bind HPV viral proteins present in clinical samples, which have been confirmed to contain early stage cell lesions such as cervical intraepithelial neoplasia (CIN) as well as late satge HPV associated cervical cancer. The monoclonal antibodies and antiserum as described herein provide powerful tools to detect and screen HPV related pathogenesis and cervical cancer development in both early stages and late stages; thus provide an avenue to intervene disease progression and a chance to provide early treatment.

3. HPV Monoclonal Antibody Development

Recombinant HPV E6, E7 or L1 proteins expressed in *E. coli* was purified, concentrated, and dialyzed with PBS to be used as immunogen. Immunization of mice was performed by following the standard procedure. Titer of serum was tested by ELISA followed by periodical boosting and bleeding. When the titer reaches optimal, fusion was done using standard procedure.

1). Hybridoma screening: To obtain hybridoma cell line producing HPV monoclonal antibody with specificity described in this invention, fusion clones were screened against not only the immunogen but also related or unrelated proteins as well. Two or more purified HPV recombinant proteins were used to screen against each hybridoma clones to obtain the specificity of each monoclonal antibody described herein.

As an example of hybridoma screening, a monoclonal antibody was obtained by screening antibody-producing hybridoma cells with two or more purified recombinant human papillomavirus proteins such that the monoclonal antibody is capable of reacting with the two or more purified recombinant human papillomavirus proteins. The two or more purified recombinant human papillomavirus proteins described herein consists of HPV 16 E6 protein, HPV 16 E7 protein, HPV 16 L1 protein, HPV 18 E6 protein, HPV18 E7 protein, HPV 18 L1 protein, and combinations thereof.

The two or more purified recombinant human papillomavirus viral proteins are HPV early proteins such that the monoclonal antibody is capable of reacting with the two or more human papillomavirus early proteins. For example, the selected hybridoma cell line produced a monoclonal antibody recognizing a common epitope on both HPV16 E6 and HPV16 E7 proteins. As another example, the selected hybridoma cell line produced a monoclonal antibody recognizing a common epitope on both HPV18 E6 and HPV18 E7 proteins.

As another example, the two or more purified recombinant human papillomavirus proteins comprise a purified recombinant human papillomavirus early protein and a purified recombinant human papillomavirus late protein such that the monoclonal antibody is capable of reacting with a common epitope on the purified recombinant human papillomavirus early protein and the purified recombinant human papillomavirus late protein. The purified recombinant human papillomavirus early protein consists of HPV 16 E6 protein, HPV 16 E7 protein, HPV 18 E6 protein, HPV18 E7 protein, and combinations thereof, and the purified recombinant human papillomavirus late protein consists of HPV 16 L1 protein, HPV 18 L1 protein, and combinations thereof.

For example, the selected hybridoma cell lines produced a monoclonal antibody recognizing a common epitope on HPV16 E6, HPV16 E7, and HPV16 L1 proteins or a common epitope on HPV16 E6 and HPV18 E6 proteins or a common epitope on HPV16 E7 and HPV18 E7 proteins or a common epitope on HPV16 E6, HPV16 E7, HPV16 L1, HPV18 E6, and HPV18 E7 proteins as described in the drawings of this invention.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types are selected from the group consisting of HPV 16, and HPV 18. The two or more different HPV types can also be selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof. As an example, the first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a specific epitope on only one of the first and the second purified recombinant human papillomavirus proteins and not the other purified recombinant human papillomavirus protein. The first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

2). Hybridoma cell line stocks: positive clones with desired reactivity on ELISA were selected and cloned down to single cell. Each single clone was then grown up by tissue culture. When the cell numbers reach millions of cell per ml, the cells were frozen down and kept at −80 C or in liquid nitrogen as stock for each cell line.

3). Ascites production: each cell line was grown in tissue culture and injected to mice for ascites production. Ascites were collected and processed for Ig purification by protein G column. Purified Ig from each cell line was isotyped and used for HPV immunoassays.

4. The Specificity of Anti-HPV Antibodies

One or more immunological assays can be used to test the specificity of the monoclonal antibodies generated by screening the hybridoma cell lines with two or more HPV recombinant proteins. EIA (Enzyme Immuno Assay) and/or Western blots were used as the assay format to test the specificity of the HPV antibodies described herein. Various purified recombinant HPV proteins, including the original screening proteins used for obtaining the anti-HPV antibodies and other proteins not used for screening, were used to coat on the microtiter plate to test the specificity of the obtained anti-HPV antibodies on EIA. Proteins in cell lysate from cervical cancer cell lines (with or without HPV infection) were also used to test the specificity of the anti-HPV antibodies by western blot. To confirm the binding and reactivity of the HPV antibodies with proteins from HPV infected cell lines, western blot is very useful to demonstrate specific protein bands corresponding to the proteins present in the HPV-infected cell lines. The protein bands from Western blots were compared to recombinant HPV proteins at their expected molecular weight positions on SDS-PAGE gels. Cell lysate from cervical cancer cell lines, including Hela cell line (HPV18 positive), SiHa cell line (HPV16 positive) and C33A cell line (non-HPV infected) were used to demonstrate detection of HPV E6, E7, or L1 by the HPV monoclonal antibody on western blot.

Figure 1B:
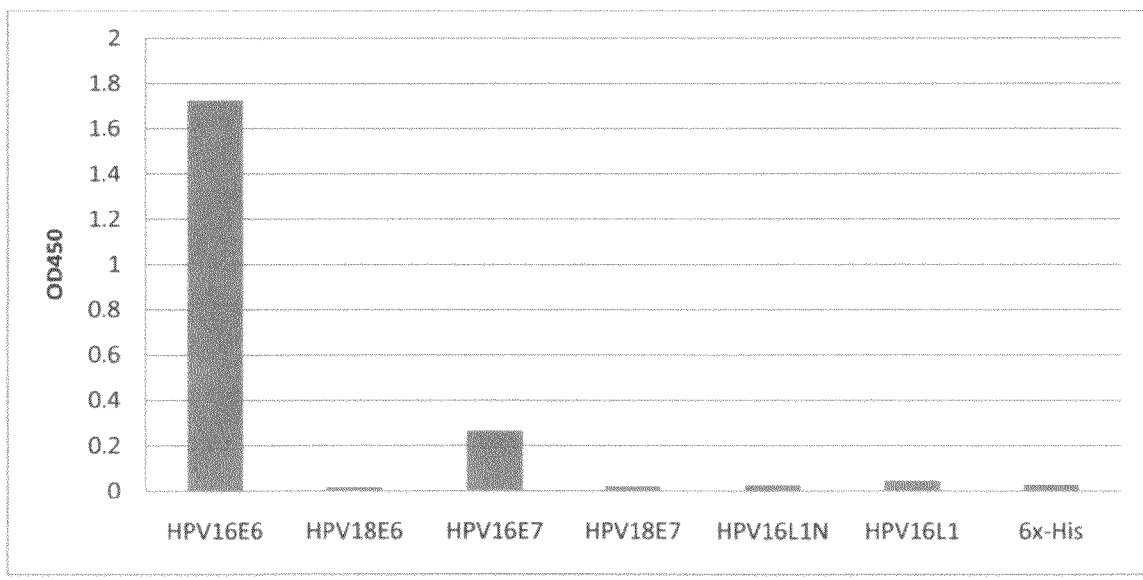
FIG. 1B shows the specificity of another monoclonal antibody capable of reacting with both HPV16 E6 and HPV16 E7 recombinant proteins and recognizing a common epitope on the HPV 16 E6 and HPV16 E7 proteins as assayed on EIA according to one embodiment of the invention.

To demonstrate a monoclonal antibody capable of binding to two or more HPV viral proteins from the same HPV type as described in this invention, FIG. 1A and FIG. 1B show the specificity of a monoclonal antibody, capable of reacting with both recombinant HPV16 E6 and HPV16 E7 proteins on EIA. These data demonstrate the monoclonal antibody described herein reacts specifically to HPV16 E6 and HPV16 E7, but not reactive to HPV16L1, HPV18 E6 or HPV18E7. FIG. 1A and FIG. 1B represent two different clones of hybridoma cells, with each clone being capable of producing a monoclonal antibody recognizing a common epitope on both HPV16 E6 and HPV16 E7 proteins.

Figure 2A:
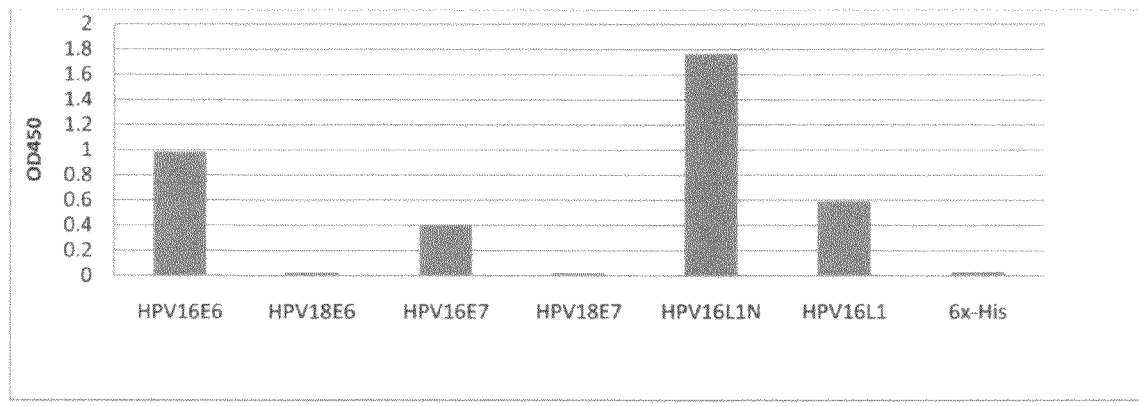
FIG. 2A shows the specificity of a monoclonal antibody capable of reacting with HPV16 E6, E7, L1 & L1 N-terminal recombinant proteins (different HPV proteins from the same HPV type) and recognizing a common epitope on the different E6, E7, L1, and L1 N-terminal proteins from the same HPV 16 type as assayed on EIA according to another embodiment of the invention.

To demonstrate a monoclonal antibody capable of binding to an early HPV viral protein and a late HPV viral proteins from the same HPV type as described in this invention, FIG. 2A shows the specificity of a monoclonal antibody capable of reacting with recombinant HPV E6, HPV E7 and HPV L1 proteins on EIA. The recombinant protein coated on microtiter plate to be detected by the antibody described herein is in native form. These data demonstrate the monoclonal antibody described herein reacts strongly to the native forms of recombinant HPV16 E6 and L1 proteins and weakly to the native form of recombinant HPV16 E7 protein, but is non-reactive to native form of recombinant HPV18 E6 or HPV18 E7. These data indicate that this antibody recognizes an HPV 16 common epitope on the native form of HPV16E6, HPV16E7 and HPV16L1 protein.

Figure 2B:
FIG. 2B shows a western blot of the monoclonal antibody as shown in FIG. 2A, confirming its binding to all of the HPV16 E6, E7 and L1 recombinant proteins.

FIG. 2B shows the results of a Western blot analysis of a monoclonal antibody capable of reacting with recombinant HPV E6, HPV E7 and HPV L1 proteins. The recombinant protein detected by Western blot using the antibody described herein demonstrates the detection of HPV E6 (about 18-20 kDa) and HPV L1 (about 55 kDa) proteins. The bands from each recombinant protein shown with expected molecular weight indicate the monoclonal antibody described herein reacts strongly to denatured HPV16 E6 and HPV18E6 and weakly to denatured HPV L1 proteins on Western blot, and there is no detectable reactivity to HPV16 E7 nor HPV18 E7. Comparing the results as shown in FIG. 2A and FIG. 2B, these data indicate that this anti-HPV monoclonal antibody recognizes an HPV common epitope on the native forms of HPV16 E6, HPV16 E7 and HPV16 L1 protein as well as denatured forms of HPV18 E6 recombinant protein.

Figure 2C:
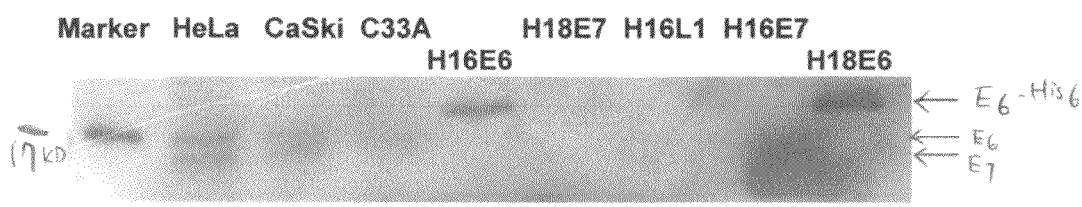
FIG. 2C shows the results of a western blot of cell lysate from cervical cancer cell lines using the monoclonal antibody as shown in FIG. 2A, confirming its binding to all of the HPV16 E6, E7 and L1 viral proteins present in these cervical cancer cell lines.

FIG. 2C shows the results of a Western blot using cell lysate from various cervical cancer cell lines to react with the same monoclonal antibody tested in FIG. 2B binding with recombinant HPV E6, HPV E7 and HPV L1 proteins. Both the cell lysate and recombinant proteins in their denatured forms are tested and shown here (the same monoclonal antibodies as shown in FIG. 2B). The double bands as detected by the monoclonal antibody around the standard molecular weight marker of 17 kDa demonstrate the detection of HPV E6 protein (about 18 kDa) and HPV E7 (about 15 kDa) protein from cervical cancer cell line in HeLa (HPV18) and SiHa (HPV16) cell lines, but not C33A (non-HPV infection) cell line. The bands on the recombinant protein lanes shown with expected molecular weight indicate that the monoclonal antibody reacts strongly to denatured HPV16 E6 and HPV18E6 recombinant proteins, but weakly to denatured HPV L1 recombinant proteins on western blot, and there is no detectable binding to HPV16E7 nor HPV18E7 recombinant proteins.

Figure 3A:
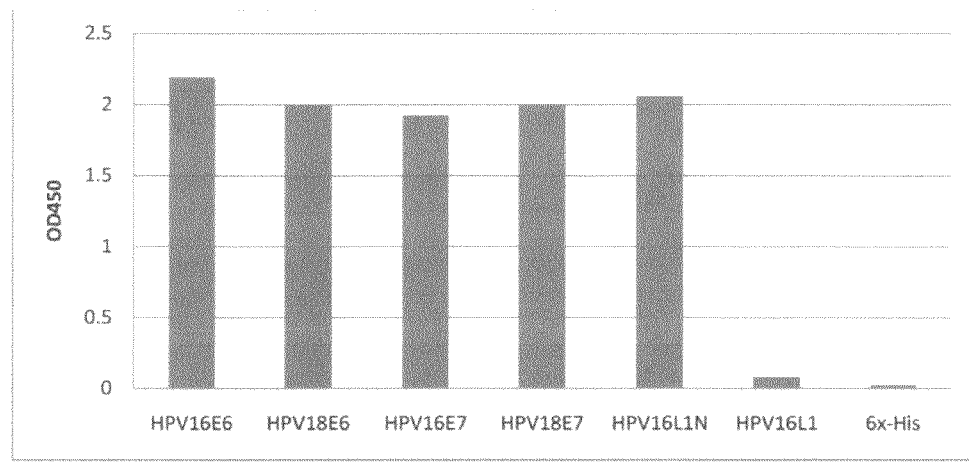
FIG. 3A shows the specificity of a monoclonal antibody capable of binding to all of the recombinant HPV16 E6, E7, and L1 N-terminal proteins as well as HPV18 E6 and E7 proteins (HPV proteins from different HPV types) and recognizing a common epitope on the E6, E7, L1 N-terminal proteins from HPV16 and HPV18 as assayed on EIA according to another embodiment of the invention.

To demonstrate a monoclonal antibody capable of binding to an early HPV viral protein and a late HPV viral protein from different HPV types as described in this invention, FIG. 3A shows the specificity of a monoclonal antibody capable of reacting with recombinant E6, E7 and L1 proteins from both HPV16 and HPV 18 on EIA. These data demonstrate this monoclonal antibody reacts specifically to all of the recombinant E6, E7 and L1 proteins of HPV16, and the recombinant E6 and E7 proteins of HPV18, but not to its common his-tag peptide. These data indicate that this antibody recognizes a common epitope shared by HPV16 and HPV18, as evidenced by its ability to bind to all of the recombinant HPV16 E6, HPV16 E7, HPV16 L1, HPV18 E6, and HPV18 E7 proteins.

Figure 3B:
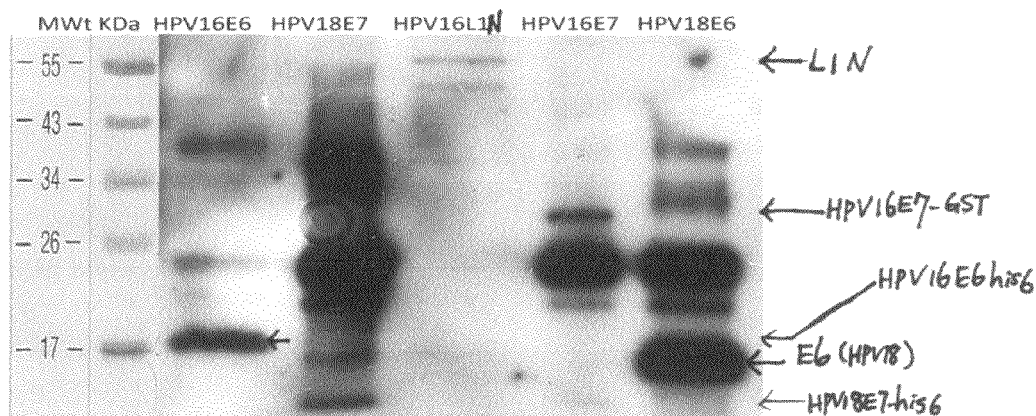
FIG. 3B shows the results of a western blot using the monoclonal antibody as shown in FIG. 3A, confirming its binding to the different recombinant proteins and recognizing a common epitope on the different E6, E7 and L1 proteins from the two different HPV types HPV16 and HPV18.

FIG. 3B shows the results of a Western blot using a monoclonal antibody that recognized a common epitope and is capable of binding to the recombinant E6, E7 and L1 proteins of HPV16 and HPV18. The reactivity of this monoclonal antibody to these recombinant proteins demonstrate that the monoclonal antibody is capable of recognizing E6 (about 18 kDa), E7 (About 15 kDa) and L1 (about 55 kDa) proteins. The resulting bands from each recombinant protein lane of the Western blot analysis showed up at the expected molecular weight position and indicated that this monoclonal antibody reacts strongly to denatured E6 and E7 proteins from both HPV 16 and HPV18, and weakly to denatured L1 proteins on Western blot. The results of FIG. 3A and FIG. 3B indicate that this monoclonal antibody recognizes an HPV common epitope and is capable of binding to the native and denatured form of HPV16 E6, HPV16 E7, HPV16 L1, HPV18 E7 and HPV18 E6 proteins.

Figure 3C:
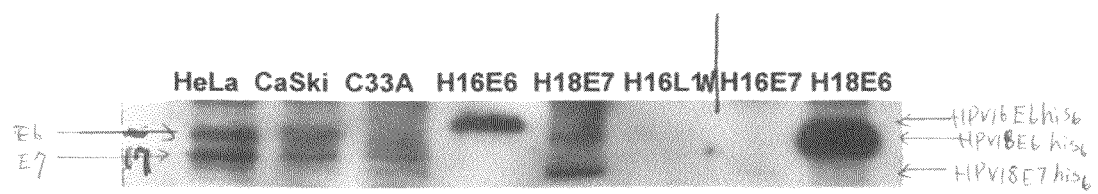
FIG. 3C shows a western blot cell lysate from cervical cancer cell lines using the monoclonal antibody as shown in FIG. 3A, confirming its binding to the HPV16 E6, E7 and L1 proteins as well as HPV18 E6, E7 and L1 viral proteins present in these cervical cancer cell lines.

FIG. 3C shows the results of a Western blot using cell lysate from various cervical cancer cell lines to react with the same monoclonal antibody tested in FIG. 3B binding with recombinant HPV E6, HPV E7 and HPV L1 proteins. Both the cell lyate and the recombinant proteins in their dentured forms were tested and shown here (the same monoclonal antibodies as shown in FIG. 3B). The double bands as detected by the monoclonal antibody around the standard molecular weight marker of 17 kDa demonstrate the detection of HPV E6 protein (about 18 kDa) and HPV E7 (about 15 kDa) protein from cervical cancer cell line in HeLa (HPV18) and SiHa (HPV16) cell lines, but not C33A (non-HPV infection) cell line. The bands on the recombinant protein lanes shown with expected molecular weight indicate that the monoclonal antibody reacts strongly to denatured HPV16 E6, HPV18 E6, HPV18 E7 recombinant proteins but weakly to denatured HPV L1 recombinant proteins, and there is no detectable binding to HPV16E7 recombinant proteins on the Western blot.

Figure 4A:
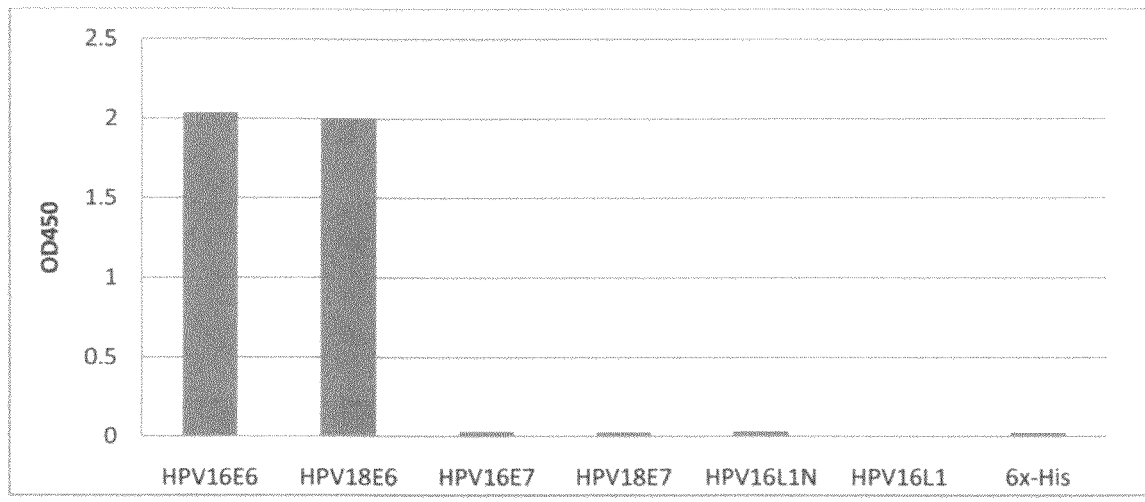
FIG. 4A shows the specificity of a monoclonal antibody capable of binding to two E6 recombinant proteins (HPV16 E6 and HPV18 E6, E6 proteins from different HPV types) and recognizing a common epitope on the two E6 proteins from different HPV types as assayed on EIA according to another embodiment of the invention.

To demonstrate a monoclonal antibody capable of binding to two or more HPV viral proteins from different HPV types as described in this invention, a monoclonal antibody capable of reacting with recombinant E6 proteins of HPV 16 and HPV18 was also the obtained. FIG. 4A shows the specificity of a monoclonal antibody that recognizes the common epitope and is capable of binding to recombinant HPV16 E6 and HPV18E6 proteins on EIA. The recombinant protein coated on microtiter plate to be detected by the antibody described herein is in its native form. These data demonstrate that the monoclonal antibody reacts strongly to the native form of recombinant HPV16 E6 and HPV18E6 proteins, but does not react with the native form of either recombinant HPV E7 or recombinant HPV L1 proteins. These data indicate that this antibody recognizes an HPV E6 common epitope and is capable of binding to the native form of recombinant HPV16 E6, and HPV18 E6 proteins.

Figure 4B:
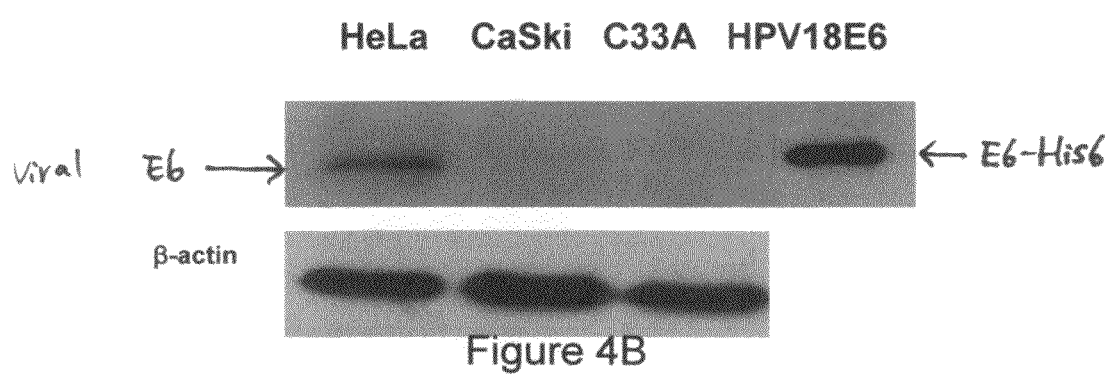
FIG. 4B shows the results of a western blot analyzing the cell lysate from cervical cancer cell lines us ing the monoclonal antibody as shown in FIG. 4A, confirming its binding to HPV16 E6 as well as HPV18 E6 viral proteins present in these cervical cancer cell lines.

FIG. 4B shows the results of a Western blot using cell lysate from various cervical cancer cell lines to react with the same monoclonal antibody tested in FIG. 4A binding with recombinant E6 proteins of HPV 16 and HPV18. Both the cell lyate and the recombinant proteins in their dentured forms were tested and shown here (the same monoclonal antibodies as shown in FIG. 4A). The single band as detected by the monoclonal antibody around the standard molecular weight marker of 17 kDa demonstrate the detection of HPV E6 protein (about 18 kDa) from cervical cancer cell line in HeLa (HPV18), but not C33A (non-HPV infection) cell line. The bands on the recombinant protein lanes shown with expected molecular weight indicate that the monoclonal antibody reacts strongly to denatured HPV18E6 recombinant proteins.

Figure 5:
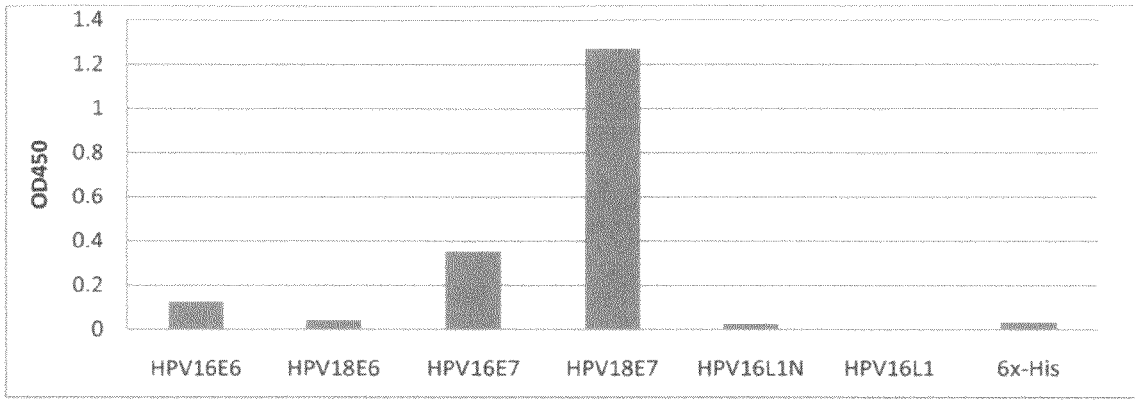
FIG. 5 shows the specificity of a monoclonal antibody capable of reacting with two recombinant HPV16 E7 and HPV18 E7 proteins (E7 proteins from different HPV types) and recognizing a common epitope on the two E7 proteins from different HPV types as assayed on EIA.

As another example to demonstrate a monoclonal antibody capable of binding to two or more HPV viral proteins from different HPV types as described in this invention, FIG. 5 shows the specificity of a monoclonal antibody capable of reacting with both recombinant HPV16 E7 and HPV18E7 protein on EIA. The recombinant protein coated on microtiter plate detected by the antibody described herein is in its native form. These data demonstrate the monoclonal antibody described herein reacts strongly to native form of recombinant HPV16 E7 and HPV18 E7 proteins, but non-reactive to native form of recombinant HPV E6 nor HPV L1 proteins. These data indicate that this antibody recognizes an HPV E7 common epitope and is capable of binding to the native form of HPV16 E7 and HPV18 E7 proteins.

Figure 6:
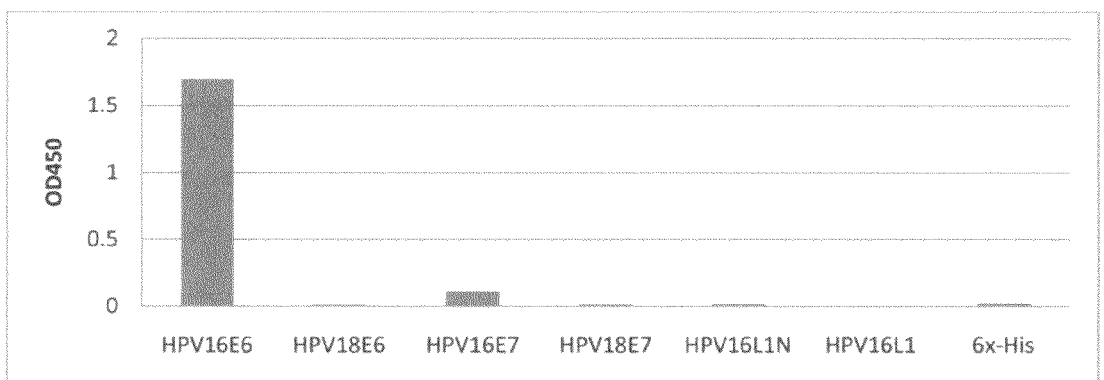
FIG. 6 shows the specificity of a monoclonal antibody capable of reacting with only HPV16 E6 recombinant protein but not with any other HPV recombinant proteins on EIA according to one embodiment of the invention.

To demonstrate a monoclonal antibody capable of binding to only a first HPV viral protein, but not a second HPV viral protein different from the first HPV viral protein, FIG. 6 shows the specificity of a monoclonal antibody capable of reacting with recombinant HPV16 E6 but not with other recombinant HPV proteins on EIA. Data indicate the specificity of this monoclonal antibody that recognizes a specific epitope and is capable of binding to HPV16 E6 only, and not to HPV18 E6 or other recombinant HPV proteins on EIA. The recombinant protein coated on microtiter plate detected by the antibody described herein is in native form. These data demonstrate the monoclonal antibody described herein reacts strongly to the native form of recombinant HPV16 E6 proteins but is non-reactive to the native form of recombinant HPV E7 or L1 proteins. These data also indicate that this antibody recognizes an HPV16 E6-specific epitope and is capable of binding to HPV16 E6 protein only.

As an another example, FIG. 7 shows the specificity of a monoclonal antibody capable of reacting with recombinant HPV18 E6 protein but not with other recombinant HPV proteins on EIA. Data indicate the specificity of this monoclonal antibody that recognizes a specific epitope and is capable of binding to HPV18 E6 only, but not to HPV16 E6 or other recombinant HPV proteins. The recombinant protein coated on microtiter plate detected by the antibody described herein is in native form. These data demonstrate the monoclonal antibody described herein reacts strongly to the native form of recombinant HPV18 E6 proteins but is non-reactive to the native form of recombinant HPV E7 or HPV L1 proteins. These data indicate that this antibody recognizes an HPV18 E6-specific epitope and is capable of binding to HPV18 E6 protein only.

Figure 7A:
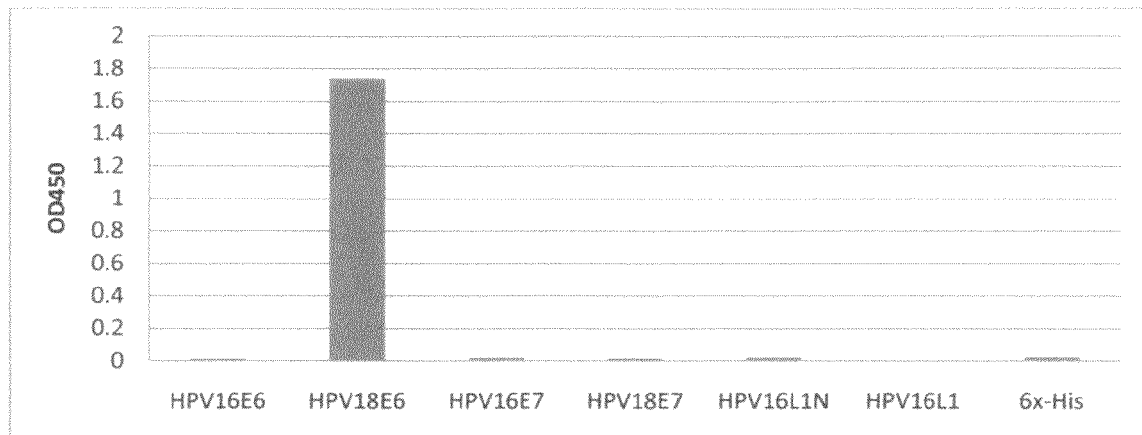
FIG. 7A shows the specificity of a monoclonal antibody capable of reacting specifically with only HPV18 E6 recombinant protein, but not with any other HPV16 or HPV18 recombinant proteins as assayed on EIA according to another embodiment of the invention.
Figure 7B:
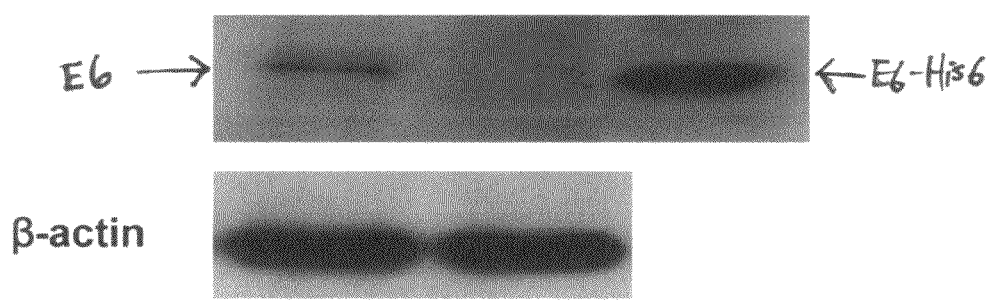
FIG. 7B shows the results of a western blot analyzing the cell lysate from different cervical cancer cell lines using the monoclonal antibody as shown in FIG. 7A, confirming its binding to the-HPV18 E6 viral protein but not HPV E7 viral protein that are present in Hela cell line.

FIG. 7B shows the results of a Western blot using cell lysate from various cervical cancer cell lines to react with the same monoclonal antibody tested in FIG. 7A binding with recombinant HPV 18 E6 proteins. Both the cell lyate and the recombinant proteins in their dentured forms were tested and shown here (the same monoclonal antibodies as shown in FIG. 7A). The single band as detected by the monoclonal antibody around the standard molecular weight marker of 17 kDa demonstrate the detection of HPV E6 protein (about 18 kDa) from cervical cancer cell line in HeLa (HPV18), but not C33A (non-HPV infection) cell line. The bands on the recombinant protein lanes shown with expected molecular weight indicate that this monoclonal antibody reacts strongly to denatured HPV18E6 recombinant proteins only.

Figure 8:
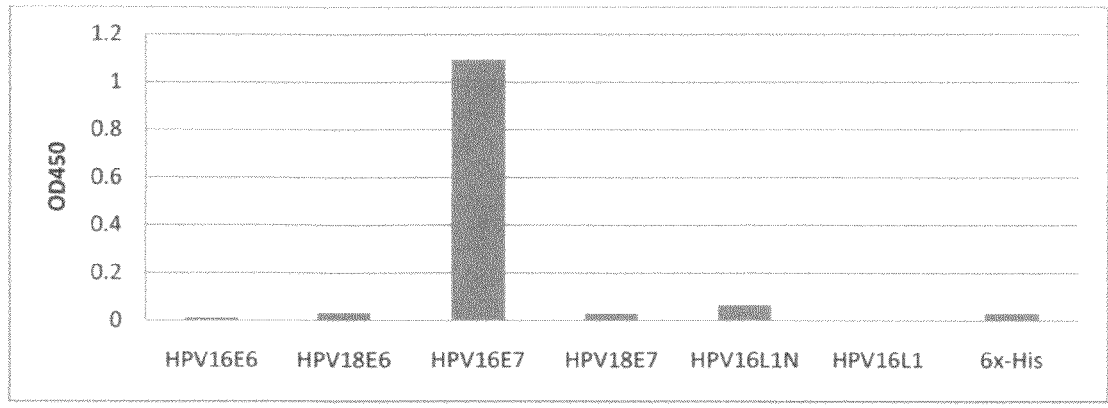
FIG. 8 shows the specificity of a monoclonal antibody capable of reacting specifically with an HPV16 E7 recombinant protein, but not with any other HPV recombinant proteins as assayed on EIA according to another embodiment of the invention.

As another example, FIG. 8 shows the specificity of a monoclonal antibody capable of reacting with recombinant HPV16 E7 but not with other recombinant HPV proteins on EIA. Data indicate the specificity of the monoclonal antibody that recognizes specific epitope and is capable of binding to HPV16 E7 only, but not to HPV18 E7 or other recombinant HPV proteins on EIA. The recombinant protein coated on microtiter plate detected by the antibody described herein is in its native form. These data demonstrate the monoclonal antibody described herein reacts strongly to the native form of recombinant HPV16 E7 proteins, but no detectable binding to the native form of recombinant HPV E6 or L1 proteins. These data indicate that this antibody recognizes an HPV16 E7-specific epitope and is capable of binding to HPV16 E7 protein only.

Figure 9:
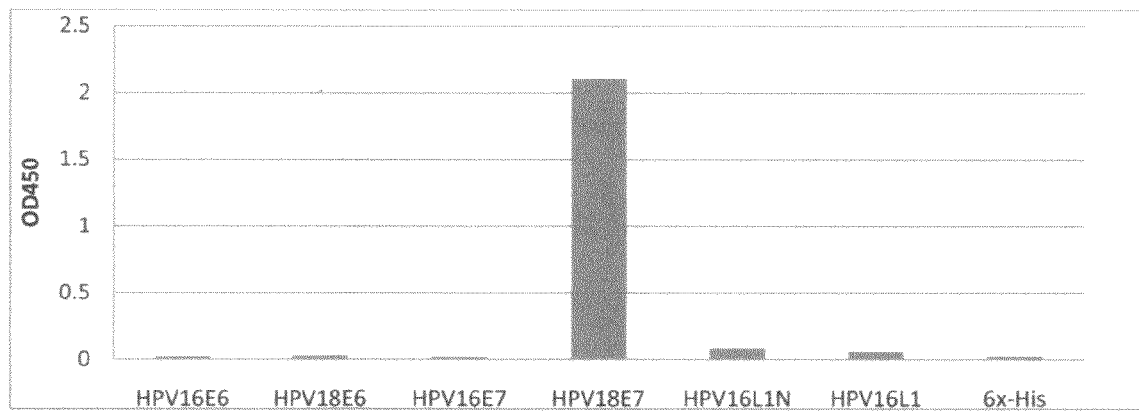
FIG. 9 shows the specificity of a monoclonal antibody capable of reacting specifically with a recombinant HPV18 E7 recombinant protein, but not with any other HPV recombinant proteins as assayed on EIA according to another embodiment of the invention.

As an another example to demonstrate a monoclonal antibody capable of binding to only a first HPV viral protein, but not a second HPV viral protein different from the first HPV viral protein, FIG. 9 shows the specificity of a monoclonal antibody capable of reacting with recombinant HPV18 E7 but not with other recombinant HPV proteins on EIA. Data indicate the specificity of the monoclonal antibody that recognizes a specific epitope and is capable of binding to HPV18 E7 only, and not to HPV16 E7 or other recombinant HPV proteins. The recombinant protein coated on microtiter plate detected by the antibody described herein is in native form. These data demonstrate the monoclonal antibody described herein reacts strongly to the native form of recombinant HPV18 E7 proteins but is non-reactive to native form of recombinant HPV E6 or HPV L1 proteins. These data indicate that this antibody recognizes an HPV18 E7-specific epitope and is capable of binding to HPV18 E7 protein only.

Figure 10A:
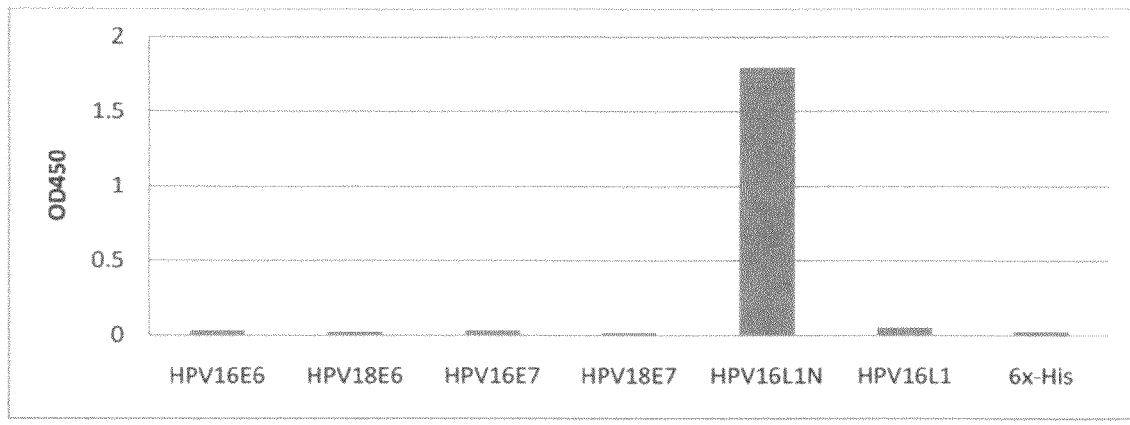
FIG. 10A shows the specificity of a monoclonal antibody capable of reacting specifically with an HPV16 L1 N-terminal recombinant protein, but not with any other HPV recombinant proteins as assayed on EIA according to another embodiment of the invention.
Figure 10B:
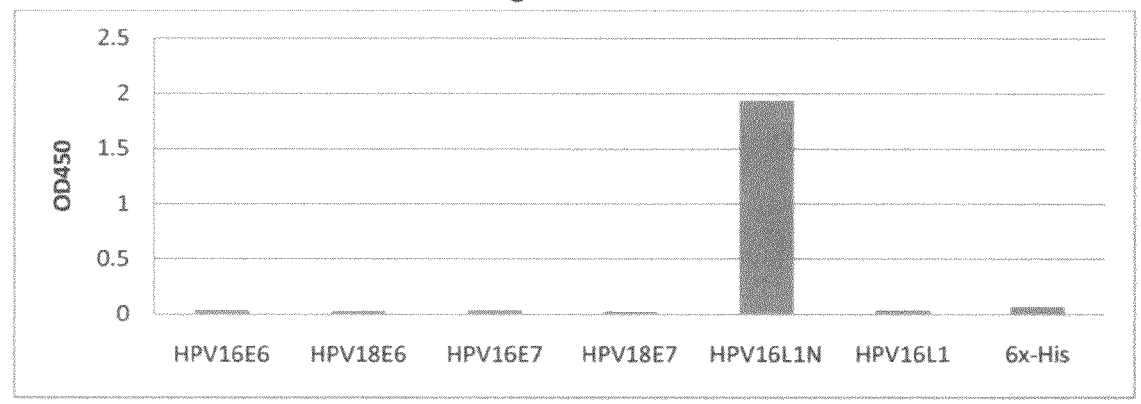
FIG. 10B shows the specificity of another monoclonal antibody capable of reacting specifically with an HPV16 L1 N-terminal recombinant protein, but not with any other HPV recombinant proteins as assayed on EIA.

As an another example to demonstrate a monoclonal antibody capable of binding to only a first HPV viral protein, but not a second HPV viral protein different from the first HPV viral protein, FIG. 10 shows the specificity of a monoclonal antibody capable of reacting with recombinant HPV16 L1-N terminal but not with other recombinant HPV proteins on EIA. Data indicate the specificity of the monoclonal antibody that recognizes a specific epitope and is capable of binding to HPV16 L1 N-terminal only, but does not crossed react with HPV16 L1 or other recombinant HPV proteins on EIA. The recombinant protein coated on microtiter plate detected by the antibody described herein is in its native form. These data demonstrate the monoclonal antibody described herein reacts strongly to the native form of recombinant HPV16 L1-N terminal proteins but is non-reactive to the native form of recombinant HPV E6 or HPV E7 proteins. These data indicate that this antibody recognizes an HPV16 L1 N-terminal specific epitope and is capable of binding to HPV16 L1 N-terminal protein only. FIG. 10A and FIG. 10B represent two different hybridoma clones of cell line producing antibody specific to HPV L1 proteins.

Figure 11:
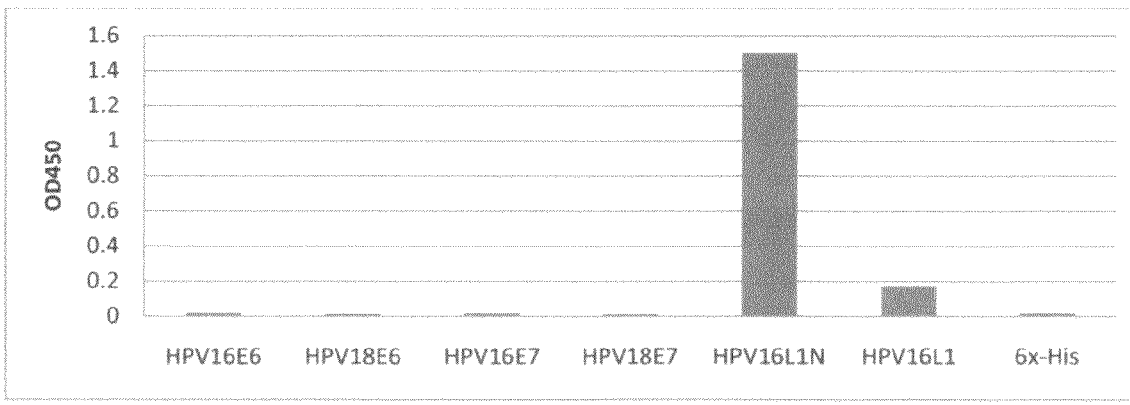
FIG. 11 shows the specificity of a monoclonal antibody capable of reacting specifically with only the HPV16 L1 & L1 N-terminal recombinant proteins, but not with any other HPV recombinant proteins as assayed on EIA according to another embodiment of the invention.

As an another example, FIG. 11 shows the specificity of a monoclonal antibody capable of reacting with recombinant HPV16L1 and HPV16 L1-N terminal but not with other recombinant HPV proteins on EIA. Data indicate the specificity of the monoclonal antibody that recognizes a specific epitope and is capable of binding to HPV16 L1 and HPV16 L1 N-terminal only, and not to other recombinant HPV proteins on EIA. The recombinant protein coated on microtiter plate detected by the antibody described herein is in native form. These data demonstrate the monoclonal antibody described herein reacts strongly to the native form of recombinant HPV 16 L1 and HPV16 L1-N terminal proteins, but is non-reactive to the native form of recombinant HPV E6 or HPV E7 proteins. These data indicate that this antibody recognizes an HPV16 L1 N-terminal-specific epitope and is capable of binding to HPV16 L1 and HPV16 L1 N-terminal protein.

To demonstrate the antibodies described in this invention can be used in various immunoassay, a sandwich ELISA was performed. The assay includes 1). Coating first anti-HPV antibody on the microtiter plate, 2). Adding HPV protein to react with the first antibody, thus to be captured on the surface of microtiter plate, 3). Adding a second anti-HPV antibody which is conjugated with HRP, followed by TMB substrate to report the binding activity by ELISA reader. The sandwich assay provides specific binding of the protein with the first and the second antibody and thus differentiates the antibody specificity for the proteins on the surface to be detected by the ELISA reader. Various antibodies described in this invention were applied in the coating and detection to demonstrate the antibody specificity. As an example, Table 1 shows the experiment design and result of an ELISA (Enzyme linked Immuno Sandwich Assay) to detect the presence of HPV18 E6 recombinant protein. The results show HPV18E6 recombinant protein can be detected in the assay when the coating and detecting antibody are capable of reacting with HPV18E6, while HPV16E6 recombinant protein can't be detected if the coating antibody is capable of binding to HPV16E6 but the detecting antibody reacts with HPV18E6 only. Similar results were obtained when using an HPV18 E6-specific antibody as a coating followed by a detecting antibody capable of binding to both HPV16E6 and HPV18E6. Data demonstrate the specificity of the antibody recognizes HPV18 E6 when HPV18 E6 recombinant protein is used as the testing protein in the sandwich assay but is non-reactive to recombinant HPV16 E6 protein as the antigen of the sandwich assay. The assay format described herein can be used to detect HPV18 E6 proteins present in biological samples, including but not limited to cell lysate from cervical cancer cell lines, cervical scrape samples, tissue, body fluid, serum, etc. This specific sandwich assay provides type specific assay for HPV 18, and thus excludes the binding of HPV16 E6.

TABLE 1

Sandwich ELISA for detecting of HPV E6 protein

| coating antibody | anti-HPV16 &18E6 | anti-HPV16 &18E6 | anti-HPV18E6 | anti-HPV18E6 |
|---|---|---|---|---|
| testing protein | recombinant HPV18E6 | recombinant HPV168E6 | recombinant HPV18E6 | recombinant HPV16E6 |

TABLE 1-continued

Sandwich ELISA for detecting of HPV E6 protein

| detecting antibody | anti-HPV18E6 | anti-HPV18E6 | anti-HPV16 &18E6 | anti-HPV16 &18E6 |
|---|---|---|---|---|
| ELISA results (OD450) | 1.5 | 0.05 | 1.45 | 0.05 |

As an another example to demonstrate the antibodies described in this invention can be used to detect HPV E7 protein, Table 2 shows the result of ELISA to detect the presence of HPV18 E7 recombinant protein using a monoclonal antibody against HPV 18 E7 (recognizing HPV 18 E7) for both the coating and the detecting antibody. Data demonstrate that the specificity of the antibody recognizes HPV18E7 using HPV18E7 recombinant protein as the antigen of the sandwich assay but is non-reactive using HPV16E7 as the antigen of the sandwich assay. The assay format described herein can be used to detect HPV E7 proteins present in biological samples, including but not limited to cell lysate from cervical cancer cell lines, cervical scrape samples, tissue, body fluid, serum, etc. This sandwich assay provides an E7-specific assay for HPV 18, and thus is useful for the screening of HPV infection and the detecting of HPV E7 oncogenic proteins.

TABLE 2

Sandwich ELISA for detecting of HPV E7 protein

| coating antibody | anti-HPV18E7 | anti-HPV18E7 |
|---|---|---|
| testing protein | recombinant HPV18E7 | recombinant HPV16E7 |
| detecting antibody | anti-HPV18E7 | anti-HPV18E6 |
| ELISA results (OD450) | 1.25 | 0.04 |

5. Application of the Anti-HPV Antibodies

The HPV antibodies described in this invention can be used in various immunoassays for detecting general HPV infection as well as infection by various specific HPV genotypes, high risk HPVs and low risk HPVs. The samples to be used in detecting the presence of HPV proteins can be obtained from, but are not limited to, cervical tissues, cervical cells, cervical scrapes, serum, and body fluids. The immunoassays useful for screening or diagnosing cervical cancer or HPV infection include IHC assays, ICC assays, flow cytometry assays, assays using antibodies coupled to beads, rapid tests, protein chip assays, immunoassays with dot blots, immunoassays with slots, as well a conventional ELISA assay. As a screening test, the HPV antibodies can be used to detect HPV proteins in situ present in epithelium cells of cervical scrape from general population in cervical cancer screening as evidenced by ICC staining scored by certified cytologists. As a confirming test, the HPV antibodies can also be used to detect HPV proteins in situ present in epithelium tissue as evidenced by IHC staining scored by certified pathologists.

1). The reactivity of the purified anti-HPV Antibodies with HPV Proteins found in Biological Samples. To confirm the binding activity of the HPV antibodies with HPV proteins, purified HPV recombinant proteins and/or HPV containing cell lysate from biological samples can be tested on ELISA or direct EIA. Biological samples include, but are not limited to, cells from cultured cell lines or from clinical samples. As an example, as data shown on Table 3, monoclonal antibodies specific to HPV E6, HPV E7 or HPV L1 proteins were able to react specifically with cell lysate from various cervical cancer cell lines in a direct EIA format while using HEC-1A as negative control. Cell lysate from cervical cancer cell lines, including Caski, Siha, Cxca, Hela, and endometrial cancer cell line like HEC-1A (non-HPV infected) were used to demonstrate detection of HPV E6, E7, or L1 by the HPV monoclonal antibody specific to HPV E6, HPV E7, and HPV L1 respectively as shown in Table 3.

TABLE 3

EIA detection of E6, E7, and L1 proteins in cervical cancer cell lines.

| OD | Anti-HPV16 E6, HPV18 E6 antibody | Anti-HPV18 E6 antibody | Anti-HPV18 E7 antibody | Anti-HPV16 E7 antibody | Anti-HPV16 L1 antibody |
|---|---|---|---|---|---|
| Caski (HPV16+) | 0.392 | 0.48 | 0.442 | 0.464 | 0.355 |
| Si Ha (HPV16+) | 1.165 | 1.314 | 1.162 | 1.202 | 1.115 |
| CxCa (HPV16+) | 1.126 | 1.047 | 0.802 | 0.825 | 0.724 |
| Hela (HPV18+) | 0.779 | 0.762 | 0.734 | 0.654 | 0.652 |
| HEC-1A (no HPV) | 0.173 | 0.206 | 0.219 | 0.186 | 0.173 |

Cultured cell lines tested and described herein, include, but not limited to, cervical cancer cells such as Caski (HPV16 positive), Siha (HPV16 positive), Cxca, Hela (HPV18 positive), and endometrial cancer cell line like HEC-1A (no HPV infection). For direct EIA, cells were collected, centrifuged, washed, and lysed to generate cell lysate as analyte. The protein in the cell lysate was quantitated and coated to microtiter plate using the same amount of protein for coating of each sample in each well. The plate was blocked, and detected by each of the HPV monoclonal antibody as indicated followed by HRP conjugated anti-mouse IgG. TMB substrate was added followed by a standard reaction stopping solution. $OD_{450}$ was taken by an ELISA plate reader.

2). The reactivity of the purified anti-HPV Antibodies with HPV Proteins found in clinical samples. Clinical samples to be tested and described herein include, but not limited to, cells from cervical scrapes, body fluid, or serum samples Clinical specimens from cervical scrapes were also obtained for detection of HPV E6, E7 or L1 proteins on EIA.

Cell lysate from various sample source including cervical scrape cells in liquid based solution, culture medium (used for HPV DNA test sample), or pap smear sample demonstrate detection of HPV E6, E7, or L1 from clinical samples on EIA format using various HPV monoclonal antibody described in this invention. To perform the direct EIA described herein, specimens were processed, centrifuged, washed, and lysed to generate cell late as analyte. The proteins in the cell lysate was quantitated and coated to microtiterplate with the same amount of proteins for coating in each well. The plate was blocked, and detected by each HPV monoclonal antibody followed by HRP conjugated anti-mouse IgG. TMB substrate was added followed by a stopping solution. $OD_{450}$ was taken by an ELISA plate reader.

Results shown in Table 4 indicate that each monoclonal antibody detects HPV E6, E7, or L1 protein respectively from SCC samples using pap smear normal (HPV neg) as neg control of the assay. For samples from high-grade HPV DNA pos, one out of three is positive on the E6, E7, and L1 by EIA. These data indicate that E6, E7, or L1 proteins from SCC lysate can be detected by EIA using the monoclonal antibodies described herein, while high-grade HPV DNA positive samples (CIN1/2) may or may not contain detectable HPV E6, E7, or L1 proteins. The high-grade HPV DNA test used in this study was hc2, the only FDA approved HPV DNA test. For those HPV DNA positive but HPV EIA negative samples, it is possible false positive of the HPV DNA assay, or positive HPV DNA detection with no expression of HPV oncogenic proteins. These data indicate that HPV EIA assay described herein provides additional clinical relevance for screening of cervical cancer.

TABLE 4

EIA detection of E6, E7, and L1 proteins in cervical scrapes samples.

| Samples Dx | Anti-HPV18 E6 antibody | Anti-HPV16 E7 antibody | Anti HPV L1 antibody |
|---|---|---|---|
| Squamous cell carcinoma (SCC) | +++ | +++ | +++ |
| Squamous cell carcinoma (SCC) | +++ | +++ | +++ |
| high grade HPV DNA test positive | − | − | − |
| high grade HPV DNA test positive | + | + | + |
| high grade HPV DNA test positive | − | − | − |
| pap smear normal, PCR negative | − | − | − |
| pap smear normal, PCR negative | − | − | − |
| pap smear normal, PCR negative | − | − | − |

3). The reactivity of the purified anti-HPV Antibodies with HPV Proteins in situ by immunohistochemistry (IHC): Paraffin tissue blocks sectioned into 4 microns were placed on slide and baked at 60° C. for overnight. Deparaffin/hydrate sections were unmasked followed by standard IHC staining procedures. Purified monoclonal antibodies against HPV proteins as described in this invention were diluted to use as the primary antibody. Staining procedure was followed by secondary antibody solution and washing, then followed by appropriate substrate reagent to each section. As soon as the sections developed, slides were immersed in distilled water, sections were counterstained with hematoxylin and dehydrated, and the coverslips were mounted.

As an example, various cervical tissues from various stages of CIN were prepared to perform IHC assay using rabbit polyclonal anti-HPV E7 antibodies described herein. As another examples, a number of cervical biopsy samples were tested in an immunohistochemistry (IHC) assay concurrently as a tissue microarray format using a monoclonal antibody to detect HPV proteins from a variety of HPV types (as confirmed by HPV DNA genotyping). Using a monoclonal antibody against HPV viral proteins and/or oncoproteins, this invention provides antibodies to detect the presence of HPV L1 viral proteins and E6, E7 oncoproteins in clinical samples having either single HPV infection or multiple HPV infections. A single anti-HPV monoclonal antibody as described herein can detect single HPV infection by at least HPV-6, HPV-16, HPV-18, HPV-31, HPV-33, HPV-52, etc, which are cancer-related HPV types (either high risk HPV types or low risk HPV types). A single anti-HPV monoclonal antibody can detect HPV infection by two or more HPV types, such as the combination of HPV-16, HPV-18, HPV-52, HPV-58, HPV-44, HPV-51, HPV-39, HPV-59, etc., which include high risk, low risk, and non-oncogenic α-papillomaviruses.

As an example, the HPV antibodies described in this invention can be applied in clinical utility. The results of the IHC assay demonstrate detection of the HPV E7 protein present in situ from various stages of cervical tissues using a mouse monoclonal anti-HPV E7 antibody. As another example, the antibodies described herein were also used in ICC assay using various cervical tissues from various stages of CIN. As another examples, results of IHC staining using a mouse monoclonal anti-HPV E6 antibody demonstrate detecting the HPV E6 protein present in situ from various stages of CIN tissues. These results indicate that HPV E6 and HPV E7 oncoproteins over-expressed in the dysplasia cells can be specifically detected by the IHC staining using the specific HPV antibodies.

As an example, FIGS. 12A-12D show IHC staining of CIN tissue demonstrated by a mouse monoclonal anti-HPV E6 antibody. Results indicate expression of E6 oncoprotein can be detected early in the precancerous stage of CIN2. Solid Black arrows indicate the specific staining of E6 protein in dysplasia cells, while empty clear arrows indicate the normal cells with no stain. Highly magnified images indicate localization of the E6 proteins expressed early in the nuclear of dysplasia cells.

FIG. 12A shows the representative image of the dysplasia cells of CIN2 tissues stained by immunohistocytostaining (IHC) using an anti-E6 monolonal antibody. FIG. 12B shows the representative image of the adjacent normal epithelium from the dysplasia tissue of the CIN2 sample of FIG. 12A. FIG. 12C-12D shows the representative image of the dysplasia epithelium of two CIN3 samples stained by IHC using the same anti-E6 monolonal antibody. These data suggest the IHC staining by E6 monoclonal antibody is specific in the nuclear and cytoplasm of dysplasia cells.

Figure 13A:
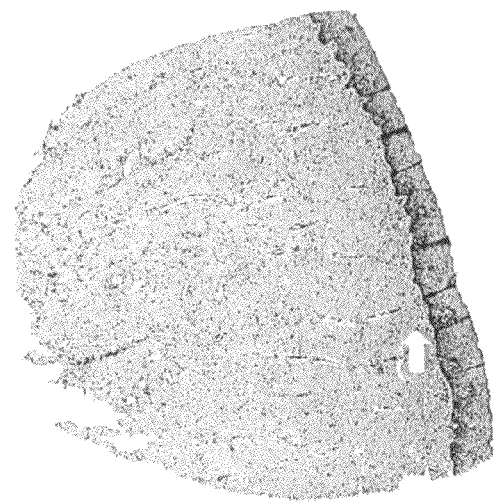
FIG. 13A shows the representative staining image of the squamocarcinoma (SCC) tissue from tissue microarray using an anti-E7 monolonal antibody in an immunohistocytostaining (IHC) assay.
Figure 13B:
FIG. 13B shows the representative staining image of the normal epithelium (about 15 mm away from the tumor tissue) adjacent the SCC tissue of FIG. 13A.
Figure 13C:
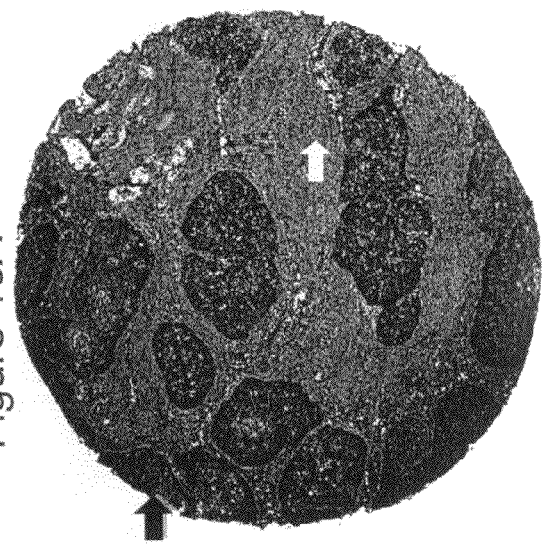
FIG. 13C shows the representative staining image of another SCC sample stained by the same anti-E7 monolonal antibody as used in FIG. 13A in an IHC assay, demonstrating specific IHC staining in the tumor cells by the anti-E7 monoclonal antibody.
Figure 13D:
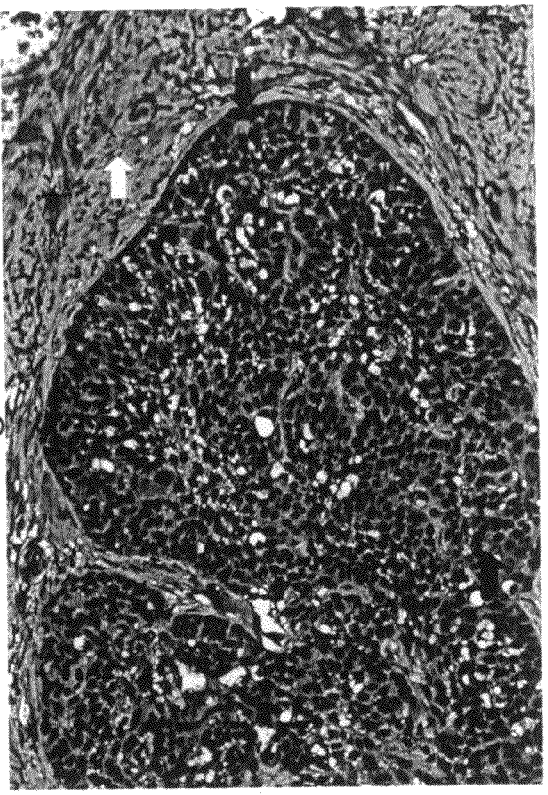
FIG. 13D shows the magnified representative image of the tumor cells from FIG. 13C to view the staining of the cytoplasm of the tumor cells.

As an another example, FIGS. 13A-13D show IHC staining of squamous cell carcinoma demonstrated by mouse monoclonal HPV E7 antibody. Results indicate expression of E7 oncoprotein can be detected in the tumor cells of SCC tissue. Solid Black arrows indicate the specific staining of E7 protein in dysplasia cells, while empty clear arrows indicate the normal cells with no stain. Highly magnified images indicate localization of the E7 proteins expressed in the cytoplasm of tumor cells, but not in the normal epithelium, or stroma cells. These data suggest the IHC staining by E7 monoclonal antibody is specific in the cytoplasm of tumor cells. FIG. 13A shows the representative image of the squamocarcinoma (SCC) tissue from tissue microarray stained by IHC using an anti-E7 monoclonal antibody. FIG. 13B shows the representative image of the normal epithelium (15 mm away from the tumor tissue) of the SCC subject from FIG. 13A. FIG. 13C shows the representative image of another SCC sample from tissue microarray stained by IHC using the same anti-E7 monoclonal antibody. FIG. 13D shows the magnified representative image of the tumor cells stained in cytoplasm from FIG. 13C.

4). The reactivity of the purified anti-HPV Antibodies with HPV Proteins in situ by immunocytochemistry (ICC):

Cervical scrapes collected by Liquid based solution were processed according to the manufacture instruction. The cell preparation was divided into two parts, one for conventional papsmear, the other one for immunostaining. Monolayer of cervical cells on slide was processed by cytospin or thin prep techniques. The cells were then fixed and stained followed by immunostaining protocol. Stained cells are visualized under microscope.

As an example, FIG. 14A-14C demonstrate immunocytochemistry assay using anti-HPV antibody. FIG. 14A shows the representative image of cervical cells from a CIN2 cervical scrape sample prepared by thin prep and stained by ICC using a mouse monoclonal anti-HPV E7 antibody. FIG. 14B shows the representative image of cervical cells from a CIN3 cervical scrape sample prepared by thin prep and stained by ICC using a mouse monoclonal anti-E6 antibody. FIG. 14C shows the representative image of cervical cells from an adenocarcinoma (ADC) cervical scrape sample prepared by thin prep and stained by ICC using the same anti-E6 antibody shown in FIG. 14B.

The one or more immunological assays using antibodies and purified recombinants proteins derived from HPV early and/or late genes as obtained herein serve as reliable indicators whether HPV infection has occurred. In addition, HPV associated malignancy or pre-malignant cell transformation can be assayed. One of the most useful aspects of the invention is in diagnosing cervical carcinoma, both squamous cell carcinoma and adenocarcinoma as well as any epithelial cell abnormality associated with oncogenic HPV infection including koilocytosis; hyperkeratosis; precancerous conditions encompassing intraepithelial neoplasia or intraepithelial lesion; high-grade dysplasias; and invasive or malignant cancers.

In high grade CIN lesions, E6 and E7 are strongly expressed in host basal epithelial cells and interfere substantially with cell cycle control of these replication competent host cells. Expression of HPV oncoproteins interferes with G1-S-Phase regulation in host cells. The HPV E6 and E7 proteins target a plethora of cellular interactions, such as the inactivation of pRB by E7 and the degradation of p53 by E6. High level of HPV E7 proteins inactivates pRB and leads to disruption of E2F-Rb binding. Usually, binding of pRB to E2F blocks E2F driven cell cycle activation. In replicating cells, E2F is regulated by phosphorylation of RB. Rb phosphorylation is normally mediated by cyclin dependent kinases (CDK4, CDK6) that are controlled by several kinase inhibitors (INKs).

As a result of the loss of Rb/E2F repression and the strong activation by free E2F, the expression of a host cell protein, p16INK4a, is strongly overexpressed. In addition, S-phase genes are continuously activated since the p16INK4a mediated repression of Cdk4/6 has no downstream effect on pRb host cell protein. Since E7-dependent E2F release is not mediated by phosphorylation of pRb, the counter-regulatory p16INK4a expression has no effect on the activated cell cycle. Under physiological conditions p16INK4a is expressed when cells undergo a genomic stress situation such as substantial shortening of telomeres in ageing tissues. Also, apoptosis is abrogated by HPV E6 mediated degradation of p53. The overexpression of the cyclin dependent kinase (CDK) inhibitor, p16INK4a, is a direct consequence of deregulated HPV oncogene expression.

In addition, host cell proteins important for proliferation and host cell genome replication may be overexpressed as a result of HPV infection. These host cell proteins include, ki67 (MIB-1), MYC cellular oncogene, Cyclin proteins (e.g., cyclin A, B, E, etc.), CDKN2A/p16INK4a, telomerase (e.g., TERC), replication complex proteins (e.g., MCM5, CDC6, topoisomerase II alpha (TOP2A), MCM2, minchromosome maintenance proteins 2, 4, and 5, etc.).

The one or more immunological assays as provided herein aims to employ user friendly procedures with simple instrument or no additional instrument to perform in a short period of time. Comparison of the results of the various immunological assays, nucleic acid hybridization assays with cytological and histological data for the human subjects as well as demographic information serve to validate the correlation and accuracy in diagnosing HPV infection and/or cervical cancer.

Another example of a method of screening a human subject infected with a human papillomavirus may include obtaining a clinical sample from the human subject, conducting a nucleic acid hybridization assay on the clinical sample, detecting the presence of a papillomavirus genome in the clinical sample from the human subject, conducting one or more immunological assays on the clinical sample, detecting the presence of an antibody to an early papillomavirus viral protein or the presence of the early papillomavirus viral protein in the clinical sample using a first recombinant protein of the early papillomavirus viral protein, and detecting the presence of an antibody to a late papillomavirus viral protein or the presence of the papillomavirus late viral protein in the clinical sample using a second recombinant protein of the late papillomavirus viral protein.

The one or more diagnostic immunological assays as described therein may also include obtaining polyclonal antibodies, monoclonal antibodies, and/or antiserum specific against the one or more recombinant proteins as obtained and described herein, taking a clinical sample likely to contain HPV associated proteins and/or antigens, reacting it with the obtained polyclonal antibodies, monoclonal antibodies, and/or antiserum specific for the one or more recombinant proteins, and assaying for the presence of any antibody-antigen complexes by suitable detection systems. Suitable detection system may employ various colormetric, chemiluminescent, fluorescent substrates, etc., specific for a secondary antibody used in each immunological assay.

Early diagnosis of HPV infection is important for successful prevention and treatment of cervical cancer. Strategies to prevent cervical cancer requires improved HPV testing/screening to cover a broad range of the worldwide population in addition to closely follow-up those subjects with past or present HPV infection and/or pre-cancerous lesions. Importantly, it is known that infection in women for 12-15 years with HPV is required before invasive cancer to develop. It is thus important to be able to assay biomarkers for HPV infection as described herein to pre-screen women early, such that it will be possible to treat HPV infection early and prevent cervical cancer development, rather than having to rely on chemotherapy or radiation to treat cancer malignancy.

TABLE 5

IHC staining results (stained %) and HPV DNA typing for 12 SCC biopsy samples and 12 ADC biopsy samples (C: Cytoplasmic; N: Nucleus; Dys: dysplasia or tumor cells).

| | | Anti-E7 | | | | Another anti-E7 Dys (%) | Anti-E6 Dys. (%) | Another anti-E6 Dys. (%) | Anti-L1 Dys (%) |
|---|---|---|---|---|---|---|---|---|---|
| | | Dys (% stained) | | Normal epith. (% stained) | | | | | |
| Sample # | HPV type | C | N | C | N | C | C | C | C |
| SCC-1 | 18 | 85 | 85 | 0 | 20 | 12.5 | 10 | 70 | 55 |
| SCC-2 | 16, 52 | 90 | 85 | 0 | 25 | 15 | 15 | 10 | 55 |
| SCC-3 | 16 | 60 | 65 | 0 | 40 | 5 | 0 | 10 | 20 |
| SCC-4 | 16 | 92 | 50 | 0 | 40 | 5 | 0 | 10 | 85 |
| SCC-5 | 16, 52, 58 | 92 | 55 | 0 | 50 | 20 | 5 | 15 | 88 |
| SCC-6 | 18, 52, 58 | 90 | 60 | | | 25 | 18 | 10 | 70 |
| SCC-7 | 16, 52 | 92 | 75 | 0 | 30 | 30 | 5 | 10 | 20 |
| SCC-8 | 16, 58 | 10 | 10 | 0 | 5 | 0 | 0 | 10 | 50 |
| SCC-9 | no DNA | 95 | 60 | 0 | 40 | 25 | 8 | 15 | 8 |
| SCC-10 | 18 | 92 | 65 | 0 | 60 | 45 | 25 | 20 | 65 |
| SCC-11 | 16, 58 | | | 0 | 80 | 5 | | 0 | 0 |
| SCC-12 | 33 | 95 | 90 | 0 | 0 | 30 | 1 | 20 | 55 |
| ADE-1 | 16, 18 | 30 | 20 | 0 | 50 | 15 | 25 | 20 | 82 |
| ADE-2 | no DNA | 62 | 40 | 0 | 30 | 35 | 70 | 35 | 78 |
| ADE-3 | 16 | 20 | 30 | 0 | 20 | 35 | 55 | | 60 |
| ADE-4 | 16, 18 | 80 | 80 | 0 | 0 | 10 | 5 | 0 | 90 |
| ADE-5 | 51, 52 | 95 | 80 | 0 | 50 | 10 | 70 | 15 | 92 |
| ADE-6 | 11, 16, 52 | | | 0 | 40 | 5 | 0 | 0 | 15 |
| ADE-7 | 18 | 50 | 40 | 0 | 60 | 25 | 20 | 20 | 75 |
| ADE-8 | 18 | 85 | 60 | 0 | 40 | 15 | 50 | 15 | 82 |
| ADE-9 | 45 | 82 | 55 | 0 | 30 | 30 | 2 | 20 | 40 |
| ADE-10 | 18 | 15 | 10 | 0 | 40 | 15 | 15 | 5 | 70 |
| ADE-11 | 18, 59 | 70 | 0 | 0 | 50 | 15 | 8 | 5 | 65 |
| ADE-12 | 18 | | | | | | | | 30 |

To analyze the HPV IHC results from each subject of invasive cancer, Table 5 shows data from 24 cases of invasive cancer samples with IHC score for staining of cytoplasm (C), and nucleus (N) using C, or N followed by the % of staining using the anti-HPV E7 antibody. Additional anti-HPV antibodies including another anti-E7 antibody, Anti-HPV E6 antibody like MAb1 and MAb 7 and anit-HPV L1 antibody were also tested on the same tissue microarray. To demonstrate the IHC staining by various anti-HPV antibodies, IHC score from cytoplasm staining of tumor cells using other anti-HPV antibodies is also shown in Table 5. Results of HPV DNA typing is also shown on the table for its corresponding case.

As shown in Table 5, both nucleus and cytoplasmic staining are found in all the subjects of tumor cells from SCC and ADE stained by the anti-E7 antibody. However, there is more staining (percentage stained) found in the cytoplasm of tumor cells compared to the staining of nuclear of tumor cells. The detection of HPV E7 protein in its adjacent normal epithelium cells was only found in the nucleus, but not found in the cytoplasm of the epithelial cells. The staining of cytoplasm appears most distinguishable in tumor cells compared to its corresponding normal adjacent cells. These data demonstrate expression of HPV E7 proteins was detected in the cytoplasm and nuclear of tumor cells of SCC and ADE tissues. The localization of the E7 proteins expressed in the cytoplasm of tumor cells, but not in the normal epithelium or stroma cells, appears to be tumor specific. HPV E7 proteins present in the nucleus of normal adjacent epithelium and tumor cells detected by the anti-HPV E7 antibody indicate HPV infection with oncoprotein expression. A similar staining pattern was also found when other anti-HPV antibodies were used as shown in Table 5. Data indicate that the HPV IHC assay as described herein can detect HPV early gene such as E6, E7, and late gene such as L1 proteins present in the tumor cells of cervical cancer tissues.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least HPV-16, HPV-18, HPV-33, HPV-45, etc, which are cancer-related HPV types (high risk HPV types). The single anti-E7 monoclonal antibody can also detect HPV infection by two or more HPV types, such as the combination of HPV 11, HPV-16, HPV-18, HPV-52, HPV-58, HPV-51, HPV-59, etc., which include high risk, low risk, and non-oncogenic α-papillomaviruses. However, infection by multiple HPV types contains at least one type that is a high-risk HPV type. These data indicate that the anti-E7 antibody described in this invention is non-type specific, and thus provides a powerful tool to detect HPV E7 proteins from most common high-risk HPV types in the cervical cancer.

The antibody-producing hybridoma cells were also screened with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types can be HPV 16, HPV 18, and other HPV types. The two or more different HPV types can be, for example, high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56. As an example, the first and the second purified recombinant human papillomavirus proteins may be recombinant HPV 16 E6 protein, recombinant HPV 16 E7 protein, recombinant HPV 16 L1 protein, recombinant HPV 18 E6 protein, recombinant HPV18 E7 protein, and recombinant HPV 18 L1 protein.

As an example of an ICC immunoassay, cells from cervical scrapes were directly smeared on the slides for immunostaining. As another example, cervical cells are collected into a liquid-based solution, centrifuged, washed, followed by immunostained with anti-HPV antibody. Cervical scrapes collected by liquid-based solution were processed according to the manufacture's instruction. The cervical cells were then processed by cytospin or thin prep techniques into a monolayer on a slide.

The thin layer of cells on the slide were then fixed and stained by the various anti-HPV antibodies of the invention. The anti-HPV antibodies may be tagged directly with a detection agent or may be detected by a secondary antibody tagged with a detection agent. Cells stained by the anti-HPV antibody were visualized under microscope.

To demonstrate the HPV ICC assay can be applied to different stages of dysplasia cells, samples from early, intermediate, or late stage of neoplasia are all tested. These samples include, but are not limited to, early stages like LSIL, or CIN1, or ASCUS, or intermediate stages like CIN2, CIN3, or HSIL, or late stages like SCC or ADE or others. To demonstrate the ICC assay described herein can be used to stain for various stages in samples from various sources, different stage of samples in different liquid based solutions were also prepared to perform ICC assay in this invention.

Figure 15B:
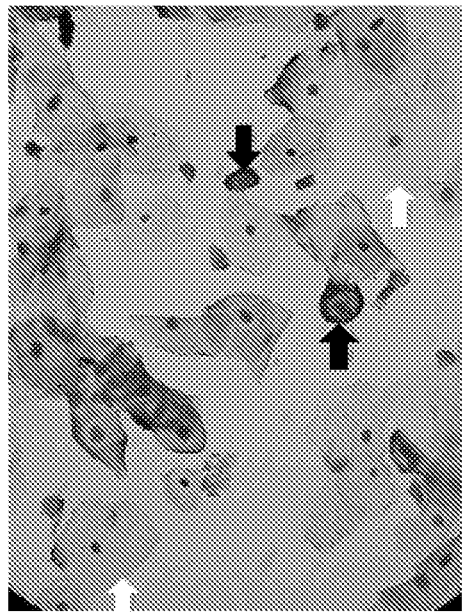
FIG. 15B shows the staining results of the same clinical sample as shown in FIG. 1A using an anti-HPV E7 mouse monoclonal antibody in an ICC assay according to another embodiment of the invention.
Figure 15A:
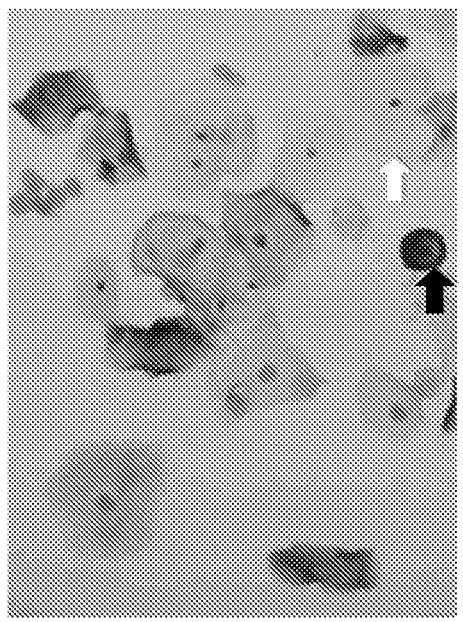
FIG. 15A shows the staining results of a clinical sample, diagnosed as ASCUS, in a liquid based solution using an anti-HPV E6 mouse monoclonal antibody in an ICC assay according to one embodiment of the invention.

To demonstrate HPV ICC assays are useful to identify abnormal cells underdetermined by standard cytological papanicolaou staining, for example, ASCUS (Atypical Squamous Cells of Undetermined Significance, atypical squamous cells of undetermined significance (ASCUS), unusual or atypical cells in pap smear that may be inconsequential or atypical glands of undetermined significance (AGUS), the HPV ICC assays are performed to test for ASCUS and AGUS samples. As shown in FIG. 15A, the results of ICC assay demonstrate that certain cervical scrape cells diagnosed as ASCUS by papanicolaou staining can be ICC stained positively using an anti-E6 monoclonal antibody. FIG. 15B shows the results of ICC assay from the same sample shown in FIG. 15A to demonstrate certain cervical scrape cells (diagnosed as ASCUS by papanicolaou staining) can be ICC stained positively using an anti-E7 monoclonal antibody. As shown in FIG. 15A and FIG. 15B, the abnormal cell with high N/C (nuclear/cytoplasm) ratio (indicated by black arrow) was stained positively while the normal cells (big, irregular cell shape with small nuclear) stain negatively as indicated by the white arrow. Both FIG. 15A and FIG. 15B demonstrate HPV E6 and HPV E7 proteins can be detected in the abnormal cells from samples with pap smear ASCUS. These results indicate that this ASCUS sample containing HPV infected cells with E6 and E7 oncogenic proteins expressed, thus can be detected in situ using the mouse monoclonal anti-HPV E6 and the mouse anti-HPV E7 monoclonal antibody respectively, by the ICC assay described in this invention.

Figure 16B:
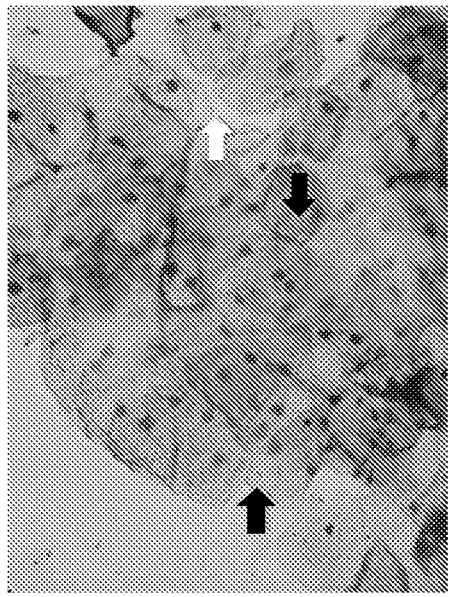
FIG. 16B shows the staining results of another clinical sample, diagnosed as CIN2, in a liquid based solution using an anti-HPV E6 mouse monoclonal antibody in an ICC assay according to another embodiment of the invention.
Figure 16A:
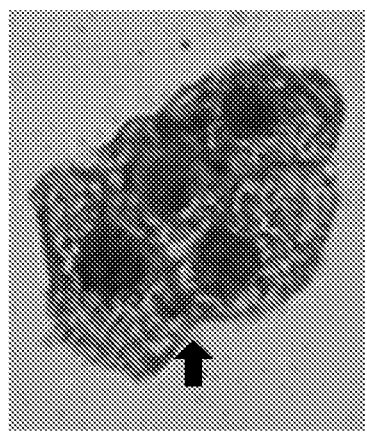
FIG. 16A shows the staining results of a clinical sample, diagnosed as CIN2, in a liquid based solution using an anti-HPV E7 mouse monoclonal antibody in an ICC assay according to one embodiment of the invention.

To demonstrate the HPV ICC assay can detect HSIL cells, FIG. 16A shows cervical scrape cells diagnosed as CIN2 by papanicolaou staining. These cells were prepared in another liquid-based solution and are ICC-stained positively using an anti-E7 monoclonal antibody. As shown in FIG. 16A, the CIN2, HSIL abnormal cells are stained positively to the nucleus and cytoplasm. These cells are in the form of connecting each other with high nuclear to cytoplasm (N/C) ratio as indicated by the black arrow. These results demonstrate that HPV E7 protein present in situ can be detected in the abnormal cells from an intermediate stage of neoplasm, in various liquid-based solutions using the mouse monoclonal anti-HPV E7 described herein.

As an another example, FIG. 16B shows another CIN2 sample of cervical scrape cells prepared in another liquid-based solution that are ICC stained positively using an anti-E6 monoclonal antibody. As shown in FIG. 16B, the CIN2, HSIL abnormal cells was ICC-stained positively to the nucleus and cytoplasm. These cells are in the form of connecting each other with high N/C (nuclear/cytoplasm) ratio (indicated as black arrow) These results demonstrate that HPV E6 protein present in situ can be detected in the abnormal cells from an intermediate stage of neoplasm, in various liquid based solution using the mouse monoclonal anti-HPV E6 described herein.

An immunocytochemical (ICC) assay not only detects HPV infection, but also detects HPV oncogenic proteins in situ. Therefore, ICC assay alone, or in combination with various specific and common anti-HPV antibodies can be a powerful tool for HPV detection in situ, as compared to a standard HPV DNA test or pap smear assay.

TABLE 6

ICC staining results using a mouse anti-HPVE6 monoclonal antibody on various cervical scrape samples in a liquid-based solution.

| Pap smear | normal | ASCUS | ASC-H | CIN1 | CIN2/3 | SCC |
|---|---|---|---|---|---|---|
| ICC positive, using an anti-HPV E6 antibody | 4 | 3 | 4 | 11 | 17 | 4 |
| ICC negative, using an anti-HPV E6 antibody | 25 | 6 | 4 | 6 | 0 | 1 |
| total | 29 | 9 | 8 | 17 | 17 | 5 |
| positive rate | 14% | 33% | 38% | 65% | 100% | 80% |

Table 6 shows the results of an ICC assay using a mouse anti-HPVE6 monoclonal antibody on various cervical scrape samples in a liquid-based solution. The results in Table 6 demonstrate that HPV E6 protein can be detected in situ in single cells fixed on a slide by immunocytochemical (ICC) assay using a mouse monoclonal anti-HPV E6 antibody. The in situ presence of HPV E6 proteins can be detected in various stages of cervical scrape samples in various liquid-based solutions. The same cervical scrape samples were also processed by standard papinouli staining to compare the ICC staining results with the pap smear results. As shown in Table 6, HPV E6 proteins are present in the cervical scrape normal, ASCUS, ASC-H, CIN1, CIN2/3 samples with increasing positively rate, respectively.

TABLE 7

ICC staining results using a mouse monoclonal anti-HPVE7 antibody on various cervical scrape samples in a liquid-based solution.

| Pap smear | normal | ASCUS | ASC-H | CIN1 | CIN2/3 | SCC |
|---|---|---|---|---|---|---|
| ICC positive, using an anti-HPV E7 antibody | 3 | 4 | 3 | 11 | 16 | 4 |
| ICC negative, using an anti-HPV E7 antibody | 25 | 6 | 5 | 6 | 1 | 1 |
| total | 28 | 10 | 8 | 17 | 17 | 5 |
| positive rate | 11% | 40% | 38% | 65% | 94% | 80% |

As another example of the HPV detecting ICC assay, Table 7 show results of ICC staining using anti-HPV E7 antibody. HPV anti-E7 gives comparable ICC results as what is shown for HPV anti-E6. HPV E7 proteins are present in the cervical scrape normal, ASCUS, ASC-H, CIN1, CIN2/3 samples with increasing positively rate, respectively. There is about 94% positive rate for samples diagnosed with pap smear CIN2/3, while only 11% of samples diagnosed with pap smear normal stained positively by ICC using the same anti-HPVE7 antibody. For ASCUS or ASC-H samples, about 40% of these samples are stained positively by the same anti-HPV E7 antibody as used for the CIN1, CIN2/3 samples shown in Table 3, indicating expression of oncogenic proteins in these ASCUS or ASC-H sample subjects to be followed up for further cancer progression. For samples with pap smear diagnosed as ASCUS and ICC staining (anti-HPV E7) as negative, there may be a lower risk to develop a progressive lesion.

An object of the invention is to develop immune-responsive or antibody-reactive recombinant proteins derived from early genes and/or late genes of various HPV types and strains. It is a further object to provide these recombinant proteins in a chemically pure form. It is a still further object to provide simple, rapid, less expensive and more sensitive assays/tests for diagnosing not only HPV infection, but also most, if not all, HPV-associated neoplasm.

Cloning and production of recombinant proteins encoded by HPV genes: Recombinant proteins encoded by early HPV genes and late HPV genes are obtained. Recombinant proteins can be obtained by itself or as hybrid proteins fused transcriptionally or translational to a portion of a full length DNA fragment for a HPV gene of interest. The DNA sequence of the HPV gene of interest may be derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6: GI:9627356; HPV51-E6: GI:9627155; HPV52-E6: GI:9627370; HPV56-E6: GI:9627383; HPV59-E6: GI:9627962; HPV58-E6: GI:9626489; H PV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Cloning and production of various recombinant proteins encoded by HPV-16, early E6 gene: Cloning of an exemplary oncogenic E6 early gene from an exemplary HPV type, HPV-16, is described herein. A 474 base pair (b.p.) DNA fragment (SEQ ID NO. 1) containing the 157 amino acid coding region (SEQ ID NO. 2) of the HPV-16 E6 gene was obtained by polymerase chain reaction (PCR) amplification. Primers were used for cloning, for example, a pair of forward and reverse primers, 5' cgcGGATCCcaccaaaagagaactgcaatgtttc 3' (SEQ ID NO. 3) and 5' cccAAGCTTttacagctgggtttctctacgtg 3' (SEQ ID NO. 4), respectively. The DNA sequence of the isolated DNA fragment was confirmed by comparing with the sequence from Gene Bank database. All cloning procedures are carried out according to the protocols described in "Molecular Cloning", A Laboratory Manual, eds. Sambrook, Fritsch and Maniatis, Cold Spring Harbor Laboratory Press, 1989. In addition, E6 DNA fragments from different strains of HPV-16 can also be cloned from different clinical samples or sources.

The obtained 474 base pair (b.p.) DNA fragment was subcloned into a histidine tag expression vector, pQE30, in order to express a his-tagged recombinant HPV-16 E6 protein. The resulting plasmid DNA is designated, pQE30/HPV16-E6 for the expression of His-tagged-HPV16-E6 recombinant protein. The DNA sequence and the amino acid sequences of the resulting his-tagged recombinant HPV-16 E6 protein are shown as SEQ ID NO. 5 (a 510 base pair (b.p.) DNA fragment) and SEQ ID NO. 6 (a 169 amino acid fusion protein), respectively.

Cloning and production of recombinant proteins encoded by HPV-16 early E7 gene: Cloning of an exemplary oncogenic E7 early gene from an exemplary HPV type, HPV-16, is described herein. A 294 base pair (b.p.) DNA fragment (SEQ ID NO. 7) containing the 99 amino acid coding region (SEQ ID NO. 8) of the HPV-16 E7 gene was obtained by polymerase chain reaction (PCR) amplification. Primers were used for cloning, for example, a pair of forward and reverse primers, 5' cgcGGATCCcatggagatacacctacattgc 3' (SEQ ID NO. 9) and 5' ccgGAATTCttatggtttctgagaacagatgg 3' (SEQ ID NO. 10), respectively. The DNA sequence of the isolated DNA fragment was confirmed by comparing with the sequence from Gene Bank database. In addition, E7 DNA fragments from different strains of HPV-16 can also be cloned from different clinical samples or sources.

The obtained 294 base pair (b.p.) DNA fragment was subcloned into a GST expression vector in order to express a recombinant HPV-16 E7 GST fusion protein. The DNA sequence and the amino acid sequences of the resulting recombinant HPV-16 E7 GST protein are shown as SEQ ID NO. 11 (a 972 base pair (b.p.) DNA fragment) and SEQ ID NO. 6 (a 323 amino acid fusion protein), respectively. The molecular weight of the resulting recombinant HPV-16 E7 GST protein is about 37.2 KD. The recombinant HPV-16 E7 GST proteins were obtained and purified to a final concentration of about 1 mg/L. Other expression systems can also be used to express E7 recombinant proteins from various HPV types and strains. Recombinant E7 fusion proteins or recombinant E7 baculovirus proteins were used to detect the presence of E7 antibody on clinical samples and were also be used as immunogens for production of polyclonal antiserum and monoclonal antibodies.

To analyze the HPV IHC results from each subject of CIN3, Table 8 shows data from 30 cases of CIN 3 samples with IHC score for staining of cell membrane (M), cytoplasm (C), and nucleus (N) using M, C, or N followed by the % of staining with the anti-E7 antibody. Additional anti-HPV antibodies including Anti-HPV E6 antibody like MAb1 and MAb 7 and anit-HPV L1 antibody were also also tested on the same tissue microarray. To demonstrate the IHC staining by various anti-HPV antibodies, IHC score from cytoplasm staining of tumor cells using other anti-HPV antibodies was also shown in Table 5. Results of HPV DNA typing were also shown on the table for its corresponding case.

As shown in Table 8, nucleus staining is found in the dysplasia cells of all the CIN3 samples tested while only a certain proportion of cases found staining of cytoplasm by the anti-E7 antibody. The results indicate that there is more staning found in the cytoplasm than in the nucleus of dysplasia cells. As shown previously in invasive cancer tissues, HPV E7 protein in its adjacent normal epithelium cells was only found in the nucleus, but not found in the cytoplasm of the epithelial cells. The staining of cytoplasm appears most distinguishable in dysplasia cells compared to its corresponding normal adjacent cells. The localization of the E7 proteins expressed in the cytoplasm of dysplasia cells, but not in the normal epithelium or stroma cells appears HSIL specific. These data demonstrate expression of HPV E7 proteins can be detected in the cytoplasm and nucleus of dysplasia cells of CIN3 tissues. HPV E7 proteins in the nucleus of normal adjacent epithelium and dysplasia cells detected by the anti-HPV E7 antibody indicate HPV infection with oncoproteins expression. For the cases with high level expression of HPV E7 proteins detected in the cytoplasm of dysplasia cells, it may suggest specific indication of dysplasia progression. A similar staining pattern was also found when other anti-HPV antibodies were used as shown in Table 8. Data indicate that the HPV IHC assay as described herein can detect HPV early genes such as E6, E7, and late genes such as L1 proteins present in the dysplasia cells of CIN3.

Comparing the results of HPV IHC to the HPV DNA typing, the anti-E7 antibody reacts positively with all the HPV types present in the samples tested. For example, the anti-E7 monoclonal antibody as described herein can detect a single HPV infection by at least HPV-16, HPV-18, HPV-31, HPV-33, HPV-39, HPV-58, etc., which are cancer-related HPV types (high risk HPV types). The single anti-E7 monoclonal antibody can also detect HPV infection by two or more HPV types, such as the combination of HPV-16, HPV-18, HPV-33, HPV-39, HPV-52, HPV-58, etc., which include most common high-risk HPV. These data indicate that the anti-E7 antibody described in this invention is non-type specific, and thus provides a powerful tool to detect HPV E7 proteins from most common high-risk HPV types in the CIN3 tissues.

TABLE 8

IHC staining results (stained % and score; 0-3) and HPV DNA typing of 30 CIN 3 samples (M: Membrane; C: Cytoplasmic; N: Nucleus; Dys: Dysplasia).

| | | anti-E7 | | | | | | Anti-E6 Dys. (%) | Another anti-E7 Dys. (%) | Anti-L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 31 | 33 | 0 | 80 | 80 | 0 | 0 | 50 | 70 | 40 | 80 |
| 32 | 16 | 0 | 80 | 80 | | 0 | 60 | 0 | 0 | 5 |
| 33 | 16, 58 | | | | 0 | 0 | 60 | | | |
| 34 | 31 | 0 | 50 | 70 | 0 | 0 | 50 | 0 | 0 | 10 |
| 35 | 16, 39 | 0 | 70 | 90 | 0 | 0 | 40 | 0 | 10 | 30 |
| 36 | 31 | 0 | 70 | 60 | 0 | 0 | 50 | 0 | 20 | 20 |
| 37 | 39 | 0 | 0 | 40 | 0 | 0 | 0 | 0 | 0 | 0 |
| 38 | 16 | | | | 0 | 0 | 40 | | | |
| 39 | 16 | 0 | 60 | 70 | 0 | 0 | 40 | 0 | | 0 |
| 40 | 58 | 0 | 90 | 90 | 0 | 0 | 50 | 50 | 0 | 30 |
| 41 | 16 | 0 | 0 | 50 | 0 | 0 | 50 | 0 | 20 | 20 |
| 42 | 16 | 0 | 70 | 70 | 0 | 0 | 30 | 0 | 0 | |
| 43 | 33 | 0 | 0 | 90 | 0 | 0 | 50 | 0 | 0 | 5 |
| 44 | 52 | 0 | 70 | 80 | 0 | 0 | 50 | 70 | 10 | 50 |
| 45 | 51, 52 | 0 | 90 | 90 | 0 | 0 | 30 | 80 | 50 | 10 |
| 46 | 16 | 0 | 0 | 80 | 0 | 0 | 50 | 0 | 0 | 5 |
| 47 | 16 | 0 | 60 | 80 | 0 | 0 | 50 | 30 | 10 | 20 |
| 48 | 16, 58 | 0 | 0 | 80 | 0 | 0 | 50 | 0 | 0 | 10 |
| 49 | 31 | 0 | 80 | 60 | | | 50 | 70 | 40 | 40 |
| 50 | 16 | 0 | 0 | 60 | 0 | 0 | 30 | 0 | 20 | 20 |
| 51 | 6 | | | | 0 | 0 | 20 | | 0 | |
| 52 | 16, 18, 33, 39 | 0 | 0 | 20 | 0 | 0 | 30 | 0 | 0 | 0 |
| 53 | 51, 52, 58 | 0 | 70 | 60 | 0 | 0 | | 60 | 60 | 40 |
| 54 | 16, 45 | 0 | 0 | 70 | 0 | 0 | 50 | 0 | 20 | 20 |
| 55 | 16 | 0 | 0 | 75 | 0 | 0 | 50 | 0 | 0 | 0 |
| 56 | 33, 52 | 0 | 0 | 80 | 0 | 0 | 50 | 0 | 0 | 10 |
| 57 | 16 | 0 | 0 | 50 | 0 | 0 | 40 | 0 | 0 | 0 |
| 58 | 33 | 0 | 0 | 80 | 0 | 0 | | 0 | 20 | 10 |
| 59 | 16 | 0 | 0 | 60 | 0 | 0 | 20 | 0 | 10 | 5 |
| 60 | 16, 52, 58 | 0 | 70 | 80 | 0 | 0 | 50 | 70 | 0 | 20 |

What is claimed is:

1. A monoclonal antibody that specifically binds to two or more native HPV proteins from different HPV types, wherein said two or more native HPV proteins are native E7 proteins from different HPV types or native E6 proteins from different HPV types, and wherein said monoclonal antibody binds in situ to said proteins in a clinical sample.

2. The monoclonal antibody of claim 1, wherein the monoclonal antibody specifically binds to a native E7 protein from HPV 16 and a native E7 protein from HPV 18.

3. The monoclonal antibody of claim 1, wherein the monoclonal antibody specifically binds to a native E6 protein from HPV 16 and a native E6 protein from HPV 18.

4. The monoclonal antibody of claim 1, wherein the different HPV types are selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56.

5. A monoclonal antibody that specifically binds in situ in a clinical sample to two or more native E7 proteins from different HPV types.

6. The monoclonal antibody of claim 5, wherein the monoclonal antibody specifically binds to a native E7 protein from HPV 16 and a native E7 protein from HPV 18.

7. A monoclonal antibody that specifically binds in situ in a clinical sample to a native HPV E7 protein and a native HPV E6 protein, wherein the native HPV E7 protein and the native HPV E6 protein are from the same HPV type.

8. The monoclonal antibody of claim 7, wherein said native E7 protein and said native E6 protein are from HPV 16.

9. The monoclonal antibody of claim 7, wherein said native E7 protein and said native E6 protein are from HPV 18.

10. The monoclonal antibody of claim 7, wherein the native HPV E7 proteins and the native HPV E6 proteins are from the same HPV type selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56.

* * * * *